United States Patent
Page et al.

(10) Patent No.: US 10,056,554 B2
(45) Date of Patent: Aug. 21, 2018

(54) FUNCTIONAL INTERLAYERS OF FULLERENE DERIVATIVES AND APPLICATIONS IN ORGANIC SOLAR CELLS

(71) Applicant: University of Massachusetts, Boston, MA (US)

(72) Inventors: Zachariah Page, Sunderland, MA (US); Yao Liu, Amherst, MA (US); Thomas P. Russell, Amherst, MA (US); Todd Emrick, South Deerfield, MA (US)

(73) Assignee: University of Massachusetts, Boston, MA (US)

( * ) Notice: Subject to any disclaimer, the term of this patent is extended or adjusted under 35 U.S.C. 154(b) by 0 days.

(21) Appl. No.: 15/306,752

(22) PCT Filed: May 6, 2015

(86) PCT No.: PCT/US2015/029362
§ 371 (c)(1),
(2) Date: Oct. 25, 2016

(87) PCT Pub. No.: WO2015/171689
PCT Pub. Date: Nov. 12, 2015

(65) Prior Publication Data
US 2017/0047520 A1    Feb. 16, 2017

Related U.S. Application Data

(60) Provisional application No. 61/990,305, filed on May 8, 2014.

(51) Int. Cl.
*H01L 51/00* (2006.01)
*C01B 32/15* (2017.01)
(Continued)

(52) U.S. Cl.
CPC .......... *H01L 51/0047* (2013.01); *C01B 32/15* (2017.08); *C07D 209/56* (2013.01);
(Continued)

(58) Field of Classification Search
CPC . H01L 51/0047; H01L 51/4253; H01L 51/00; H01L 51/0037; H01L 51/0036;
(Continued)

(56) References Cited

U.S. PATENT DOCUMENTS

2013/0160827 A1* 6/2013 Jen .................... H01L 31/02167
136/252

OTHER PUBLICATIONS

Dongbo Mi "Synthesis of a soluble fulleropyrrolidine derivative for use as an electron acceptor in bulk-heterojunction polymer solar cells" Synthetic Metals 162 (2012) 483-489.*

(Continued)

*Primary Examiner* — Jeffrey T Barton
*Assistant Examiner* — Michael Y Sun
(74) *Attorney, Agent, or Firm* — Milstein Zhang & Wu LLC

(57) ABSTRACT

The invention provides novel materials, methods and designs to enable improved power conversion efficiencies of organic photovoltaics (OPVs). In particular, the invention provides novel materials and interlayers for polymer-based solar cells. Novel functional fullerene-based interlayers are disclosed that enable high efficiency devices in conjunction with numerous active layer and electrode materials.

9 Claims, 28 Drawing Sheets

(51) Int. Cl.
*C07D 209/56* (2006.01)
*C07F 9/572* (2006.01)
*C07D 409/14* (2006.01)
*C07D 209/94* (2006.01)
*H01L 51/42* (2006.01)
*H01L 51/44* (2006.01)
*C01B 32/152* (2017.01)

(52) U.S. Cl.
CPC ......... *C07D 209/94* (2013.01); *C07D 409/14* (2013.01); *C07F 9/5728* (2013.01); *H01L 51/0036* (2013.01); *H01L 51/0037* (2013.01); *H01L 51/0045* (2013.01); *H01L 51/0046* (2013.01); *H01L 51/0048* (2013.01); *H01L 51/0049* (2013.01); *C01B 32/152* (2017.08); *H01L 51/0043* (2013.01); *H01L 51/4253* (2013.01); *H01L 51/441* (2013.01); *Y02E 10/549* (2013.01)

(58) Field of Classification Search
CPC ............ H01L 51/441; H01L 51/0049; H01L 51/0045; H01L 51/0046; H01L 51/0048; H01L 51/0043; C07D 209/94; C07D 409/14; C07D 209/56; C07F 9/5728; Y02E 10/549; C01B 31/0213; C01B 32/15
See application file for complete search history.

(56) References Cited

OTHER PUBLICATIONS

Maria del Carmen Gimenez-Lopez "Functionalized Fullerenes in Self-Assembled Monolayers" Langmuir 2011, 27, 10977-10985.*
La-ongnuan Srisombat "Thermal Stability of Mono-, Bis-, and Tris-Chelating Alkanethiol Films Assembled on Gold Nanoparticles and Evaporated "Flat" Gold" Langmuir 2010, 26(1), 41-46.*
Fabio Aricò "Sulfur and Nitrogen Mustard Carbonate Analogues" Eur. J. Org. Chem. 2012, 3223-3228.*
Subashree Iyer "A nonhydrolyzable analogue of phosphotyrosine, and related aryloxymethano- and aryloxyethano-phosphonic acids as motifs for inhibition of phosphatases" Bioorganic & Medicinal Chemistry Letters 14 (2004) 5931-5935.*

* cited by examiner

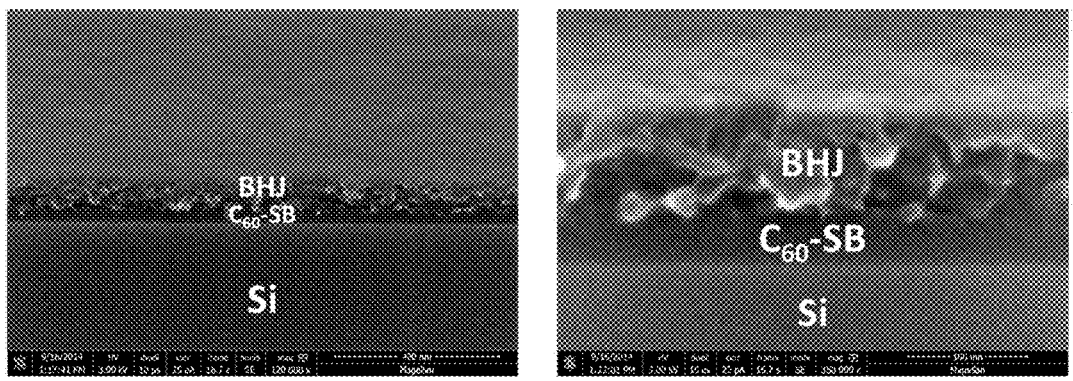
FIG. 38
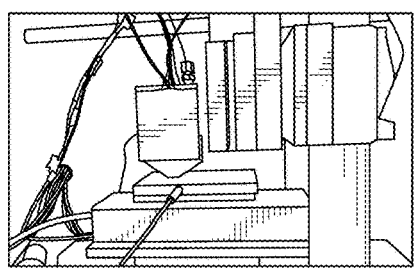
FIG. 39A
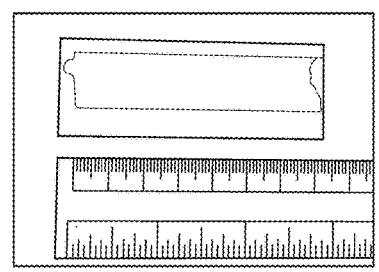
FIG. 39B
FIG. 39C
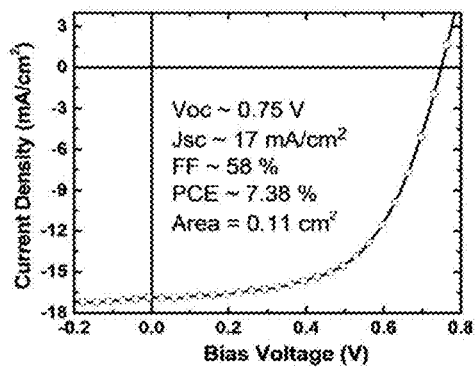
FIG. 39D
FIG. 39

| Fullerene | Eg (ev) | $I_P$ (ev) | $E_A$ (ev) | $\Delta_{Ag}$ (ev) |
|---|---|---|---|---|
| $C_{60}$-N | 1.83 | 5.59 | 3.76 | -0.91 ± 0.02 |
| $C_{70}$-N | 1.68 | 5.57 | 3.89 | -0.82 ± 0.01 |
| Mixed F-N | 1.83;1.68 | 5.63 | 3.80;3.95 | -0.84 ± 0.01 |

FUNCTIONAL INTERLAYERS OF FULLERENE DERIVATIVES AND APPLICATIONS IN ORGANIC SOLAR CELLS

PRIORITY CLAIMS AND RELATED PATENT APPLICATIONS

This application is the U.S. national phase of and claims priority to PCT/US15/29362, filed May 6, 2015, which claims the benefit of priority from U.S. Provisional Application Ser. No. 61/990,305, filed on May 8, 2014, the entire content of each of which is incorporated herein by reference in its entirety.

GOVERNMENT RIGHTS

The United States Government has certain rights to the invention pursuant to Grant/Contract Nos. DE-SC0001087 and DE-AC05-060R23100 from U.S. Department of Energy and Grant/Contract No. DMR-0820506 from the NSF.

TECHNICAL FIELDS OF THE INVENTION

The invention generally relates to materials and methods for organic photovoltaics and solar cells. More particularly, the invention relates to novel functional fullerene interlayers, their applications in organic photovoltaics, and the resulting improved solar cells.

BACKGROUND OF THE INVENTION

Organic photovoltaics (OPVs) is a rapidly growing area of research worldwide due to its promise to offer low temperature, inexpensive processing of lightweight and flexible solar cells. OPV cells based on organic polymers are of interest as alternative sources of renewable electrical energy to the typical silicon-based cell. Dramatic improvements in power conversion efficiency (PCE) of bulk heterojunction (BHJ) polymer-containing solar cells (PSCs) include recent reports on devices with PCE values exceeding 9%. (He, et al. 2012 *Nat. Photonics* 6, 591-595; You, et al. 2013 *Nat. Commun.* 4, 1410-1446; Liu, et al. 2013 *Sci. Rep.* 3, 3356; You, et al. 2013 *Adv. Mater.* 25, 3973-3978; Yao, et al. 2014 *Adv. Energy Mater.* doi:10.1002/aenm.201400206.)

However, achieving such high efficiency requires increasingly complex polymer syntheses and device architectures (e.g. fabrication of tandem devices). In addition, the use of aluminum as the most common metal cathode lacks practicality owing to its rapid oxidation and inability to be processed from solution. More stable metals, like Ag, Cu, or Au, can be deposited from solution, but have limited utility as cathodes in organic photovoltaics due to their high work-function ($\Phi$) that further limits the open circuit voltage ($V_{OC}$), short circuit current density ($J_{SC}$), and fill factor (FF) due to low a built-in electrostatic potential difference across the device. (Krebs 2009 *Sol. Energ. Mat. Sol. Cells* 93, 465-475; Krebs, et al. 2009 *J. Mater. Chem.* 19, 5442-5451; Guo, et al. 2013 *Adv. Energy Mater.* 3, 1062-1067.)

To circumvent this limitation, a thin buffer layer inserted between the active layer and cathode tailors the interface, maximizes $V_{OC}$, and minimizes contact resistance. Numerous inorganic buffer layers have been studied, such as Ca and LiF, while organic interlayers would be better suited to solution-based device fabrication. (Yip, et al. 2012 *Energy Environ. Sci.* 5, 5994-6011; Duan, et al. 2013 *Chem. Soc. Rev.* 42, 9071-9104; Gu, et al. 2014 *Adv. Energy Mater.* doi:10.1002/aenm.201301771.)

Conductive interlayers such as Ca, advantageous for their intrinsically low $\Phi$, suffer from their relative lability and sensitivity to oxygen or water. Polar organic interlayers permit layer-by-layer solution deposition, but have poor adhesion to low surface energy active layers, thus limiting their utility in conventional device architectures (as fabricated from anode-to-cathode). (Zhang, et al. 2013 *J. Mater. Chem. A* 1, 9624-9629.) Furthermore, buffer layers are typically very thin (<5 nm), so as to prevent charge-build up due to large injection barriers at the active layer/buffer layer interface or slow charge transport through the buffer layer. However, from a processing standpoint, the need to reproduce precise nanometer or sub-nanometer interlayer thicknesses is in itself problematic.

Buffer layers, or interlayers, lower the work function of the cathode, with a magnitude frequently described by the interfacial dipole ($\Delta$), where large negative $\Delta$ values have produced some of the most effective reported OPVs. (Worfolk, et al. 2012 *Adv. Energy Mater.* 2, 361-368.) For example, solution-processed dimethylaminopropyl-substituted polyfluorene (PFN) yielded a maximum PCE of 9.21% in an inverted device, while poly(ethyleneimine) (PEI) and its derivatives enabled all-solution-processed inverted devices with maximum PCE values of 8.9%. (Zhou, et al. 2012 *Science* 336, 327-332; Woo, et al. 2014 *Adv. Energy Mater.* doi:10.1002/aenm.201301692.) In each case, the amine functionality of the interlayer is responsible for the large negative $\Delta$ values (<−0.5 eV). However, these interlayers have their own drawbacks—the PFN backbone is intrinsically p-type, while PEI is insulating and exhibits poor adhesion to the photoactive layer.

With respect to electrode selection, recent reports of BHJ PSCs using a bathocuproine (BCP) interlayer with a Ag cathode achieved PCEs of 7.7 and 8.1%, representing benchmark values to-date for standard single-junction PSCs containing Ag cathodes. (Martinez-Otero, et al. 2013 *Adv. Optical Mater.* 1, 37-42; Betancur, et al. 2013 *Nat. Photonics* 7, 995-1000.) However, BCP requires a thermal deposition step and a precisely defined interlayer thickness (3.5 nm) to be effective. (Martinez-Otero, et al. 2013 *Adv. Optical Mater.* 1, 37-42.) Conjugated polymer zwitterions (CPZs) were recently reported that show large negative $\Delta$ values (−0.5 eV to −0.9 eV) on metal electrodes. (Page, et al. 2013 *Macromolecules* 46, 344-351; Liu, et al. 2013 *Adv. Mater.* 25, 6868-6873; Page, et al. 2014 *Chem. Sci.* doi:10.1039/c4sc00475b.) Spin-coating CPZs and the active layer polymer from orthogonal solvents provides good control over interlayer thickness with little disruption of the underlying surface. To date, CPZs have demonstrated effectiveness as interlayers in OPV devices over a thickness range of ~5-10 nm; however, thicker films are not useful due to the p-type characteristics of the selected polymers. (Liu, et al. 2013 *Adv. Mater.* 25, 6868-6873.)

Inverted polymer solar cells (iPSCs) containing high work function metal anodes (e.g., Ag or Au) and modified indium tin oxide (ITO) cathodes exhibit superior efficiency and stability over PSCs with a conventional geometry. (He, et al. 2012 *Nat. Photon.* 6, 591; Chen, et al. 2009 *Adv. Mater.* 21, 1434; Hau, et al. 2010 *Polym. Rev.* 50, 474; Jorgensen, et al. 2012 *Adv. Mater.* 24, 580; Liu, et al. 2013 *J. Am. Chem. Soc.* 135, 15326; Zhang, et al. 2014 *Adv. Energy Mater.* DOI: 10.1002/aenm.201400359.) iPSCs preclude the need for a poly(3,4-ethylenedioxythiophene):poly(styrenesulfonic acid) (PEDOT:PSS) hole transport layer, which is corrosive to ITO and leads to device deterioration. (Xu, et al. 2009

Adv. Funct. Mater. 19, 1227; Yang, et al. 2012 Adv. Energy Mater. 2, 523; Jorgensen, et al. 2008 Sol. Energ. Mat. Sol. C. 92, 686.)

A major limitation associated with iPSCs is the large barrier to electron extraction at the photoactive layer-ITO interface. To address this limitation, inorganic materials are implemented as electron transport layers (ETLs), including zinc oxide (ZnO), cesium carbonate ($Cs_2CO_3$), titanium oxide ($TiO_x$), and titanium chelate. (You, et al. 2012 Adv. Mater. 24, 5267; White, et al. 2006 Appl. Phys. Lett. 89, 143517; Sun, et al. 2011 Adv. Mater. 23, 1679; Li, et al. 2006 Appl. Phys. Lett. 88, 253503; Liao, et al. 2008 Appl. Phys. Lett. 92, 173303; Waldauf, et al. 2006 Appl. Phys. Lett. 89, 233517; Tan, et al. 2012 Adv. Mater. 24, 1476.) However, organic ETLs possess inherent advantages over inorganic layers for their ease of processing and favorable mechanical properties. (Yip, et al. 2012 Energy Environ. Sci. 5, 5994; Duan, et al. 2013 Chem. Soc. Rev. 42, 9071.) Prime examples of organic ETLs used for ITO modification in iPSCs include polyfluorene derivatives (PFNs), polyethyleneimine (PEI), and ethoxylated polyethyleneimine (PEIE). (He, et al. 2012 Nat. Photon. 6, 591; Liu, et al. 2013 J. Am. Chem. Soc. 135, 15326; He, et al. 2011 Adv. Mater. 23, 4636; Kang, et al. 2012 Adv. Mater. 24, 3005; Lee, et al. 2013 Energy Environ. Sci. 6, 1152; Zhou, et al. 2012 Science 336, 327.) In these devices, the amine groups impart a large negative interfacial dipole (Δ) (<−0.5 eV) that reduces the energy barrier to charge extraction and increases the built-in potential of the device. However, these ETLs have drawbacks—the PFN backbone is intrinsically p-type, whereas PEI and PEIE are insulating and exhibit poor adhesion to the active layer.

Interest is thus emerging in fullerene-based ETLs that promote rapid electron transport and selectivity, and provide the capacity for π-π interactions to enhance adhesion with the active layer. (Yao, et al. 2014 Adv. Energy Mater. 4, 1400206; O'Malley, et al. 2012 Adv. Energy Mater. 2, 82; Yang, et al. 2013 Adv. Energy Mater. 3, 666; Wei, et al. 2008 Adv. Mater. 20, 2211; Mei, et al. 2013 ACS Appl. Mater. Interfaces 5, 8076; Li, et al. 2013 J. Mater. Chem. A 1, 12413; Li, et al. 2013 Adv. Energy Mater. 3, 1569; Lai, et al. 2013 ACS Appl. Mater. Interfaces 5, 5122.) However, only a few examples of fullerene based ETLs are sufficiently robust to endure multilayer solution processing, including thermally cross-linked fullerene derivatives, a phosphoric diethyl ester functionalized fullerene, a fullerene/ZnO composite, and a blend of fulleropyrrolidinium iodide (FPI) and PEIE (FPI-PEIE). (Hsieh, et al. 2010 J. Am. Chem. Soc. 132, 4887; Duan, et al. 2012 Chem. Mater. 24, 1682; Cheng, et al. 2013 ACS Appl. Mater. Interfaces 5, 6665; Liao, et al. 2013 Adv. Mater. 25, 4766; Liao, et al. 2014 Sci. Rep. 4, 6813; Li, et al. 2014 Adv. Mater. 26, 6262.)

Realizing uniform ultrathin films over large areas represents a significant challenge, yet most efficient iPSCs reported to-date require an ultrathin ETL (e.g., ~5 nm of PEIE or PFN). While a recent report describing the incorporation of mercury into PFN (PFEN-Hg) achieves thickness independent properties, mercury carries inherent practical limitations. (Liu, et al. 2013 J. Am. Chem. Soc. 135, 15326.) Doping FPI with PEIE (FPI-PEIE) also leads to an ETL thickness independence, but the doping ratio needs to be elaborately controlled. (Li, et al. 2014 Adv. Mater. 26, 6262.) Simpler materials are thus needed to improve the properties of large area coatings while maintaining device efficiency.

Accordingly, there remains an urgent, on-going need for novel materials, methods and designs to enable improved power conversion efficiencies of OPVs, especially novel approaches to interlayers for polymer-based solar cells.

SUMMARY OF THE INVENTION

The invention provides novel materials, methods and designs to enable improved power conversion efficiencies of OPVs, especially novel approaches to interlayers for polymer-based solar cells. Novel functional fullerene-based interlayers are disclosed that enable high efficiency devices in conjunction with numerous active layer and electrode materials. High PCEs (exceeding 8.5%) were obtained irrespective of the cathodes work-function, even for the high work function Au, indicating a universal utility of these interlayers. The invention also allows dual utility of $C_{60}$-SB in acting as a thickness insensitive cathode modification layer and electron acceptor in efficient iPSCs, while demonstrating its applicability to large area, room temperature, all-solution processed fabrication techniques with slot-die coating.

In one aspect, the invention generally relates to a fullerene derivative having the structural formula:

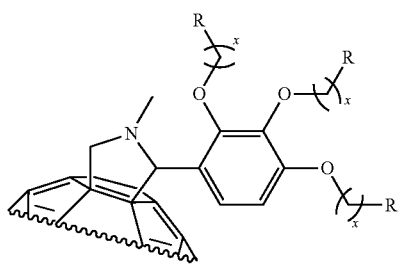

wherein
  R each is independently
    a neutral group selected from primary, secondary, tertiary amino groups, thiol group, phosphonate ester group, phosphoric acid group, or
    a zwitterionic group selected from sulfobetaine, carbocybetaine, phosphobetaine and phosphorylcholine groups; and
  x is an integer from 1 to 12.

In another aspect, the invention generally relates to a buffer or interlayer adaptable for use in an organic photovoltaic (OPV) device, comprising one or more fulleropyrrolidine derivatives with each of which bearing:
  one or more neutral groups selected from primary, secondary, tertiary amino groups, thiol group, phosphonate ester group, phosphoric acid groups, or
  one or more zwitterionic groups.

In yet another aspect, the invention generally relates to an OPV device comprising a buffer or interlayer disclosed herein.

In yet another aspect, the invention generally relates to a solar cell panel or assembly, which includes the OPV device disclosed herein.

BRIEF DESCRIPTION OF THE DRAWINGS

FIG. 38. Cross-section SEM image of the interface between the BHJ active layer and $C_{60}$-SB ETL.

FIG. 39. (A) Photograph of the mini slot-die coater; (B) Large area $C_{60}$-SB ETL coated on glass/ITO substrate; (C) slot-die processed devices; (D) I-V curve and the performance of the slot-die processed devices.

DESCRIPTION OF THE INVENTION

Figures 1A, 1B, 1C:
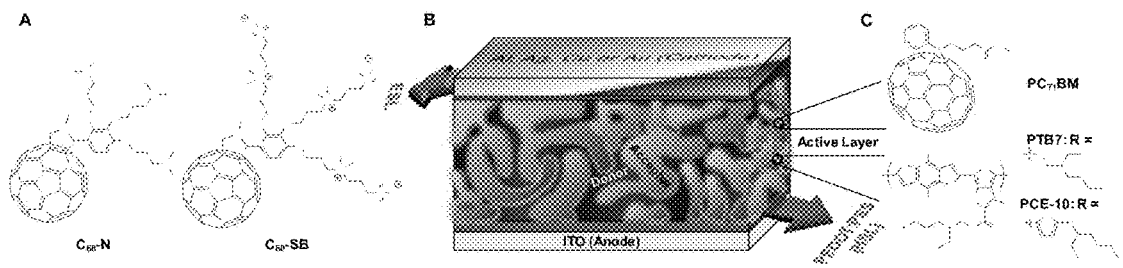
FIG. 1. Solar cell components and architecture. (A) Chemical structures of the two fulleropyrrolidines ($C_{60}$-N and $C_{60}$-SB) employed as cathode modification layers; (B) Device configuration, consisting of ITO/PEDOT:PSS/active layer/ESL/cathode, where PEDOT:PSS is the hole selective layer (HSL) and anode modifier, and Al, Ag, Cu or Au were used as the cathode; (C) Chemical structures of the compounds comprising the active layer, with PC$_{71}$BM as the acceptor and PTB7 or PCE-10 as the donor.

The invention provides novel materials, methods and designs to enable improved power conversion efficiencies of OPVs, especially novel approaches to interlayers for polymer-based solar cells. Novel functional fullerene-based interlayers are disclosed that enable high efficiency devices in conjunction with numerous active layer and electrode materials. For example, standard single-junction PSCs fabricated utilizing fulleropyrrolidines bearing terminal tertiary amine or sulfobetaine functionalities (e.g., $C_{60}$-N and $C_{60}$-SB) as buffer layers provided very high PCE values for such conventional devices, and unprecedented efficiency (9.78%) for Ag cathode devices. High PCEs (exceeding 8.5%) were obtained irrespective of the cathodes work-function, even for the high work function Au, indicating a universal utility of these interlayers.

Among the advantages of the invention are: (1) Novel functionalized carbon-based compounds (functional fullerenes) as efficient electron carriers; (2) Capabilities of generating high efficiencies from conventional device architecture (e.g., single junction conventional design rather than inverted or tandem types); (3) Enabling the use of Ag and other high work function metals as cathodes, which are advantageous over other typical electrodes such as aluminum due to stability. The use of Ag opens an opportunity to make an all-solution-processable device through the use of silver paste (slurry) in conjunction with the solution-processable organic/polymer components (active layer and interlayer); and (4) Improvements regarding thickness of the interlayer—the invention can tolerate thick (>50 nm) interlayers, which simplifies device fabrication.

The invention also allows dual utility of $C_{60}$-SB in acting as a thickness insensitive cathode modification layer and electron acceptor in efficient iPSCs, while demonstrating its applicability to large area, room temperature, all-solution processed fabrication techniques with slot-die coating.

In one aspect, the invention generally relates to a fullerene derivative having the structural formula:

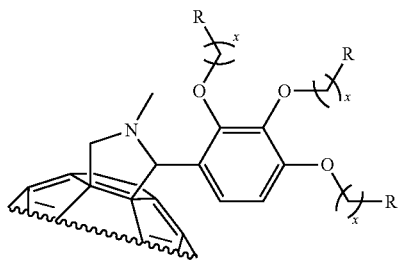

wherein
R each is independently
  a neutral group selected from primary, secondary, tertiary amino groups, thiol group, phosphonate ester group, phosphoric acid group, or
  a zwitterionic group selected from sulfobetaine, carbocybetaine, phosphobetaine and phosphorylcholine groups; and
x is an integer from 1 to 12.

The fullerene derivative may be based on any suitable fullerene compound, for example, the fullerene may be selected from $C_{60}$, $C_{70}$, $C_{76}$, $C_{82}$ and $C_{84}$. In certain preferred embodiments, the fullerene is $C_{60}$. In certain preferred embodiments, the fullerene is $C_{70}$.

The R groups may be selected to be all identical or not all identical. In certain embodiments, all R's are identical. In certain embodiments, all R's are not identical.

Exemplary R groups include the following and derivatives thereof:

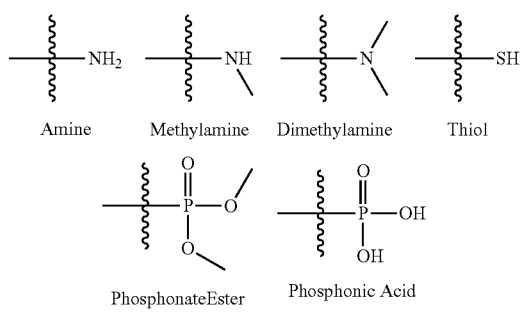

In certain embodiments, each R is a neutral group. In certain preferred embodiments, each R is an amino group selected from primary, secondary, and tertiary amino groups. In certain preferred embodiments, each R is a tertiary amino group.

In certain preferred embodiments, each R is a thiol group.

In certain embodiments, each R is a zwitterionic group selected from sulfobetaine, carbocybetaine, phosphobetaine and phosphorylcholine groups. In certain preferred embodiments, each R is a sulfobetaine group.

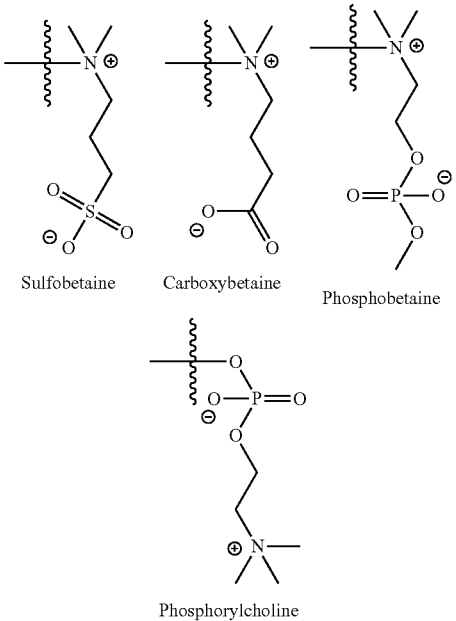

"x" may be any suitable number, for example, an integer from 1 to 12 (e.g., 1, 2, 3, 4, 5, 6, 7, 8, 9, 10, 11, 12). In certain preferred embodiments, x is an integer from 1 to 6. In certain preferred embodiments, x is an integer from 1 to 3.

Exemplary fullerene derivatives include the following and derivatives thereof:

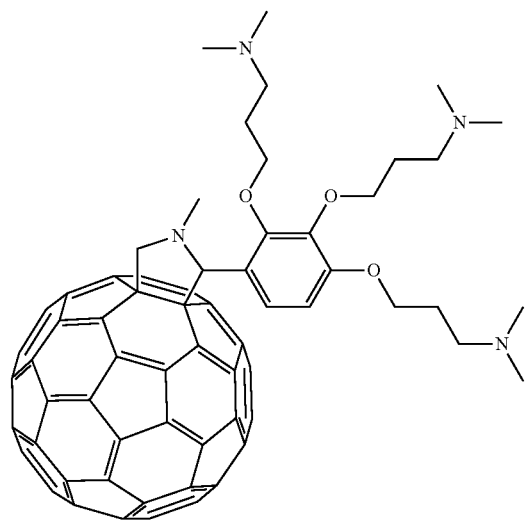

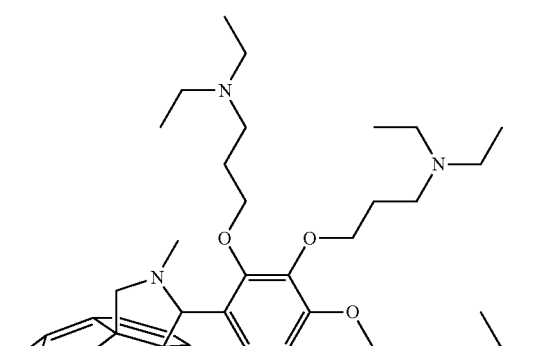

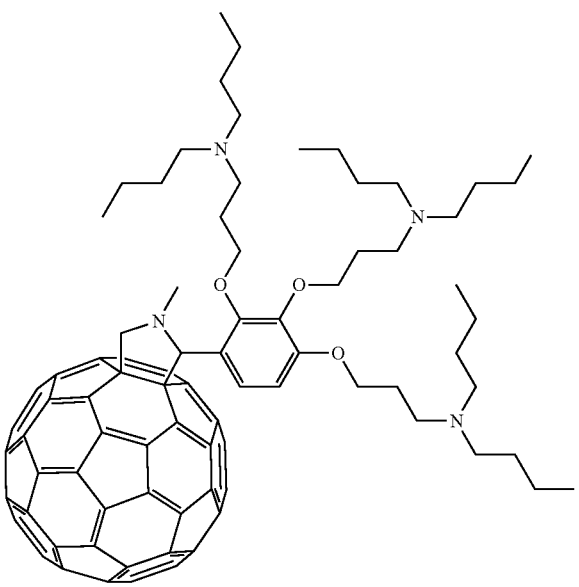

-continued
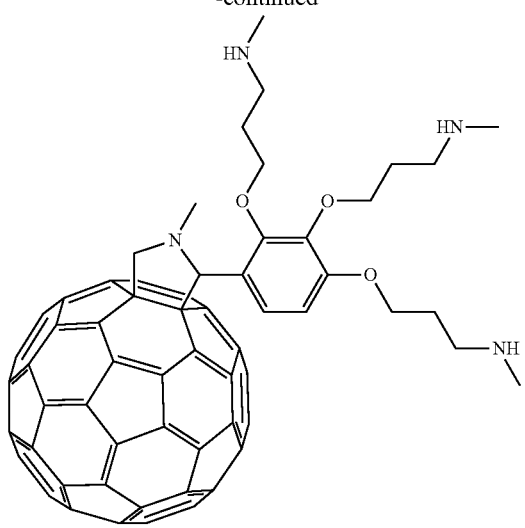
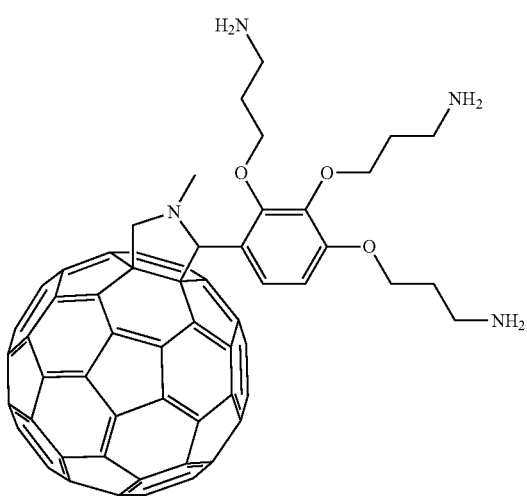
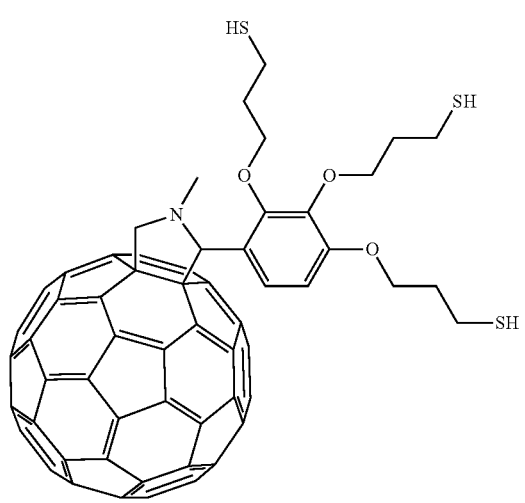
-continued
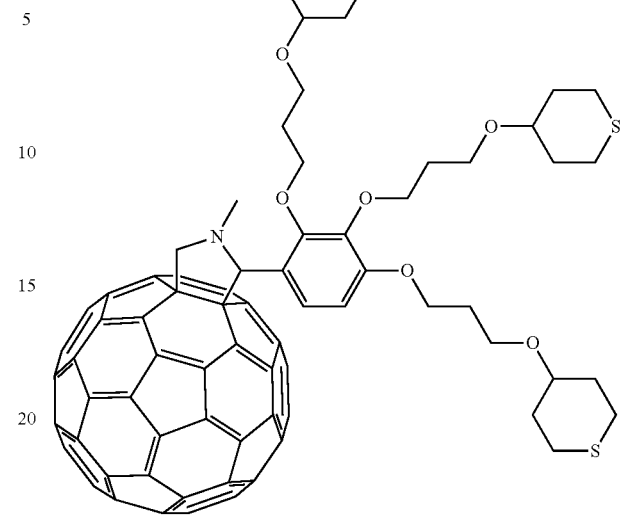
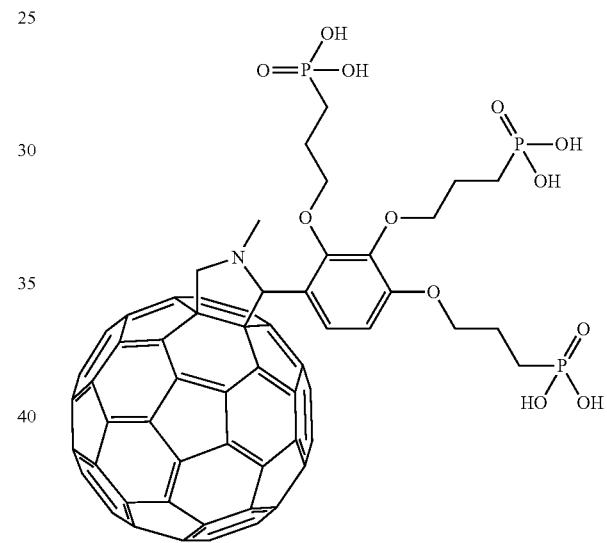
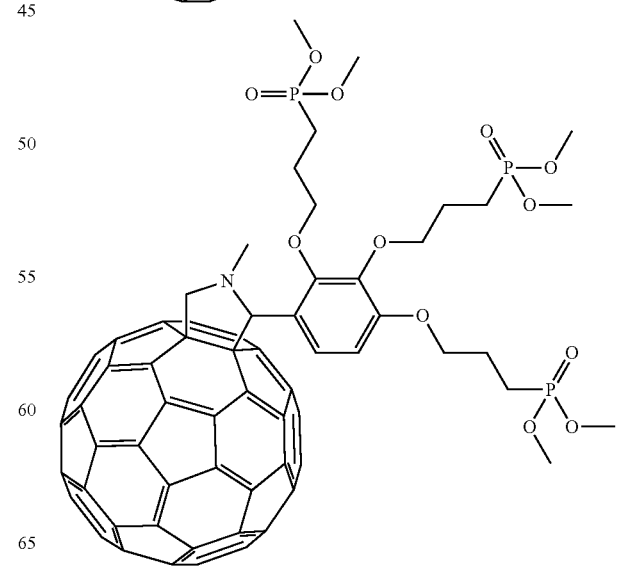

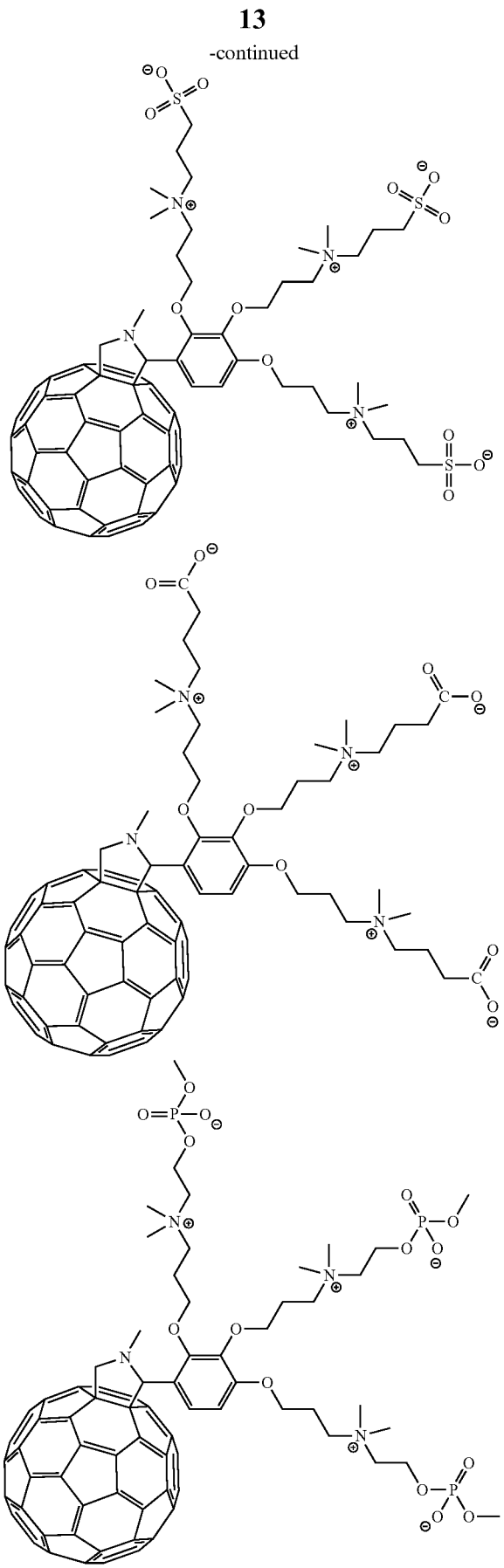

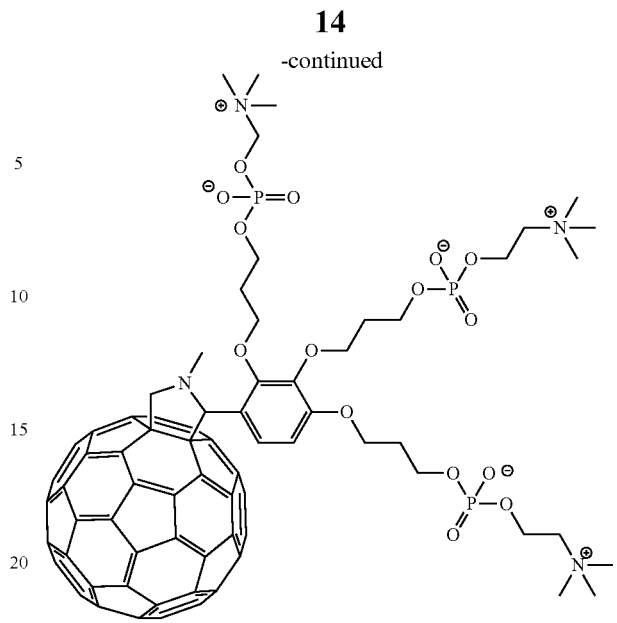

In another aspect, the invention generally relates to a buffer or interlayer adaptable for use in an OPV device, comprising one or more fulleropyrrolidine derivatives with each of which bearing:

one or more neutral groups selected from primary, secondary, tertiary amino groups, thiol group, phosphonate ester group, phosphoric acid groups, or one or more zwitterionic groups.

In certain embodiments, each of the one or more fulleropyrrolidine derivatives bears three or more (e.g., 3, 4, 5, 6) neutral groups or three or more (e.g., 3, 4, 5, 6) zwitterionic groups.

In certain embodiments, each of the one or more fulleropyrrolidine derivatives bears one or more terminal amino groups selected from primary amino, secondary amino and tertiary amino groups.

In certain embodiments, the one or more zwitterionic groups are selected from sulfobetaine, carbocybetaine, phosphobetaine and phosphorylcholine groups. In certain preferred embodiments, each of the one or more fulleropyrrolidine derivatives bears three or more terminal amino groups.

In certain embodiments, each of the one or more fulleropyrrolidine derivatives bears three or more zwitterionic groups. In certain preferred embodiments, the one or more zwitterionic groups are sulfobetaine groups.

The buffer or interlayer may include one fulleropyrrolidine derivative or two or more (e.g., 2, 3, 4) fulleropyrrolidine derivatives, for example, selected from $C_{60}$, $C_{70}$, $C_{76}$, $C_{82}$ and $C_{84}$.

In certain preferred embodiments, the fulleropyrrolidine derivative is selected from pyrrolidine derivatives of $C_{60}$ and $C_{70}$.

In certain preferred embodiments, the two or more fulleropyrrolidine derivatives are mixtures of pyrrolidine derivatives $C_{60}$ and $C_{70}$.

In yet another aspect, the invention generally relates to an OPV device comprising a buffer or interlayer disclosed herein.

In general, the OPV device of the invention is characterized by a power conversion efficiency (PCE) of 8% or greater (e.g., preferably a PCE of 8.5% or greater, more preferably a PCE of 9.0% or greater, even more preferably a PCE of 9.5% or greater).

In certain embodiments, the OPV device comprises a cathode of Al, Ag, Cu or Au. In certain preferred embodiments, the OPV device comprises an Ag cathode.

In certain embodiments, the OPV device is a PSC. The OPV device may be a regular (conventional) PSC or an iPSC.

In yet another aspect, the invention generally relates to a solar cell panel or assembly, which includes the OPV device disclosed herein.

In certain preferred embodiments of the iPSC disclosed herein, it may include one or more tris(sulfobetaine)-substituted fullerenes ($C_{60}$-SB) acting as both a (thickness insensitive) cathode modification layer and electron acceptor.

In certain embodiments, the fulleropyrrolidine derivative utilized with the OPV device has the structural formula of

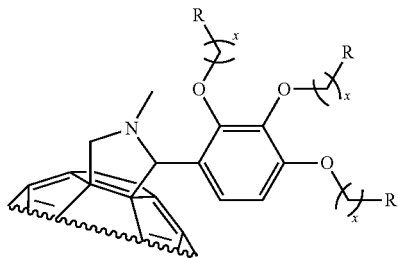

wherein

R each is independently a neutral group selected from primary, secondary, tertiary amino groups, thiol group, phosphonate ester group, phosphoric acid group, or a zwitterionic group selected from sulfobetaine, carbocybetaine, phosphobetaine and phosphorylcholine groups; and x is an integer from 1 to 12.

An ideal cathode design for OPVs might consist of a metal with a high intrinsic work function to benefit stability, but a readily tailored surface to lower its effective work function to benefit device performance. It is demonstrated that novel functionalized fullerenes bearing tertiary amine ($C_{60}$-N) or sulfobetaine ($C_{60}$-SB) groups are easy to process in solution, with excellent adhesion to the photoactive layer, and afford OPV devices with outstanding PCE values even when employing high work function metals as cathodes.

Disclosed herein are the synthesis, characterization and use of new trisubstituted polar fulleropyrrolidines as highly effective interlayer materials in polymer-based solar cells. The syntheses of tris(sulfobetaine)-substituted fullerene and its tris(dimethylamino)-substituted precursor, shown in Scheme 1, are rapid and efficient. PSCs utilizing this fullerene design in conjunction with Al, Ag, Cu and Au cathodes gave PCE values>8.5%. Two different active layer polymers, used in conjunction these fullerene interlayers, showed dramatically increased performance as a result of the interlayer. Ultraviolet photoelectron spectroscopy (UPS), charge mobility measurements, and reflectance spectroscopy provide insight to this observed efficiency enhancement.

Scheme 1. Synthesis of fullerene interlayer materials $C_{60}$-N and $C_{60}$-SB

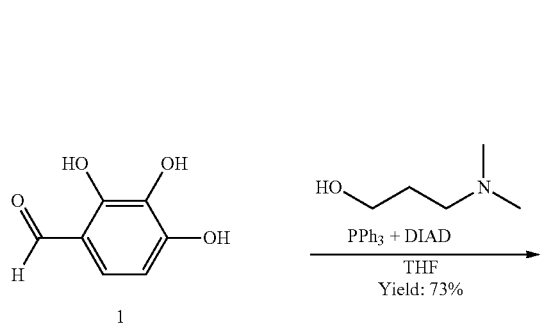

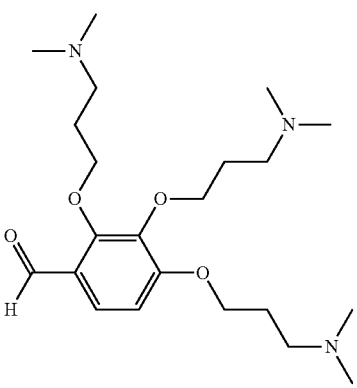

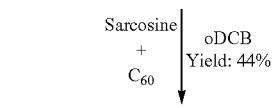

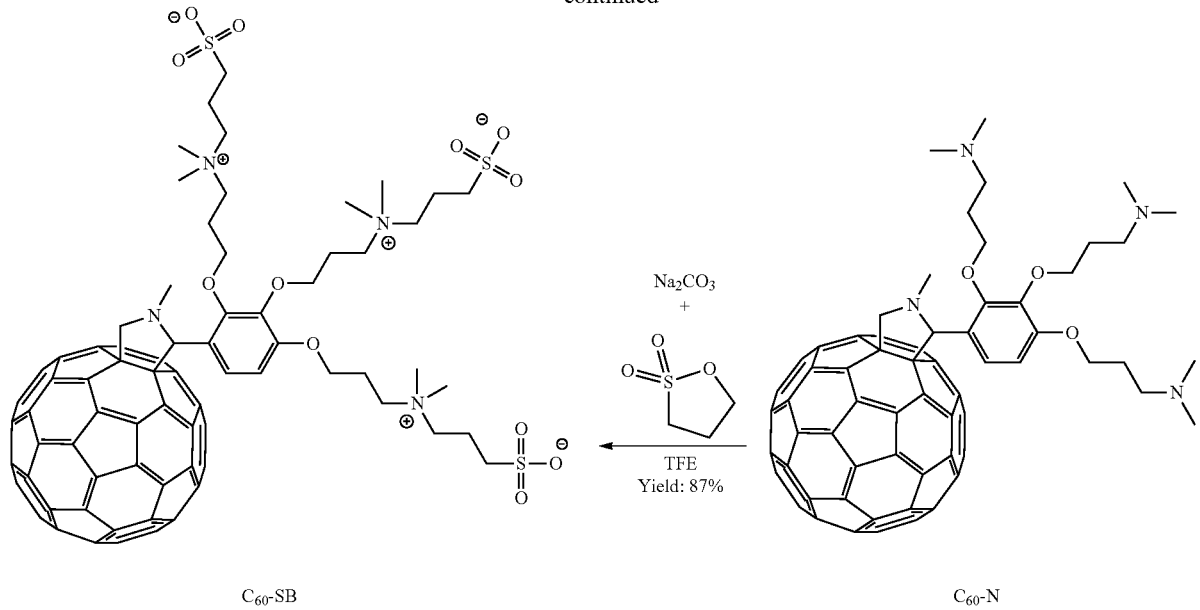

The amine ($C_{60}$-N) and sulfobetaine ($C_{60}$-SB)-substituted fullerenes were prepared by connection of the corresponding trisubstituted phenyl groups through a pyrrolidine ring (FIG. 1A, Scheme 1). For $C_{60}$-N, Mitsunobu coupling gave the trifunctional benzaldehyde bearing pendant amines, followed by a Prato reaction to connect the benzaldehyde to fullerene-$C_{60}$. $C_{60}$-N served as a precursor to $C_{60}$-SB, by use of the tertiary amines of $C_{60}$-N in ring-opening of 1,3-propanesultone. (Mitsunobu, et al. 1967 *Bull. Chem. Soc. Jpn.* 40, 2380-2382; Maggini, et al. 1993 *J. Am. Chem. Soc.* 115, 9798-9799; Prato, et al. 1998 *Acc. Chem. Res.* 31, 519-526.) These syntheses are rapid and efficienty, while precluding the need for methanofullerene derivatives prepared through unstable diazo intermediates. (Hummelen, et al. 1995 *J. Org. Chem.* 60, 532-538.)

Figure 13:
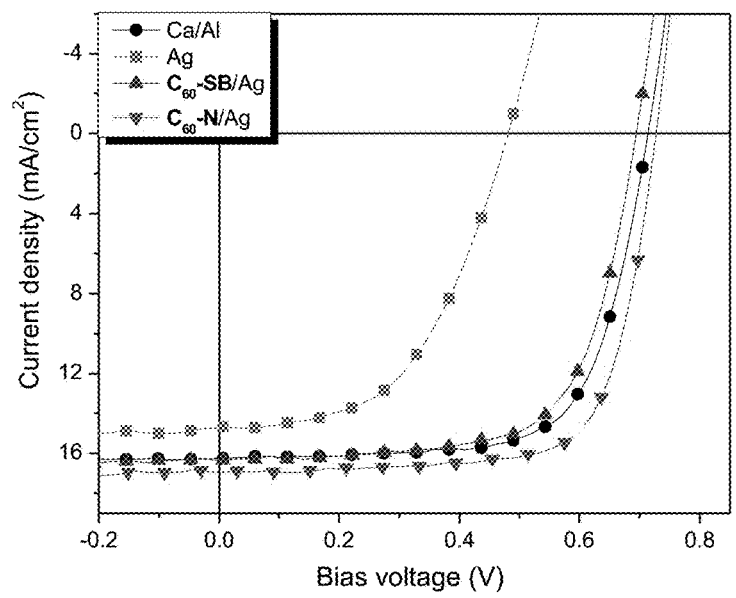
FIG. 13. PTB7-based OPV device performances given a general architecture of ITO/PEDOT:PSS/PTB7:PC$_{71}$BM/(C$_{60}$-N or C$_{60}$-SB)/cathode.
Figure 14:
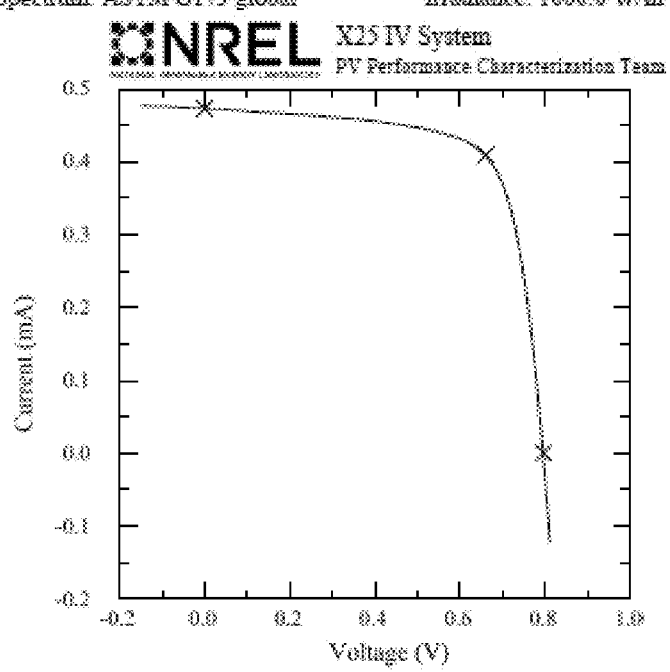
FIG. 14. NREL certified OPV device with an architecture of ITO/PEDOT:PSS/PCE-10:PC$_{71}$BM/C$_{60}$-N/Ag, resulting in a PCE of 8.91%.
Figure 15:
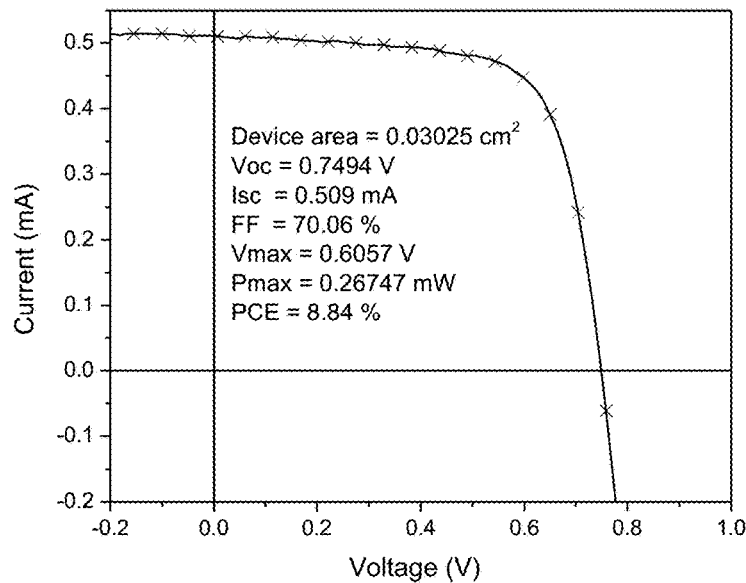
FIG. 15. J-V curve of the certified device after it was returned from NREL, showing good agreement of device metrics using the solar simulator. Optimization of fulleropyrrolidine synthesis and isolation and OPV device fabrication later resulted in a PCE$_{max}$ of 9.78% for devices with the same general architecture.

Single junction OPVs were fabricated with a BHJ active layer containing a blend of [6,6]-phenyl $C_{71}$-butyric acid methyl ester ($PC_{71}BM$) as the acceptor and a low bandgap conjugated polymer thieno[3,4-b]thiophene-a-benzodithiophene with either 2-(ethylhexyl)oxy (PTB7) or 2-(ethylhexyl)thienyl (PCE-10) side chains as the donor (FIGS. 1B and 1C) (data for PTB7 found in FIG. 13 and Table 1). (Liang, et al. 2010 *Adv. Mater.* 22, E135-E138.) In a device, $C_{60}$-N or $C_{60}$-SB was deposited by spin coating onto the active layer from trifluoroethanol (TFE), followed by deposition of the metal cathode (Al, Ag, Cu or Au). A device fabricated in this fashion, containing a Ag cathode, was examined and certified by the National Renewable Energy Laboratory (NREL) with a PCE of 8.91% (FIG. 14), identical to the efficiency obtained in our laboratories (FIG. 15).

Figure 2A:
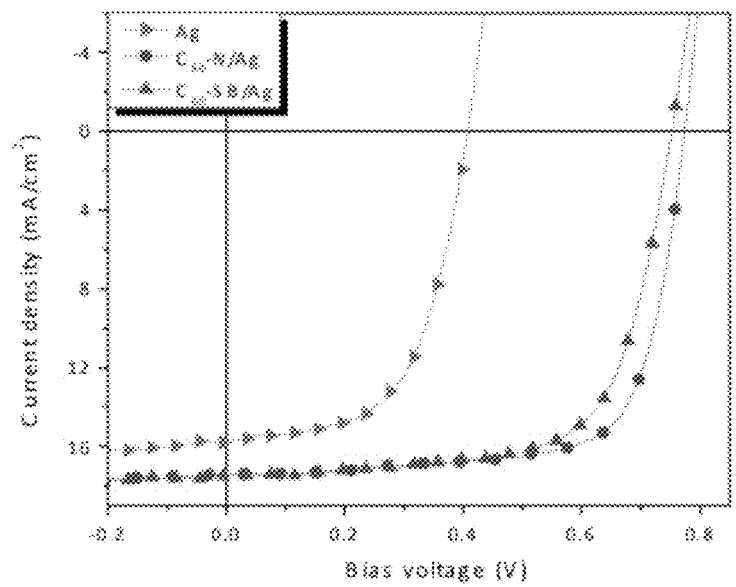
FIG. 2. OPV device performance for an ITO/PEDOT:PSS/PCE-10:PC$_{71}$BM/(fulleropyrrolidine)/cathode architecture. (A) Representative J-V curves for OPVs with bare Ag cathodes, and ~15 nm-thick C$_{60}$-N and C$_{60}$-SB interlayers; (B) Representative J-V curves showing the effect of cathode work function on V$_{OC}$ for the bare metal devices, and impact on OPVs containing a thin layer (~15 nm) of C$_{60}$-N between the active layer and top cathode; (C) Device metrics obtained at varying interlayer thickness (from ~5 to 55 nm).
Figure 2B:
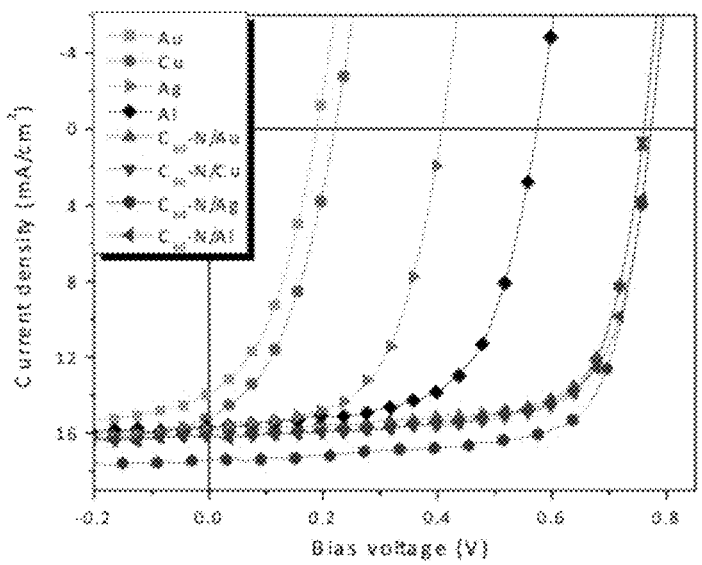

The PCE-10:$PC_{71}BM$ OPV devices fabricated with an Ag cathode were optimized further: whereas bare Ag control devices (no cathode modification layer) gave a PCE of 2.76±0.59% (maximum PCE 3.72%), devices with $C_{60}$-N or $C_{60}$-SB interlayers yielded PCE values of 9.35±0.13% (maximum PCE 9.78%) and 8.57±0.15% (maximum PCE 8.92%), respectively (FIG. 2A and Table 2). This large efficiency improvement stems from higher $V_{OC}$ and FF values, given in the associated plots. Devices with bare Ag cathodes suffer from the high work function of Ag that creates insufficient built-in electrostatic potential difference. FIG. 2A shows that devices fabricated with $C_{60}$-N interlayers outperform those with $C_{60}$-SB interlayers due to higher $V_{OC}$ (0.75-0.78 V) and FF (68-71%). Devices were also fabricated using a standard Ca/Al cathode, giving PCEs of 8.36±0.21% (Table 2). Comparable PCEs were obtained for devices with $C_{60}$-N/Al and $C_{60}$-SB/Al, with average PCEs of 8.65±0.11% and 8.29±0.11% respectively, thus eliminating the need for thermal deposition of Ca. (Grossiord, et al. 2012 *Org. Electron.* 13, 432-456.)

OPV devices fabricated with Cu or Au cathodes, omitting a cathode-modifying interlayer, had low PCEs of 1.29±0.06% and 0.99±0.05% respectively, as expected from

TABLE 1

Summarized photovoltaic performances for device architectures and compositions of ITO/PEDOT:PSS/PTB7:$PC_{71}BM$/(X)/Cathode*

| Cathode | Buffer Layer | $V_{OC}$ (V) | $J_{SC}$ (mA/cm$^2$) | FF (%) | PCE (%) |
|---|---|---|---|---|---|
| Al | Ca | 0.71 ± 0.006 | 15.71 ± 0.51 | 69.08 ± 0.93 | 7.72 ± 0.29 (8.05) |
| Ag | None | 0.47 ± 0.02 | 15.08 ± 0.64 | 50.21 ± 1.40 | 3.54 ± 0.32 (3.88) |
|  | $C_{60}$-SB | 0.70 ± 0.007 | 16.02 ± 0.34 | 66.68 ± 0.77 | 7.47 ± 0.12 (7.65) |
|  | $C_{60}$-N | 0.72 ± 0.004 | 16.37 ± 0.36 | 72.94 ± 0.61 | 8.59 ± 0.19 (8.96) |

*X is either Ca as a control, $C_{60}$-N, $C_{60}$-SB or not included (bare metal as control). Error represents ±1 standard deviation for averages obtained over six to eight devices and $PCE_{max}$ is given in parenthases.

the high □ values for Cu (4.7 eV) and Au (5.1 eV). (Tipler, P. A. and Llewellyn, R. A. Modern Physics, 3$^{rd}$ ed., W.H. Freeman, 1999.) However, by casting a ~15 nm thick layer of $C_{60}$-N onto the active layer prior to cathode deposition, the $V_{OC}$ recovered to 0.75 V for Cu and 0.76 V for Au, producing devices with PCE values of 8.67±0.17% ($PCE_{max}$=8.88%) and 8.56±0.21% ($PCE_{max}$=8.83%), respectively. The higher PCE values obtained for devices containing Ag cathodes over other metals is a direct result of higher $J_{SC}$: 16.83 mA/cm$^2$ for Ag, 16.01 mA/cm$^2$ for Cu, and 15.75 mA/cm$^2$ for Au. In addition, a large FF (≈70%) was obtained, independent of the metal cathode, underscoring the universal nature of $C_{60}$-N interlayers. These high work function metals have the important advantage of increasing device lifetime and, in the case of Ag, offer a pathway to all-solution-processing ultimately towards roll-to-roll techniques.

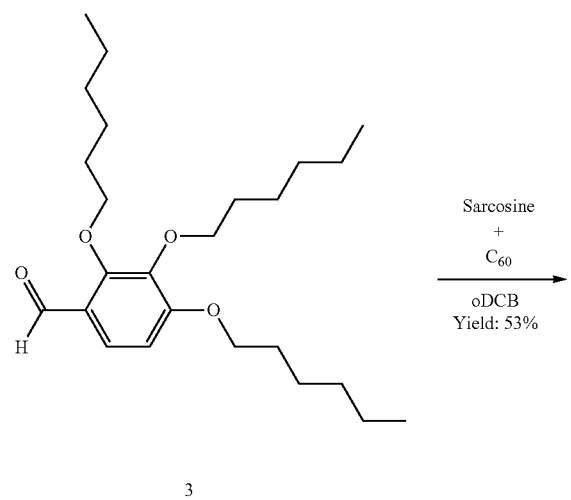

TABLE 2

Summarized photovoltaic performance of device architectures and compositions of ITO/PEDOT:PSS/PCE-10:PC$_{71}$BM/(X)/Cathode*

| Cathode | Buffer Layer | $V_{OC}$ (V) | $J_{SC}$ (mA/cm$^2$) | FF (%) | PCE (%) |
|---|---|---|---|---|---|
| Al | None | 0.56 ± 0.007 | 15.76 ± 0.17 | 63.11 ± 0.26 | 5.59 ± 0.05 (5.66) |
|  | Ca | 0.75 ± 0.01 | 15.88 ± 0.22 | 70.49 ± 0.45 | 8.36 ± 0.21 (8.71) |
|  | $C_{60}$-SB | 0.75 ± 0.007 | 16.42 ± 0.17 | 67.61 ± 1.04 | 8.29 ± 0.11 (8.44) |
|  | $C_{60}$-N | 0.76 ± 0.006 | 16.29 ± 0.08 | 69.71 ± 0.62 | 8.65 ± 0.11 (8.79) |
| Ag | None | 0.33 ± 0.04 | 15.30 ± 0.27 | 53.40 ± 3.45 | 2.76 ± 0.59 (3.72) |
|  | $C_{60}$-SB | 0.75 ± 0.005 | 16.89 ± 0.17 | 68.07 ± 0.30 | 8.57 ± 0.15 (8.92) |
|  | $C_{60}$-N | 0.78 ± 0.006 | 16.83 ± 0.21 | 71.35 ± 0.56 | 9.35 ± 0.13 (9.78) |
| Cu | None | 0.21 ± 0.007 | 15.25 ± 0.23 | 40.62 ± 0.63 | 1.29 ± 0.06 (1.38) |
|  | $C_{60}$-N | 0.75 ± 0.006 | 16.01 ± 0.30 | 71.91 ± 0.51 | 8.67 ± 0.17 (8.88) |
| Au | None | 0.18 ± 0.006 | 13.92 ± 0.10 | 40.21 ± 0.53 | 0.99 ± 0.05 (1.07) |
|  | $C_{60}$-N | 0.76 ± 0.007 | 15.75 ± 0.37 | 71.27 ± 0.64 | 8.56 ± 0.21 (8.83) |

*X is Ca, $C_{60}$-N, $C_{60}$-SB or no layer (i.e., bare metal). Al, Ag, Cu and Au were employed as cathodes. Error represents ±1 standard deviation for averages obtained over six devices; $PCE_{max}$ is given parenthetically.

Figure 2C:
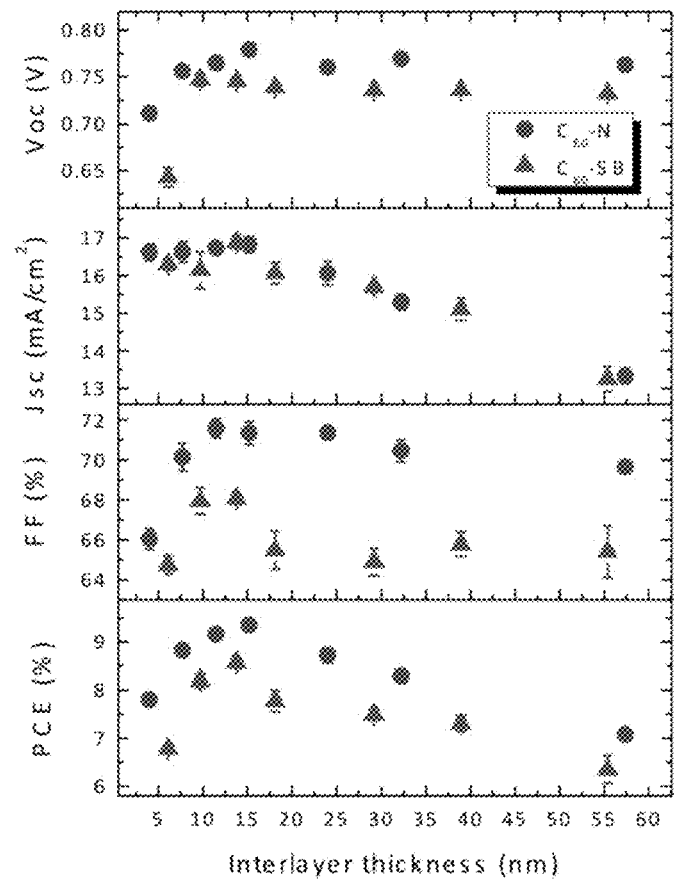
Figure 16:
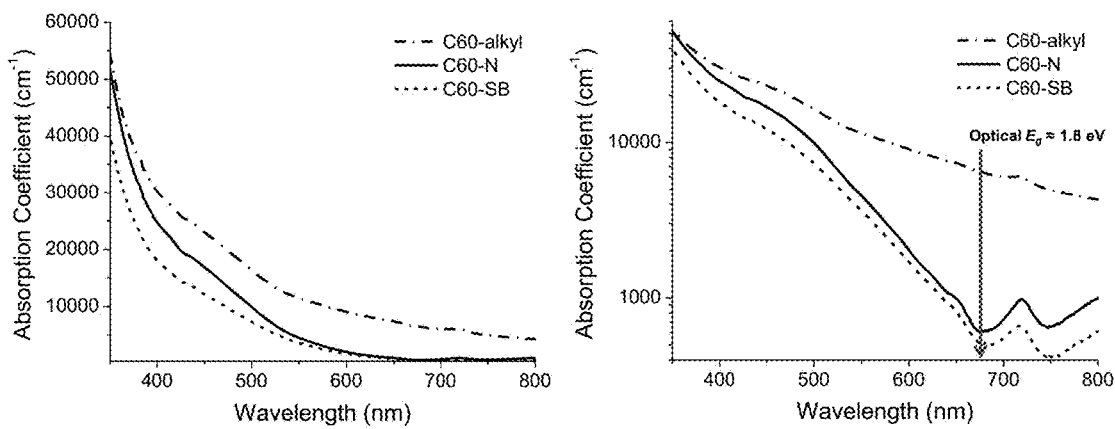
FIG. 16. UV-Vis absorption spectra of fulleropyrrolidines. Right spectra plotted against absorption coefficient as a logarithmic scale to help identify an approximate onset of absorption equal to 1.8 eV, which matches well with the difference in E$_A$ and I$_P$ energies obtained using CV and UPS respectively. Absorption coefficients were determined by casting three relatively thick films (~150 nm) onto clean glass substrates, measuring their absorption profiles with UV-Vis absorption spectroscopy, determining thickness using profilometry and taking the average values from both measurements as A (absorption, AU) and l (path length, cm) to determine the absorption or attenuation coefficient (α, cm$^{-1}$) using the Beer-Lambert law for films: α=A/l.
Figure 17:
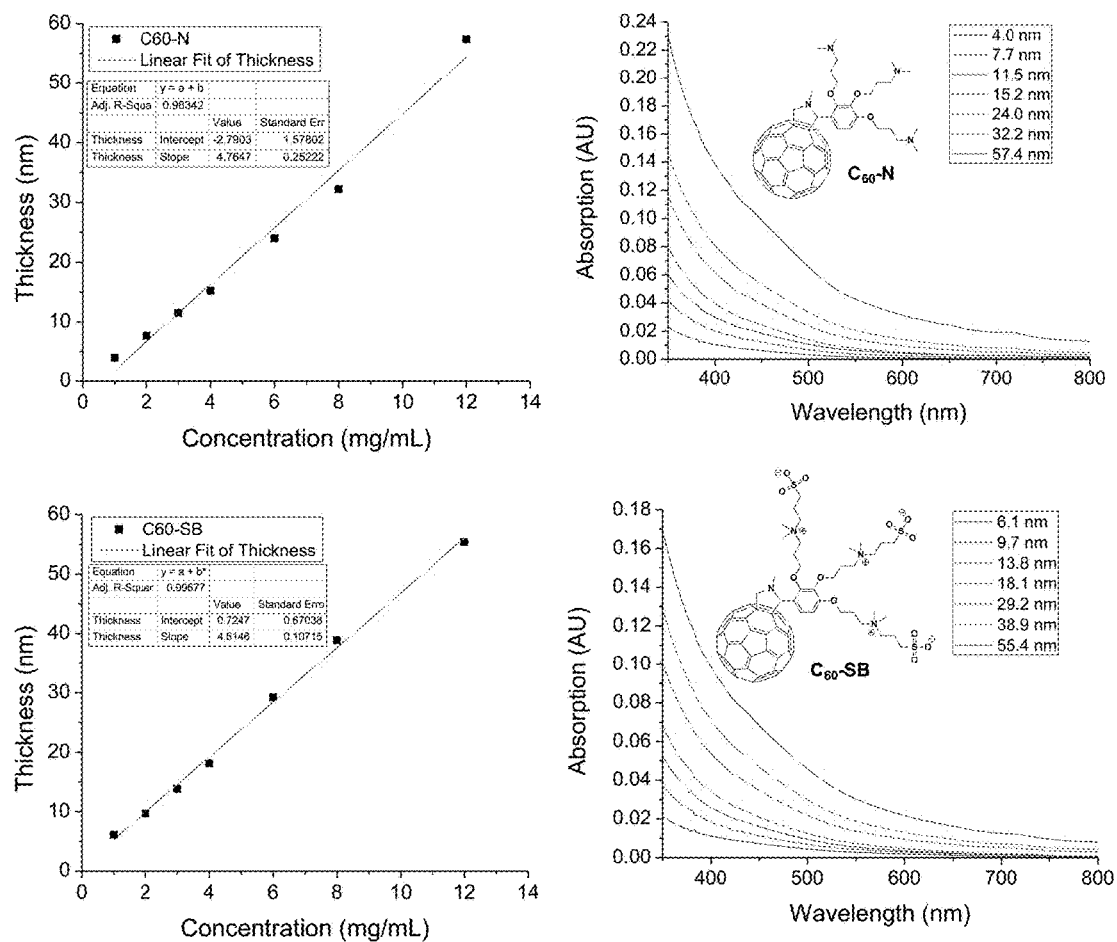
FIG. 17. Concentration vs. thickness profile for spun coat films on glass (left) and UV-Vis absorption (right) used to calculate thickness, using the Beer-Lambert law (l=A/α), given a predetermined attenuation coefficient (cm$^{-1}$) (discussed in FIG. 16).
Figure 18:
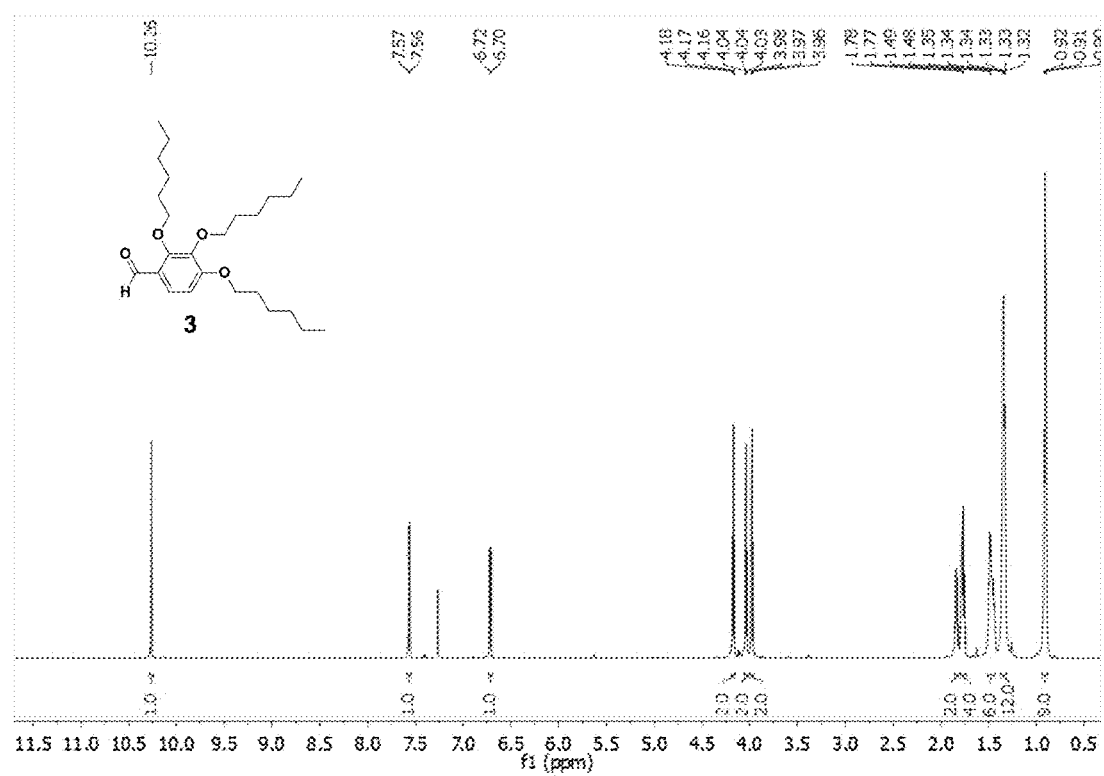
FIG. 18. $^1$H-NMR of compound 3 in CDCl$_3$.
Figure 19:
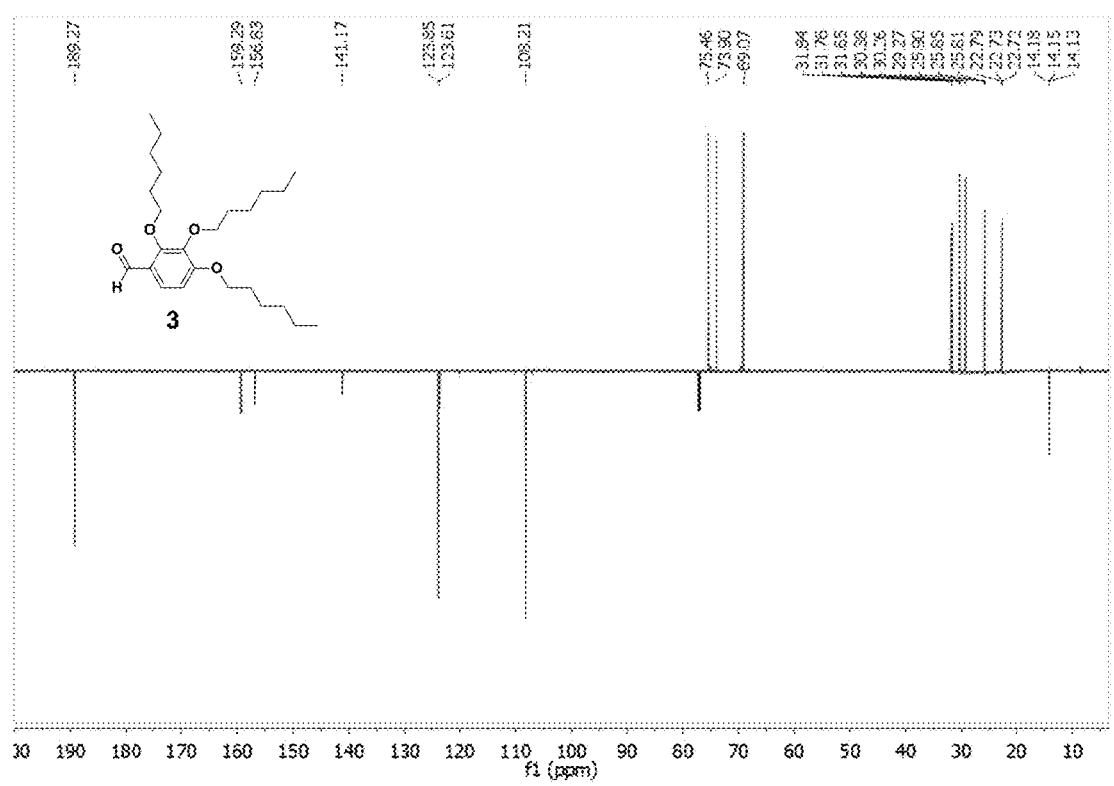
FIG. 19. $^{13}$C-NMR of compound 3 in CDCl$_3$, showing an overlay containing all hybridized carbons, including quaternary carbons in red (pointing down) with non-quaternary carbons in blue (CH & CH$_3$ pointing down, CH$_2$ pointing up).
Figure 20:
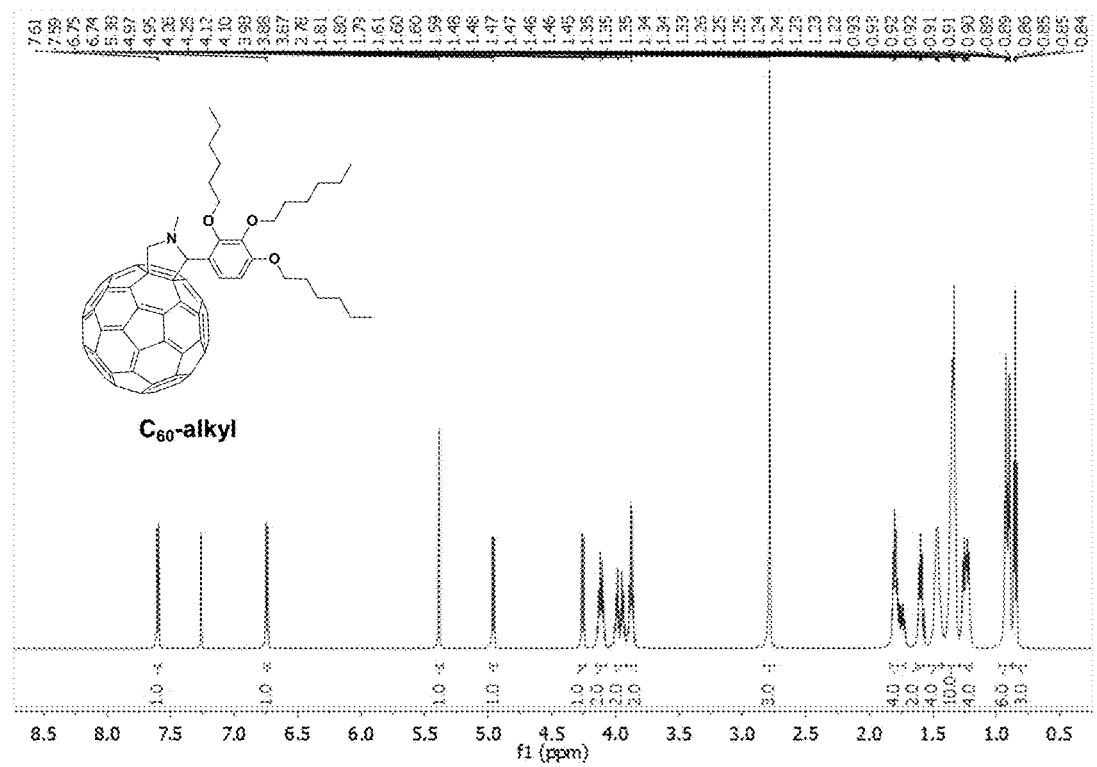
FIG. 20. $^1$H-NMR of C$_{60}$-alkyl in CDCl$_3$.
Figure 21:
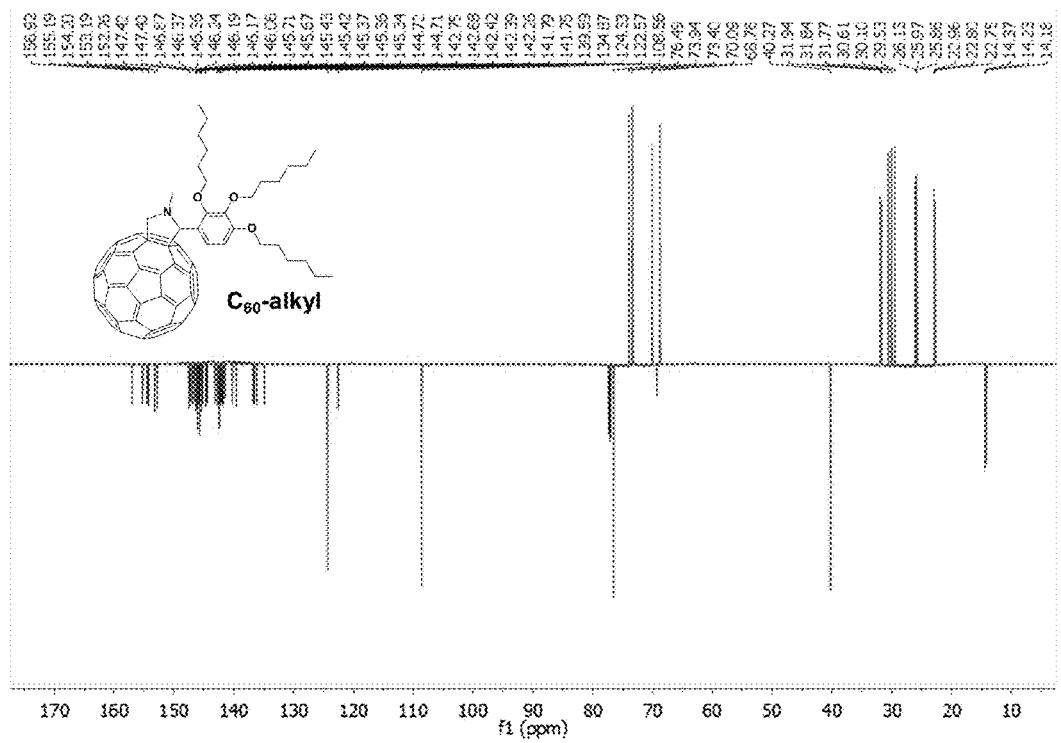
FIG. 21. $^{13}$C-NMR of compound C$_{60}$-alkyl in CDCl$_3$, showing an overlay containing all hybridized carbons, including quaternary carbons in red (pointing down) with non-quaternary carbons in blue (CH & CH$_3$ pointing down, CH$_2$ pointing up).
Figure 22:
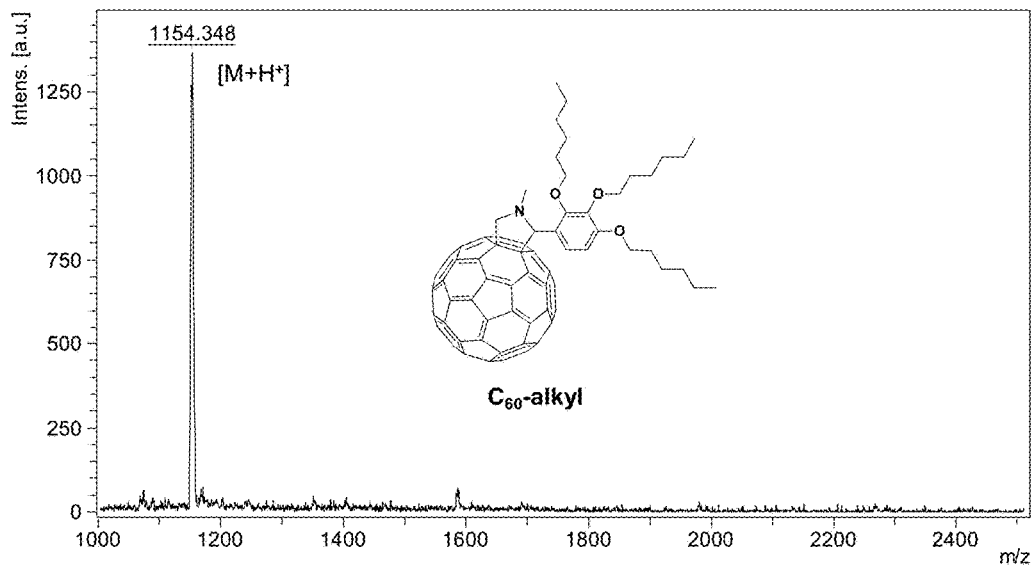
FIG. 22. MALDI-TOF mass spectrum of C$_{60}$-alkyl.

Seven different interlayer thicknesses were investigated over a range from 5 to 55 nm (FIG. 2C, FIGS. 16-17 and Table 3). Both $C_{60}$-N and $C_{60}$-SB produced devices with peak PCE at ~15 nm interlayer thickness. For $C_{60}$-N, $V_{OC}$ and FF plateaued at approximately 0.75 V and 70%, respectively, in accord with interlayer thickness, while $C_{60}$-SB devices maintained a constant $V_{OC}$ (≈0.75 V) and a slight decline in FF (from 68 to 65%) for films thicker than ~15 nm, and a decrease in $J_{SC}$ from ~17 mA/cm$^2$ (thickness≤15 nm) to ~13 mA/cm$^2$ (thickness~55 nm). Thus, these interlayers offer advantages over other interlayers, such as CPZs as previously reported, in which thickness must be controlled, since >10 nm layers result in S-shaped J-V curves and reduced PCE. (Liu, et al. 2013 *Adv. Mater.* 25, 6868-6873.) Unlike the CPZ interlayers, these fulleropyrrolidine interlayers afford efficient devices even at thicknesses exceeding 50 nm.

Scheme 2. Synthesis of $C_{60}$-alkyl

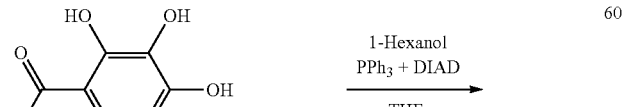

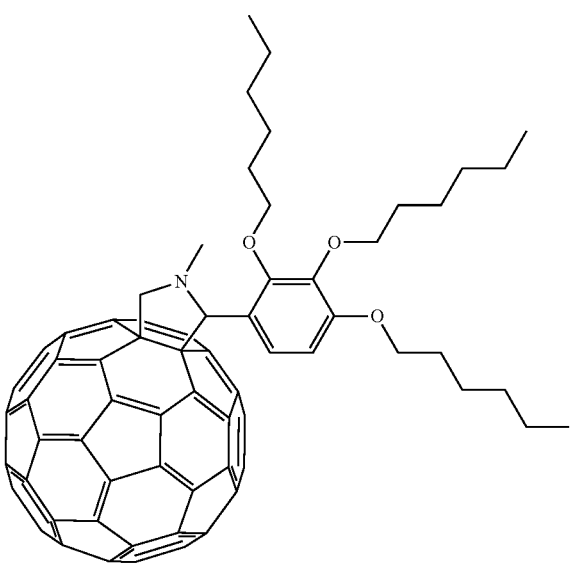

$C_{60}$-alkyl

TABLE 3

Average thicknesses and standard deviations*
Device Architecture: ITO/PEDOT:PSS/PCE-10:PC$_{71}$BM/(C$_{60}$-N)/Ag

|  | Control (bare Ag) | 4 mg/mL C$_{60}$-N | 8 mg/mL C$_{60}$-N | 12 mg/mL C$_{60}$-N |
|---|---|---|---|---|
| Average Thickness (nm) | 128.7 | 145.7 | 162.0 | 183.3 |
| Standard Deviation (nm) | 3.3 | 4.9 | 6.1 | 5.6 |
| Thickness of C60-N (nm) | 0.0 | 17.0 | 33.2 | 54.6 |

*Determined directly from OPV devices containing either no interlayer (bare Ag control) or C$_{60}$-N spun from TFE at 40000 rpm onto the active layer at the concentrations noted (4 mg/mL, 8 mg/mL and 12 mg/mL). The data was obtained by removing a thin layer of material using a razor blade, followed by at least 10 measurements around the active device area. Measurements were done between the Ag cathodes, such that the thickness data includes the following layers (where PEDOT:PSS was measured to be ~30 nm thick): PEDOT:PSS/PCE-10:PC$_{71}$BM/(C$_{60}$-N). The thickness of the interlayer was then calculated by taking the difference between the average control thickness (no interlayer) and measured thicknesses for devices containing interlayers. The results match well with those obtained using UV-Vis absorption spectroscopy.

Figure 3A:
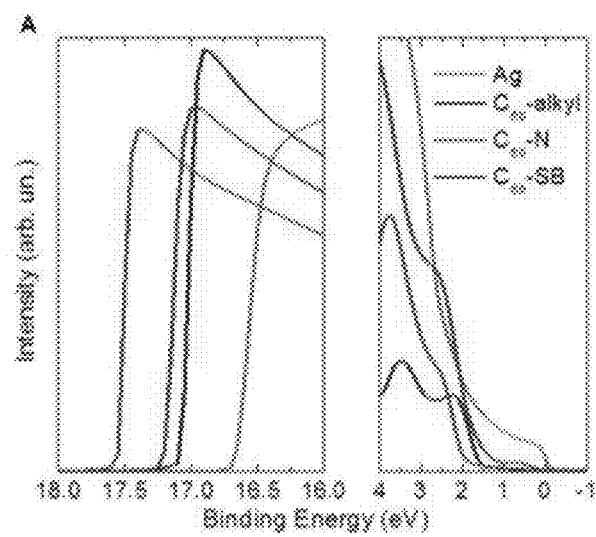
FIG. 3. (A) UPS of C$_{60}$-alkyl, C$_{60}$-N and C$_{60}$-SB (~15 nm layers) on metal substrates, showing the high and low binding energy regions of C$_{60}$-N and C$_{60}$-SB on Ag and of bare Ag used to determine Δ, I$_P$ and E$_F$. The high binding energy region near the E$_{SEC}$ shows that C$_{60}$-N provides a larger Δ on Ag, −0.83 eV than C$_{60}$-SB, −0.51 eV and C$_{60}$-alkyl, −0.37 eV. The low binding energy region provides the I$_P$ for C$_{60}$-alkyl, C$_{60}$-N and C$_{60}$-SB, giving 5.70 eV, 5.62 eV and 5.72 eV respectively. (B) Representative high binding energy region for C$_{60}$-N films on freshly prepared Ag, Cu and Au substrates that pins the work function of each modified metal surface at ~3.9 eV or ~3.65 eV for 1 nm and 15 nm films, respectively. (C) Work function modification of Ag, Cu and Au with C$_{60}$-N films of various thickness. Pinning of the effective work function pinning occurs is seen for very thin films (nominally 1 nm), and large modification of metal work function (to 3.65 eV) is achieved at film thickness>4 nm.
Figure 23:
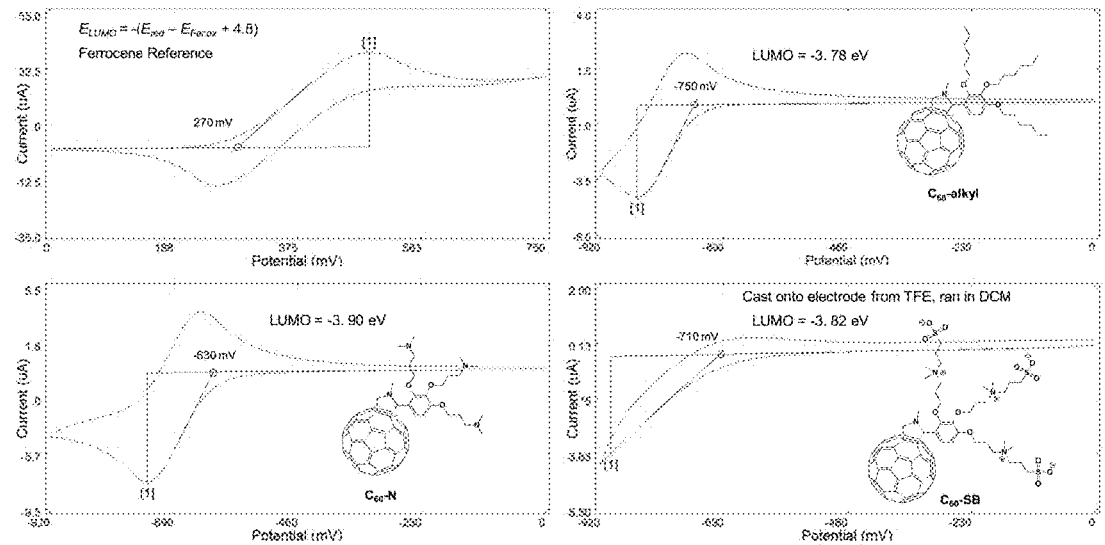
FIG. 23. CV of fulleropyrrolidines used to determine LUMO energy (=−E$_A$) from the reduction onset, using the equation given in the top right corner of the ferrocene reference. C60-SB was cast from solution directly onto the working electrode.

The interactions of C$_{60}$-N and C$_{60}$-SB interlayers with metal surfaces were investigated and compared to interlayers from 2,3,4-tris(hexyloxy)fulleropyrrolidine (C$_{60}$-alkyl) lacking the amine or sulfobetaine functionality (Scheme 2 and FIGS. 18-22). The three fullerenes had similar optoelectronic properties, with UV absorption onset indicating optical band gaps (E$_g$) of approximately 1.8 eV for each (FIG. 17), and cyclic voltammetry (CV) giving electron affinity (E$_A$) values of 3.8-3.9 eV from the onset of reduction (FIG. 23). The high and low binding energy onsets in UPS showed that the ionization potential (I$_P$) for the fulleropyrrolidines ranged from 5.6-5.7 eV (FIG. 3A). E$_g$ values calculated from the difference between E$_A$ and I$_P$ correlated closely to the E$_g$ values determined by UV-Vis absorbance spectroscopy (~1.8±0.1 eV). The similar E$_A$ values of these fullerenes with that of PC$_{71}$BM suggests that there is little-to-no energy barrier for electron transfer at the interface of PC$_{71}$BM with fulleropyrrolidine interlayers. An appreciable energy barrier in these fulleropyrrolidine interlayers that would reduce FF due to interfacial charge build-up was not observed even at >15 nm thickness; as such, these substituted fullerene combine the benefits of electronic transport with polar, surface interacting functionality for improved device performance.

The high binding energy region of the UPS spectra provides interfacial dipole (Δ) values that reflect difference in the high binding energy onset, or E$_{SEC}$, of a bare vs coated metal substrate. UPS characterization of C$_{60}$-N, C$_{60}$-SB and C$_{60}$-alkyl on freshly prepared Ag substrates revealed C$_{60}$-N to have the largest Δ value, −0.83±0.02 eV (FIG. 3A), which remained constant for films thicker than 8 nm, and was found to decrease for very thin films (in accord with the reduced V$_{OC}$ for those devices, Table 4).

The larger Δ for C$_{60}$-N relative to C$_{60}$-SB accounts for the higher V$_{OC}$ in those devices. A larger Δ value increases the built-in electrostatic potential difference in the device, improving charge extraction and reducing the recombination losses, which explains the higher J$_{SC}$ and FF values for devices with C$_{60}$-N relative to C$_{60}$-SB. The difference in work function of the electrodes coated with C$_{60}$-alkyl and C$_{60}$-SB (0.14 eV) arises from a permanent dipole effect due to interaction of zwitterionic sulfobetaine groups with metal surfaces, while the larger Δ for C$_{60}$-N is likely due to electron transfer from the tertiary amines to the metal substrate, a mechanism not available to the sulfobetaine zwitterions. (Liu, et al. 2013 *Adv. Mater.* 25, 6868-6873; Bröker, et al. 2008 *Appl. Phys. Lett.* 93, 243303; Lindell, et al. 2008 *Appl. Phys. Lett.* 92, 163302; Lindell, et al. 2006 *Chem. Mater.* 18, 4246-4252.)

Figure 3B:
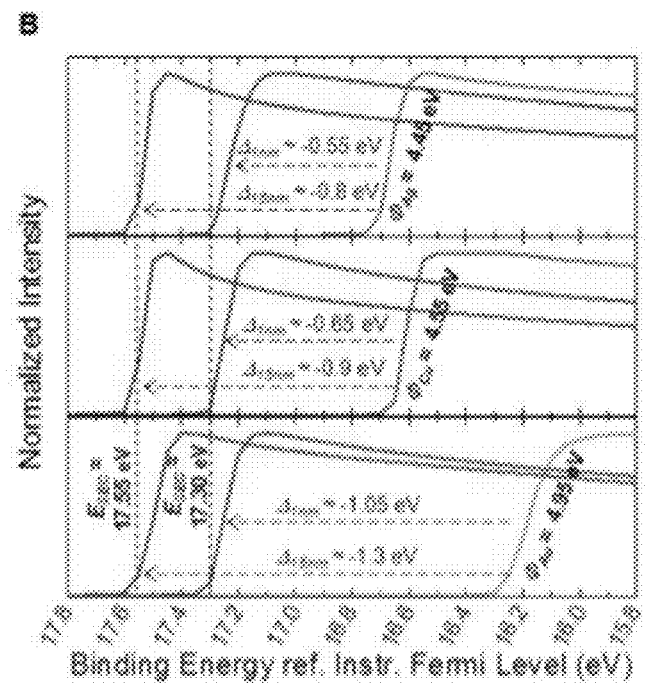
Figure 3C:
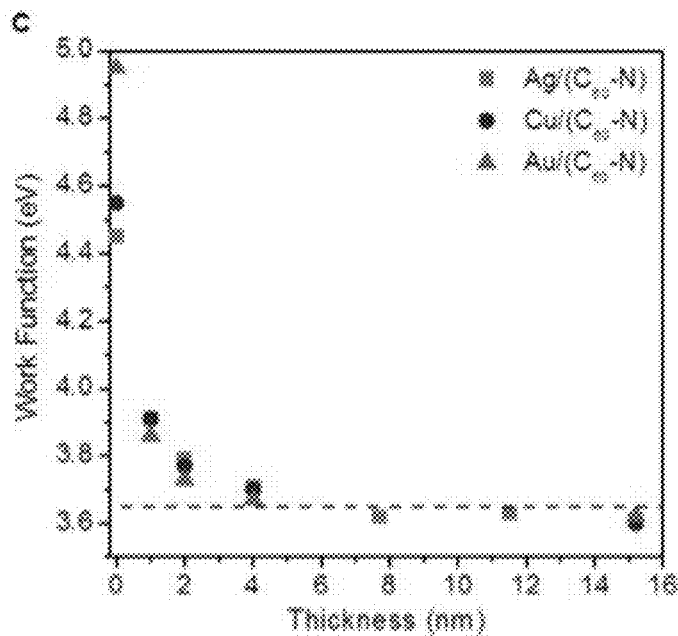

The magnitude of Δ for C$_{60}$-N films on metal substrates exhibited a distinct dependence on film thickness (FIG. 3B). However, for ultrathin films (1 nm nominal thickness) of C$_{60}$-N on Ag, Cu or Au substrates, the effective work function was already "pinned", independent of the metal composition, at 3.9 eV. Observing this effect for such thin films indicates that pinning originates at the metal/C$_{60}$-N interface, though the exact mechanism of this interaction (specific chemisorption/physisorption interactions and associated modification of the electron density tail at the metal surface) is not understood fully. (Braun, et al. 2009 *Adv. Mater.* 21, 1450-1472.) With increasing C$_{60}$-N thickness, work function values saturated at 3.65 eV on Ag, Cu or Au (FIG. 3C). Such a gradual change of Δ within ~5 nm of the interface indicates a narrow space charge region in C$_{60}$-N films, similar to a depletion region at the metal/doped semiconductor interface. The formation of a positive space charge in C$_{60}$-N is consistent with the electron transfer from tertiary amines to the metal substrate. (Bröker, et al. 2008 *Appl. Phys. Lett.* 93, 243303; Lindell, et al. 2008 *Appl. Phys. Lett.* 92, 163302; Lindell, et al. 2006 *Chem. Mater.* 18, 4246-4252.)

Using the expression for a depletion layer width $$w = \sqrt{\frac{2\varepsilon_r \varepsilon_0 V_{bi}}{qN_D}},$$

where V$_{bi}$ (=Δ) is the built-in potential, q is the elementary charge, $\varepsilon_0$=8.85×10$^{-12}$ F/m, $\varepsilon_r$ (=5) is the dielectric constant, and w=5 nm, the density of positive charges N$_D$ can be estimated at 1×10$^{19}$ cm$^{-3}$. Taking the volume of a single C$_{60}$-N molecule as ~1 nm$^3$, approximately 1 in 300 amines in the layer participates in electron donation to the metal. This effect is independent of the metal substrate, yielding an effective work function of 3.65 eV for C$_{60}$-N-modified Ag, Cu and Au electrodes (FIG. 3C). This suggests that C$_{60}$-N provides Ohmic contact for electron injection as well as

TABLE 4

UPS of C$_{60}$-N on Ag, varying fullerene thickness*
C$_{60}$-N on Ag

| | Thickness (nm) = | | | | | |
|---|---|---|---|---|---|---|
| | 4.0 | 7.7 | 11.5 | 15.2 | 24.0 | 32.2 |
| Δ$_{Ag}$ (eV) | −0.74 ± 0.01 | −0.83 ± 0.02 | −0.82 ± 0.03 | −0.84 ± 0.02 | −0.85 ± 0.01 | −0.84 ± 0.01 |
| I$_P$ (eV) | 5.65 | 5.62 | 5.64 | 5.62 | 5.62 | 5.63 |

*Interfacial dipole increases by approximately 0.1 eV when going from 4.0 nm to 7.7 nm, but plateaus past this thickness, giving an interfacial dipole around −0.83 eV. This result agrees with the lower V$_{OC}$ obtained for OPV devices fabricated with a ~4 nm interlayer thickness of C$_{60}$-N, compared to those fabricated with thicker films.

large built-in electrostatic potential difference for effective charge extraction in OPVs. The effect of these fullerenes on different metals confirms the general utility of these interfacial layer materials, and successful interfacial tailoring independent of electrode work function.

Figure 4A:
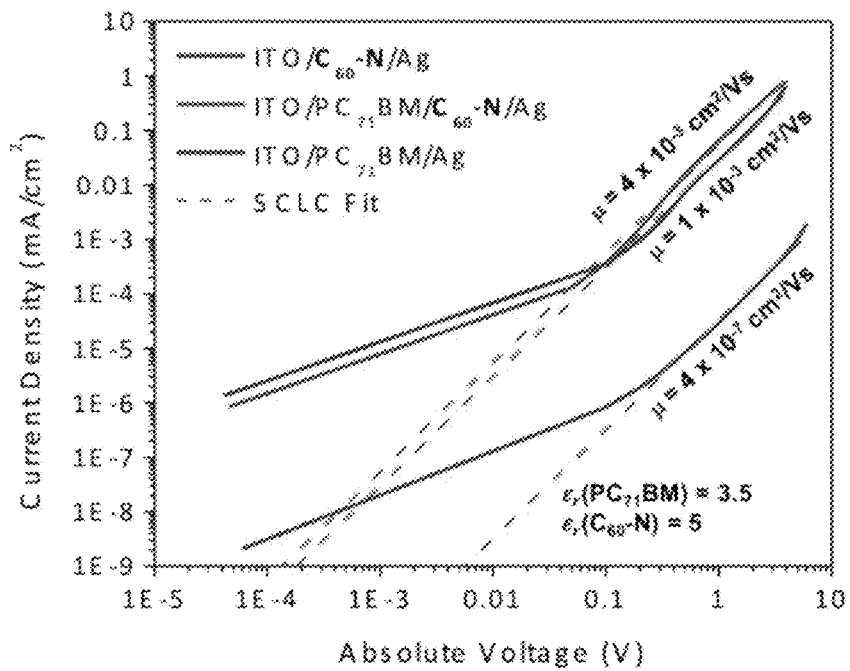
FIG. 4. (A) Representative J-V curves for electron-only devices with PC$_{71}$BM, PC$_{71}$BM/C$_{60}$-N and C$_{60}$-N layers in-between ITO and Ag electrodes, revealing that C$_{60}$-N removes the barrier for electron injection from Ag into the bulk organic layer, forming Ohmic contact. The dashed lines show fits to the Mott-Gurney law in the range of a space charge limited current regime of device operation. (B) UV-Vis reflectance spectroscopy of OPV devices varying C$_{60}$-N interlayer thickness from 4 to 57 nm (with no interlayer as a control). The increased reflectance from 600 to 740 nm for devices containing interlayers thicker than 7.7 nm is direct evidence of an "optical spacer" effect, which explains the reduced J$_{SC}$ for OPV devices with thicker interlayers.
Figure 24:
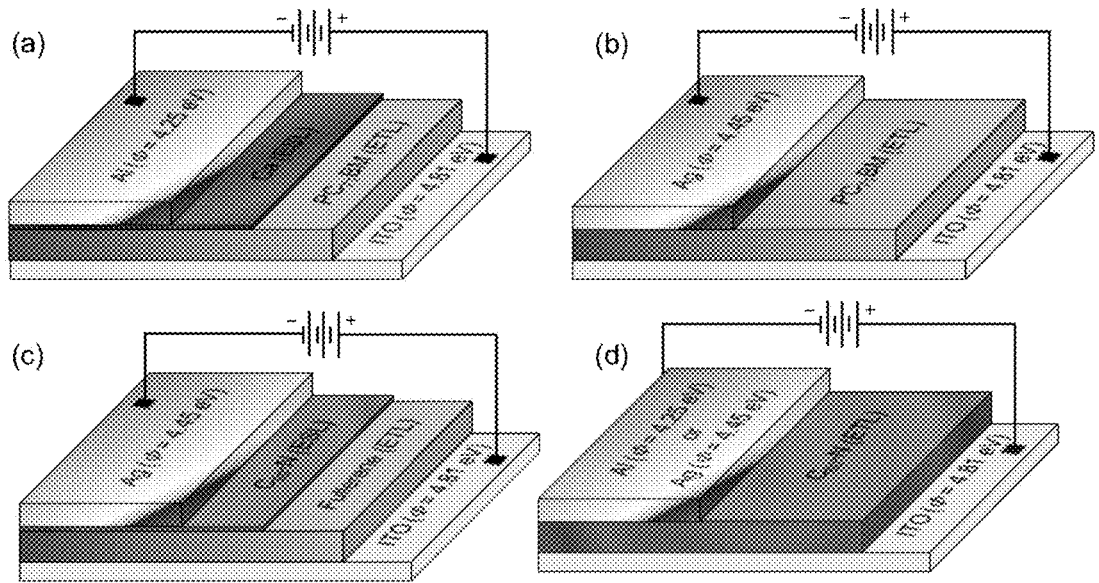
FIG. 24. Representative device architectures used for SCLC. (a) ITO/PC$_{71}$BM/Ca/Al architecture used to measure charge mobility of PC$_{71}$BM, applying a negative potential to Al; (b) ITO/PC$_{71}$BM/Ag architecture used to show the effect of a Schottky barrier from electron injection from Ag into PC$_{71}$BM, which reduces the estimated mobility measured due to enhanced resistance to injection at the Ag/PC$_{71}$BM interface (negative bias applied to Ag); (c) ITO/PC71BM/C$_{60}$-N/Ag architecture used to show how placing C$_{60}$-N between Ag and PC$_{71}$BM removes the barrier to injection, creating an Ohmic contact, represented by the mobility equal (or slightly greater than) that measured using the configuration shown in FIG. 24a; (d) ITO/C$_{60}$-N/Ag architecture used to show that electron injection into bulk C$_{60}$-N is not hindered when using a higher work function metal such as Ag (mobility is equal to or greater than the case where Ca/Al is used), due to the Ohmic contact created.
Figure 25:
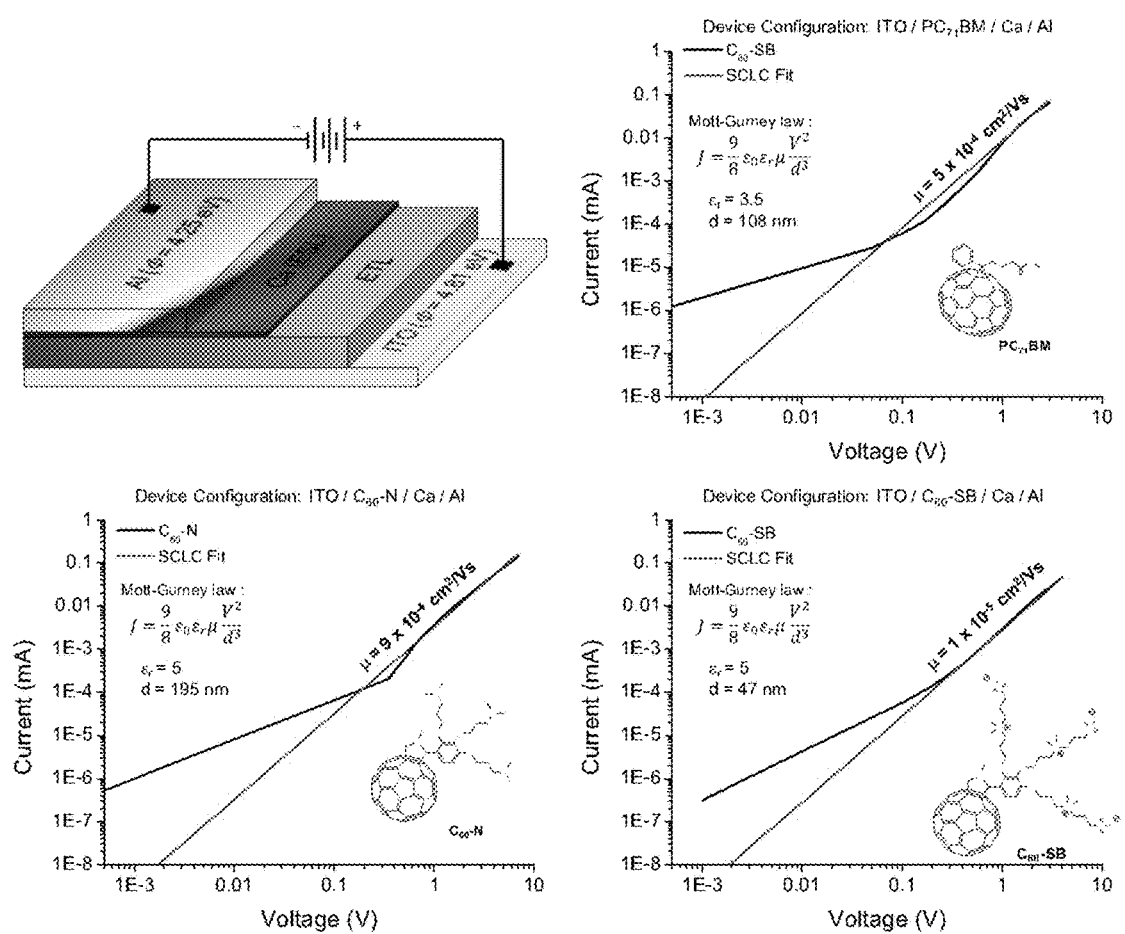
FIG. 25. Representative I-V curves for diodes with the architecture of ITO/(PC$_{71}$BM or C$_{60}$-N or C$_{60}$-SB)/Ca/Al for estimation of electron mobilities using an SCLC model.
Figure 26:
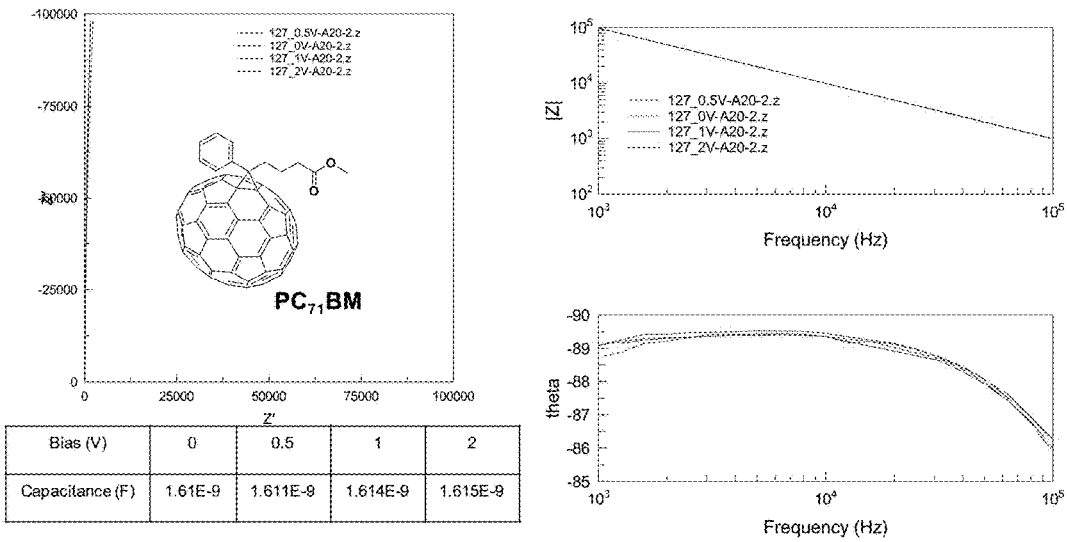
FIG. 26. Representative impedance spectra using the device architecture of ITO/PEDOT:PSS/PC$_{71}$BM/Al, used to make a capacitor as evidence by theta values approaching 90 over a wide range frequency range. Capacitance is shown to be independent of applied bias. The DC potential was applied to the Al electrode, the thickness of the fullerene used was 124 nm (as measured with proflometry) and the AC amplitude used was 20 mV. Used to estimate the dielectric constant from the equation $C=\varepsilon_r\varepsilon_o A/d$, where C, A, and d are the measured capacitance, the active area of device, and the film thickness, respectively.
Figure 27:
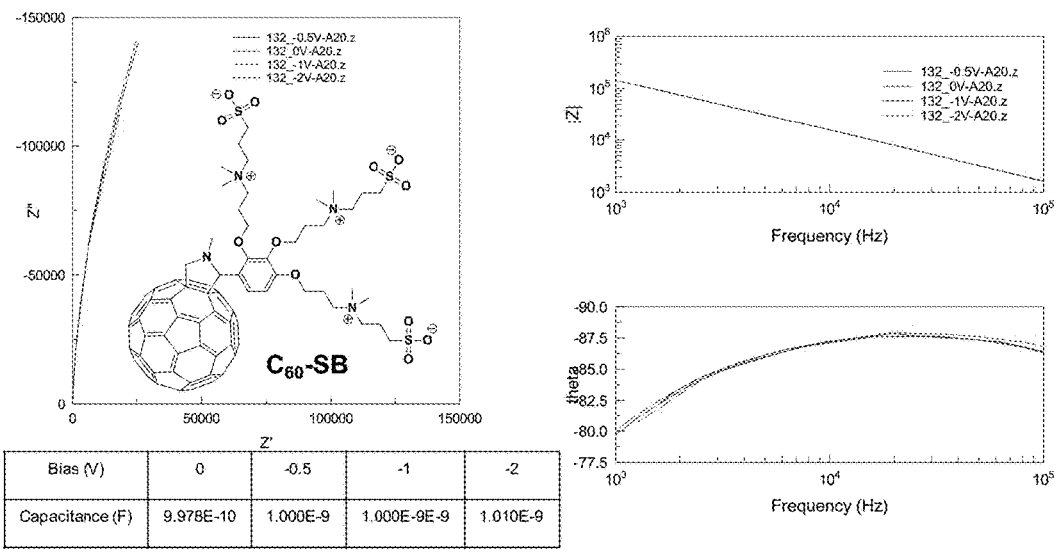
FIG. 27. Representative impedance spectra using the device architecture of ITO/PEDOT:PSS/$C_{60}$-SB/Al, used to make a capacitor as evidence by theta values approaching 90 over a wide range frequency range. Capacitance is shown to be independent of applied bias. The DC potential was applied to the ITO electrode, the thickness of the fullerene used was 257 nm (as measured with proflometry) and the AC amplitude used was 20 mV. Used to estimate the dielectric constant from the equation $C=\varepsilon_r\varepsilon_o A/d$, where C, A, and d are the measured capacitance, the active area of device, and the film thickness, respectively.

Although device performance exceeded 6% for interlayers ranging from ~5-55 nm, an optimum PCE was reached at ~15 nm thickness, followed by a steady decrease in efficiency for thicker interlayer films (FIG. 2C). To better understand the role of these polar fullerene interlayers, single-carrier devices were prepared to determine electron mobilities, using the modified Mott-Gurney law $$\left(J = \gamma \frac{9}{8}\varepsilon_r\varepsilon_0\mu\frac{V^2}{L^3},\right.$$

where $\gamma \leq 1$ is the contact non-ideality factor) for a space charge limited current (SCLC) regime of device operation (FIG. 4A and FIG. 24). First, electron-only devices were constructed using an ITO bottom electrode and Ca/Al top electrode with $PC_{71}BM$, $C_{60}$-N or $C_{60}$-SB as the bulk transport material. Assuming that Ca/Al is an Ohmic contact ($\gamma$=1), the electron mobilities of $5\times10^{-4}$ cm$^2$/Vs, $9\times10^{-4}$ cm$^2$/Vs and $1\times10^{-5}$ cm$^2$/Vs were estimated for $PC_{71}BM$, $C_{60}$-N and $C_{60}$-SB, respectively (the dielectric constants, $\varepsilon_r$, were determined by impedance spectroscopy to be 3.5 for $PC_{71}BM$ and 5.0 for $C_{60}$-N and $C_{60}$-SB, FIGS. 25-27). The higher electron mobility of $C_{60}$-N compared to $C_{60}$-SB explains why the photovoltaic devices with $C_{60}$-N interlayers work more efficiently up to larger interlayer thicknesses; while less efficient extraction of electrons through the thicker $C_{60}$-SB interlayers leads to larger series resistance, reducing the FF and $J_{SC}$ in such devices. Next, to determine whether Ag forms Ohmic contact with $PC_{71}BM$ directly and whether $C_{60}$-N interlayer improves its properties, devices were fabricated with an Ag top electrode and a $PC_{71}BM$, $PC_{71}BM/C_{60}$-N or $C_{60}$-N electron transport layer (FIG. 4A). Devices with only $PC_{71}BM$ showed evidence of a Schottky barrier, resulting in a $\gamma\times\mu$ product of $3\times10^{-7}$ cm$^2$/Vs, therefore indicating that $\gamma \leq 0.001$ (3 orders of magnitude lower than in diodes with Ca/Al electrode). This is consistent with a relatively high work function of Ag (4.45 eV) as compared to the LUMO of $PC_{71}BM$ (3.9 eV). Inserting a layer of $C_{60}$-N (13 nm, 25 nm or 48 nm) between PCnBM and Ag leads to a mobility of $2.5\times10^{-3}$ cm$^2$/Vs (4 orders of magnitude higher). Therefore, $C_{60}$-N/Ag forms a good Ohmic contact for electron injection into $PC_{71}BM$, better than Ca/Al does, while the value of $2.5\times10^-$ cm$^2$/Vs is a more accurate estimate of the electron mobility in $PC_{71}BM$. In the photovoltaic devices, lower potential barrier for electron injection at Ohmic contact translates into larger built-in potential that leads to faster electron extraction and, therefore, to higher $J_{SC}$ and FF. This is consistent with the systematically better performance of photovoltaic devices with $C_{60}$-N/Ag cathode. Additionally, single-carrier devices with only $C_{60}$-N as the bulk transport material and top Ag electrodes gave electron mobility ($1.1\times10^{-3}$ cm$^2$/Vs) equivalent to that measured using Ca/Al electrodes. Since the electron mobility of $PC_{71}BM$ is independent of $C_{60}$-N interlayer thickness and comparable to the electron mobility in $C_{60}$-N itself, electron transport through $C_{60}$-N in OPV devices is not hindered, and thus not the primary reason for decreasing PCEs with increasing interlayer thickness.

Figure 4B:
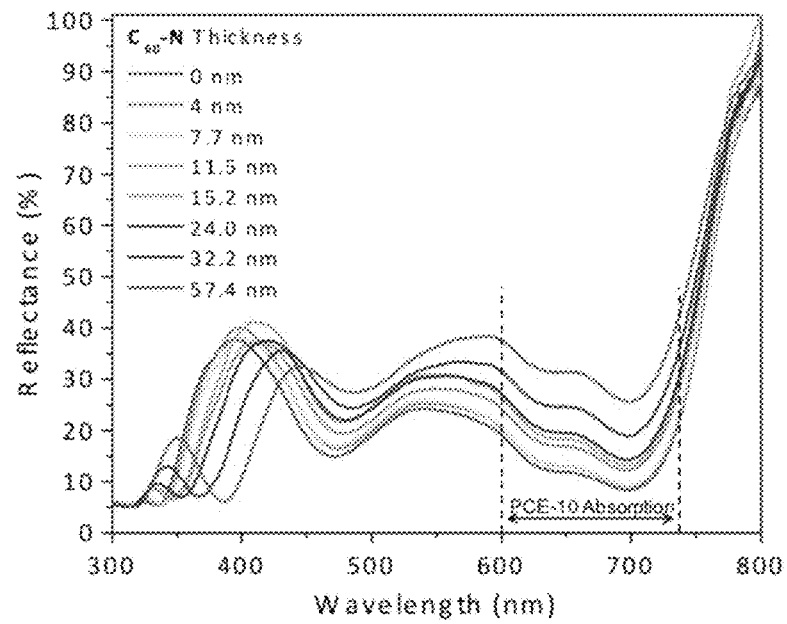
Figure 5:
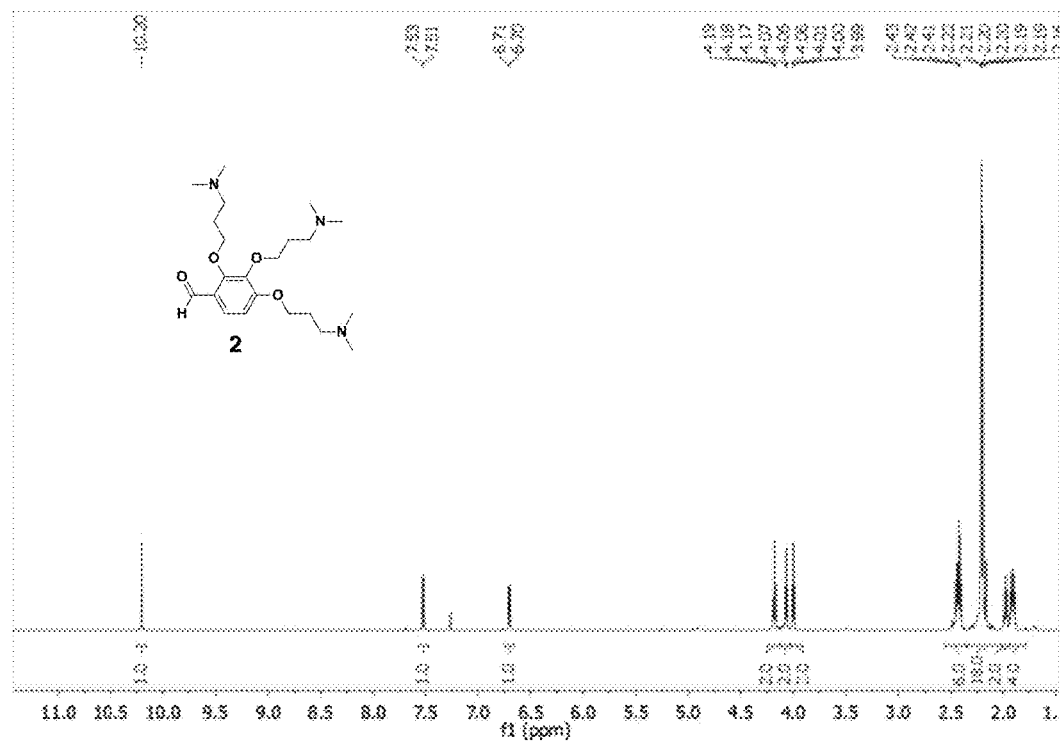
FIG. 5. $^1$H-NMR of compound 2 in CDCl$_3$.
Figure 6:
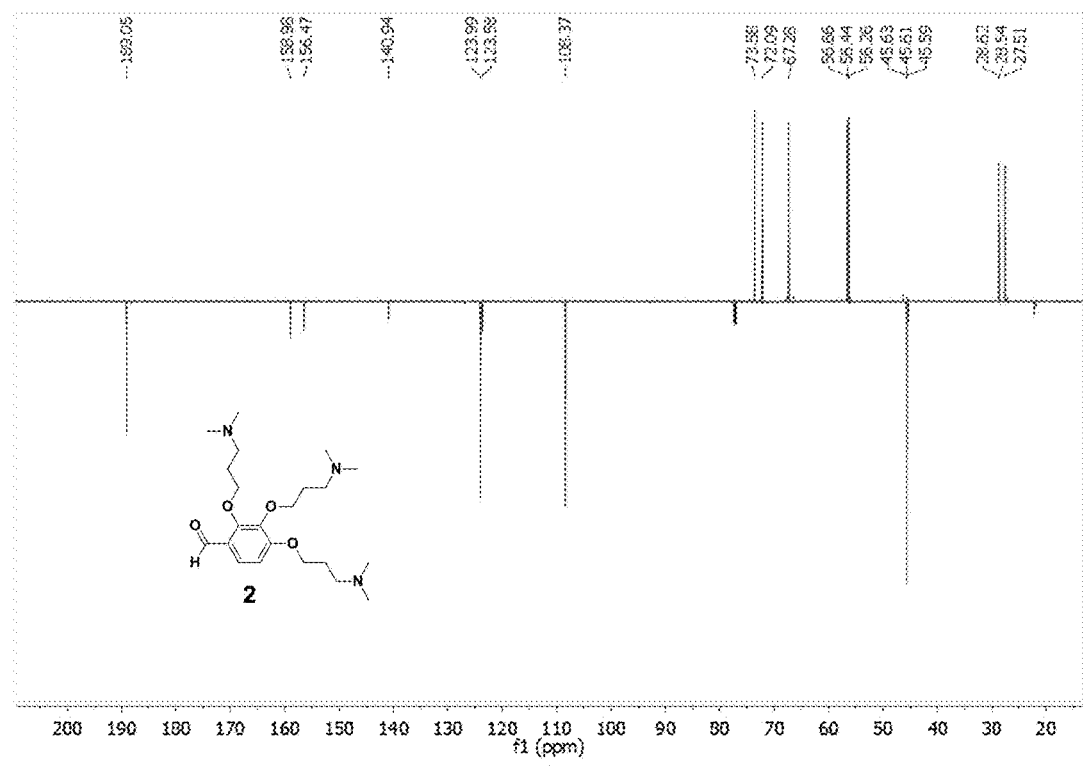
FIG. 6. $^{13}$C-NMR of compound 2 in CDCl$_3$, showing an overlay containing all hybridized carbons, including quaternary carbons in red (pointing down) with non-quaternary carbons in blue (CH & CH$_3$ pointing down, CH$_2$ pointing up).
Figure 7:
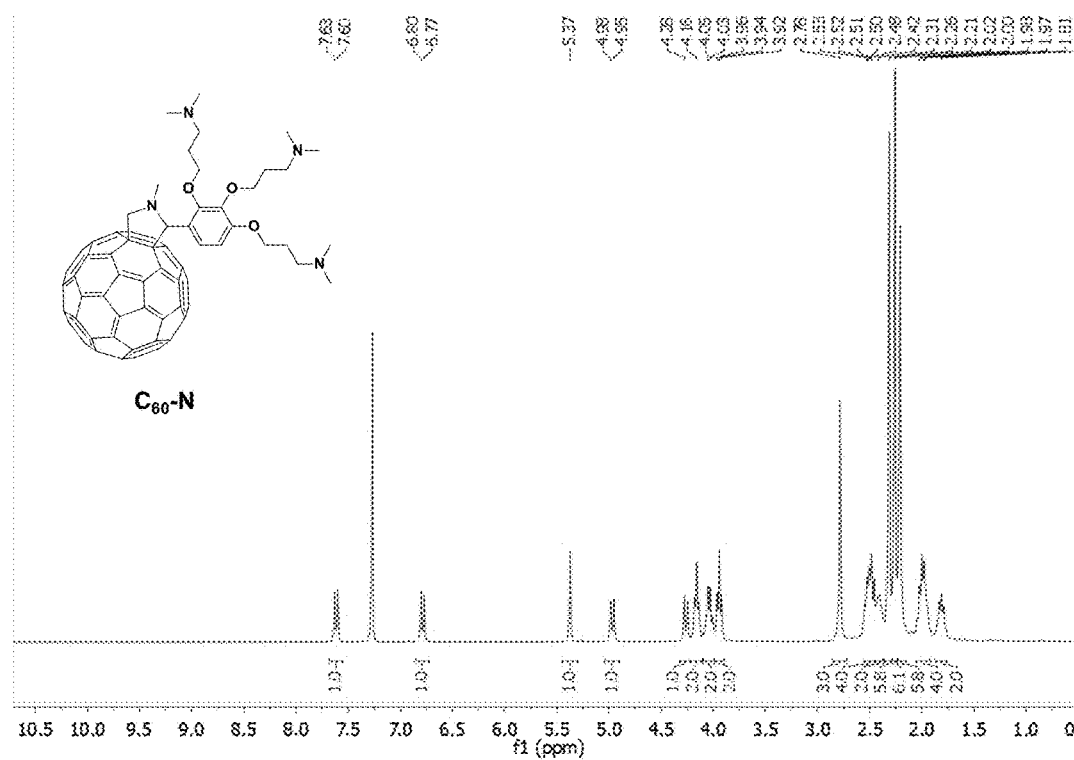
FIG. 7. $^1$H-NMR of C$_{60}$-N in CDCl$_3$.
Figure 8:
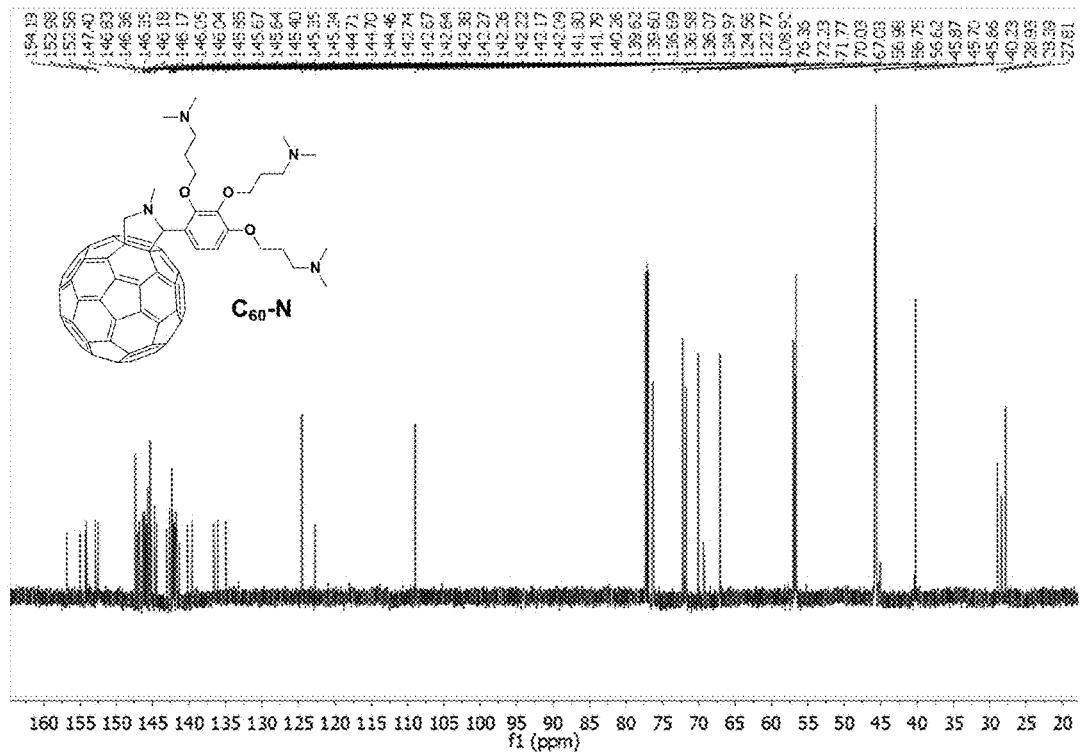
FIG. 8. $^{13}$C-NMR of C$_{60}$-N in CDCl$_3$.
Figure 9:
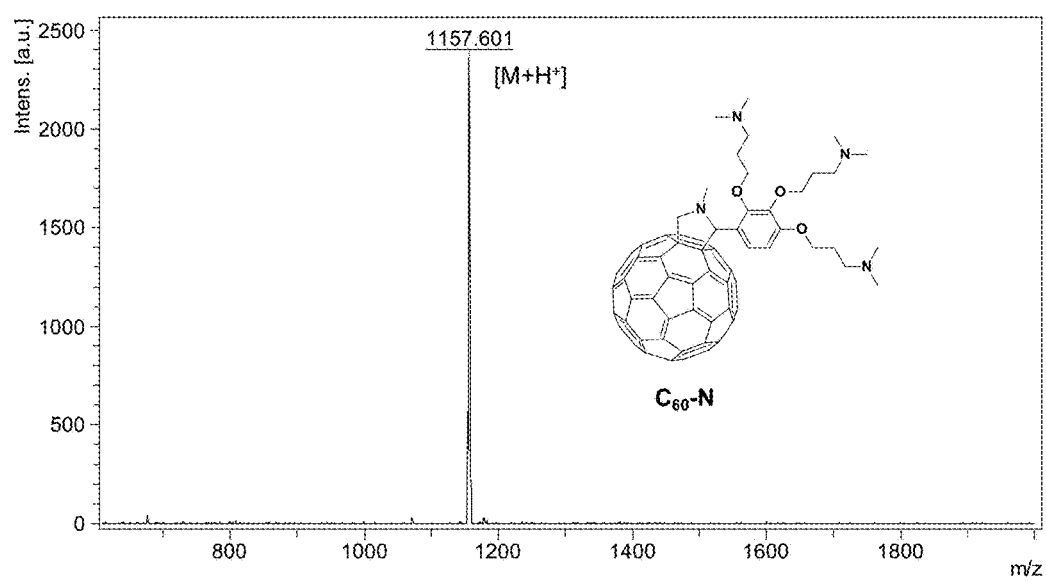
FIG. 9. MALDI-TOF mass spectrum of C$_{60}$-N.
Figure 10:
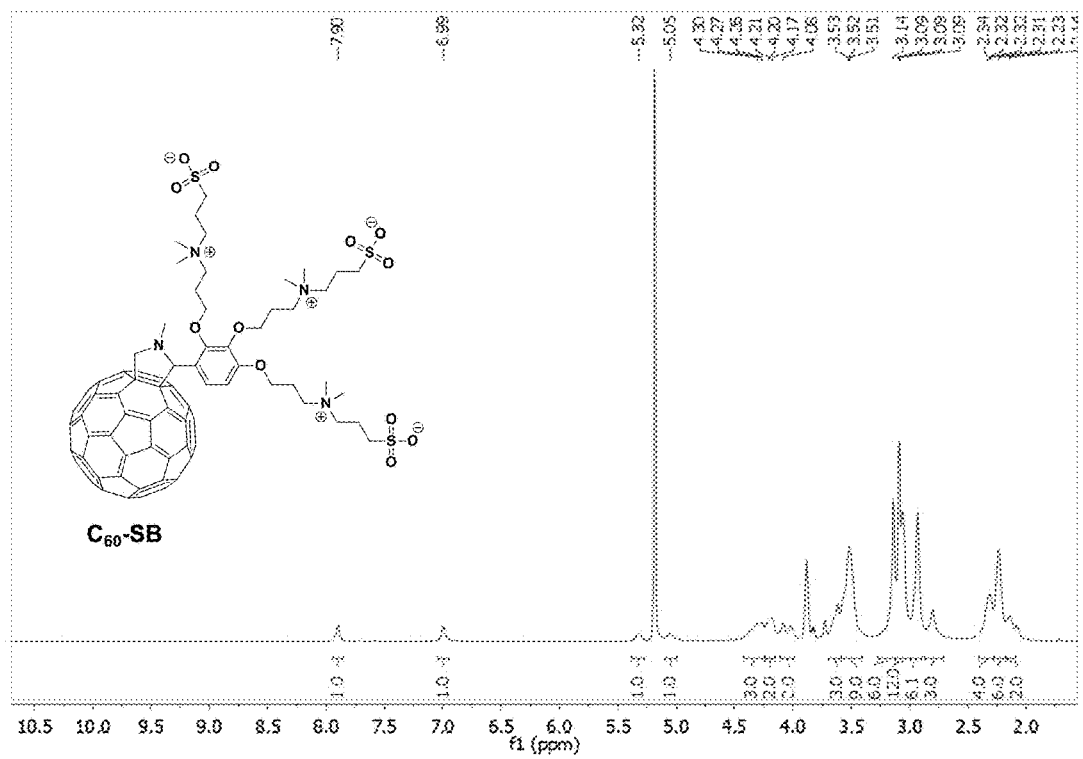
FIG. 10. $^1$H-NMR of C$_{60}$-SB in 2,2,2-Trifluoroethanol-d$_3$.
Figure 11:
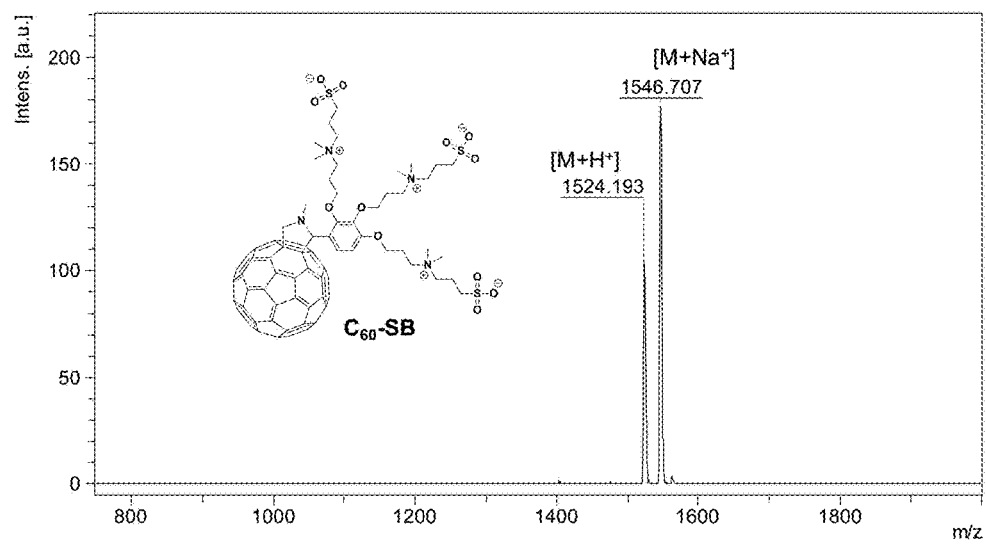
FIG. 11. MALDI-TOF mass spectrum of C$_{60}$-SB.
Figure 12:
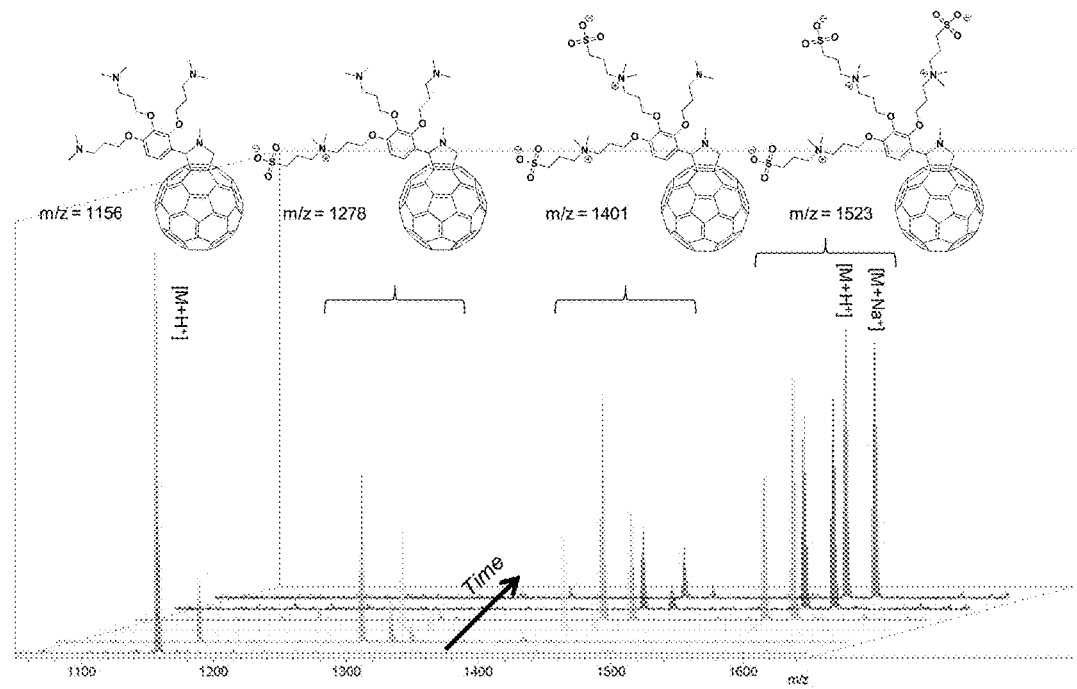
FIG. 12. MALDI-TOF mass spectra of the betainization reaction evolving over time in TFE, without added Na$_2$CO$_3$, showing the presence of residual bis(sulfobetaine)fulleropyrrolidine derivatives at 1403 g/mol (purple spectrum).
Figure 28:
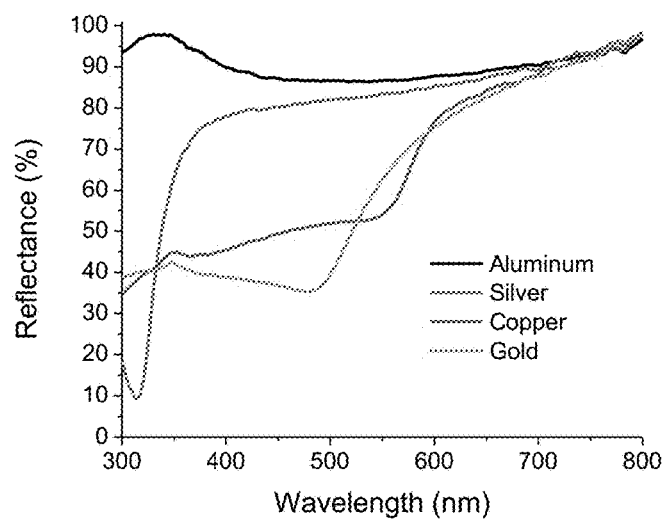
FIG. 28. Reflectance spectra showing reduced reflectance of visible light for copper and gold relative to aluminum and silver, which may be used in-part to explain the slightly reduced device performance for OPVs fabricated with Cu and Au cathodes compared to OPVs with Al and Ag cathodes. The reduced reflectance is from light absorption due to activation of plasmonic modes in the different metals.

To further examine the relationship between PCE and interlayer thickness, UV-Vis reflectance spectroscopy was performed directly on OPV devices with Ag cathode and $C_{60}$-N interlayers of different thicknesses (FIG. 4B). The measurements were made through the ITO substrate at 5° with respect to surface normal. Devices with interlayers thicker than 7.7 nm exhibited higher reflectance (reduced absorption) from 600 to 740 nm, where PCE-10 absorbs most strongly, and $C_{60}$-N has no absorption. This is direct evidence of an "optical spacer" effect, where $C_{60}$-N redistributes the optical field within the device. (Kim, et al. 2006 Adv. Mater. 18, 572-576.) The loss of absorption in the photoactive layer from 600 to 740 nm explains the reduced $J_{SC}$, and lower PCE, for OPV devices with thicker interlayers. Additionally, UV-Vis reflectance spectroscopy of bare metal cathodes reveals that lower PCE for devices with Cu (8.67±0.17%) or Au (8.56±0.21%) cathodes, relative to Ag (9.35±0.13%) can be attributed to enhanced visible light absorption through the activation of plasmonic modes in the metal (FIG. 28).

Thus, two novel fulleropyrrolidines bearing terminal tertiary amine or sulfobetaine functionalities were prepared and found to open new routes to high efficiency devices in conjunction with numerous active layer and electrode materials. Standard single-junction PSCs fabricated utilizing $C_{60}$-N and $C_{60}$-SB as buffer layers provided very high PCE values for such conventional devices, and unprecedented efficiency (9.78%) for Ag cathode devices. It was also shown that PCEs exceeding 8.5% were obtained irrespective of the cathodes work-function, even for the high work function Au ($\square$=5.1 eV), indicating a universal utility of these interlayers. UPS revealed that a "pinning" of the work-function at 3.65 eV is likely responsible for the observed cathode independent $V_{OC}$ values ($\approx$0.75 V) as well as for significantly improved $J_{SC}$ and FF values. Further, UPS, charge mobility measurements, and reflectance spectroscopy explain the origin of the higher efficiency in devices using $C_{60}$-N over $C_{60}$-SB buffer layers, of the apparent insensitivity of device performance (PCE>6%) to interlayer thicknesses (~5-55 nm), and of the exceptional performance of OPV devices with an Ag cathode (PCE=9.35±0.13%) in comparison to those with a Cu (8.67±0.17%) or Au cathode (8.56±0.21%). The synthetic accessibility of $C_{60}$-N and $C_{60}$-SB, along with their ability to provide highly efficient OPVs independent of the cathode material, makes these fulleropyrrolidines excellent candidates across organic electronic platforms.

Also demonstrated herein is the dual utility of $C_{60}$-SB acting as a thickness insensitive cathode modification layer and electron acceptor in efficient iPSCs, while demonstrating its applicability to large area, room temperature, all-solution processed fabrication techniques with slot-die coating.

Certain conjugated polymer zwitterions (CPZs) containing pendent sulfobetaine (SB) groups were recently developed. CPZs provide large negative $\Delta$ values (−0.5 eV to −0.9 eV) on metal substrates, and have demonstrated effectiveness as interlayers in PSCs over a thickness range of ~5 to 10 nm. (Page, et al. 2012 Macromolecules. 46, 344; Page, et al. 2014 J. Polym. Sci. Part A: Polym. Chem. 53, 327; Liu, et al. 2013 Adv. Mater. 25, 6868.) However, zwitterionic-substituted fullerenes, intrinsic n-type materials, reduce device sensitivity to ETL thickness. (Page, et al. 2014 Science 346, 441.) For example, the tris(sulfobetaine)-substituted fullerene ($C_{60}$-SB) is advantageous for its good solubility in trifluoroethanol (TFE), and insolubility in solvents used for processing active layers, such as chlorinated aromatics.

Figure 29:
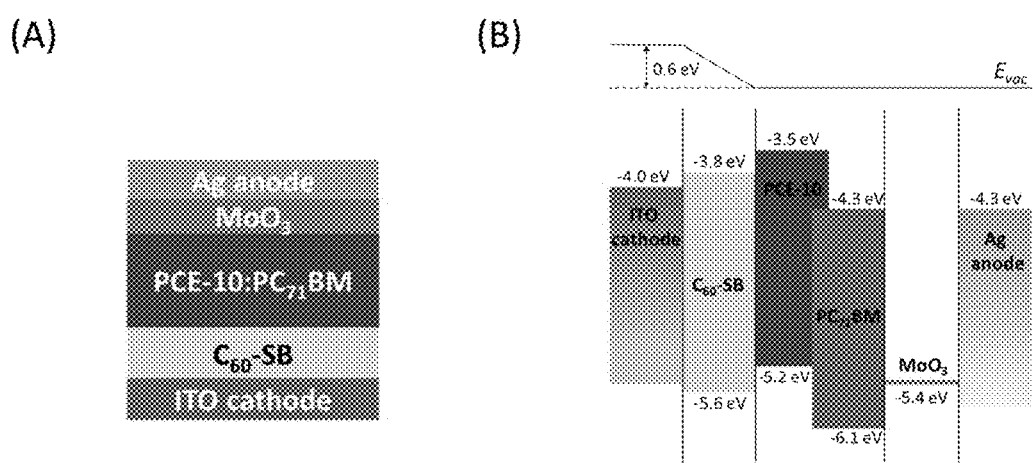
FIG. 29. Device structure (shown in A) and energy level diagram (interfacial dipole value (Δ) is shown in B).
Figure 30:
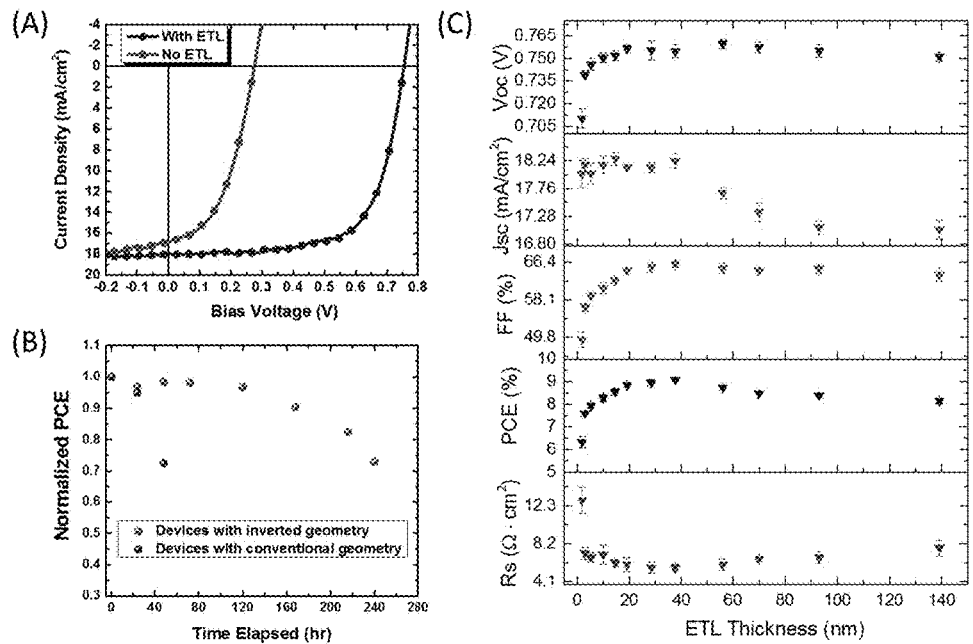
FIG. 30. (A) I-V curves of the control devices with and without $C_{60}$-SB ETLs (ETL thickness=40 nm); (B) normalized PCE for device stability investigation in ambient conditions. (C) thickness dependence of device performance on the $C_{60}$-SB ETL (Error represents ±1 standard deviation over eight devices).
Figure 35:
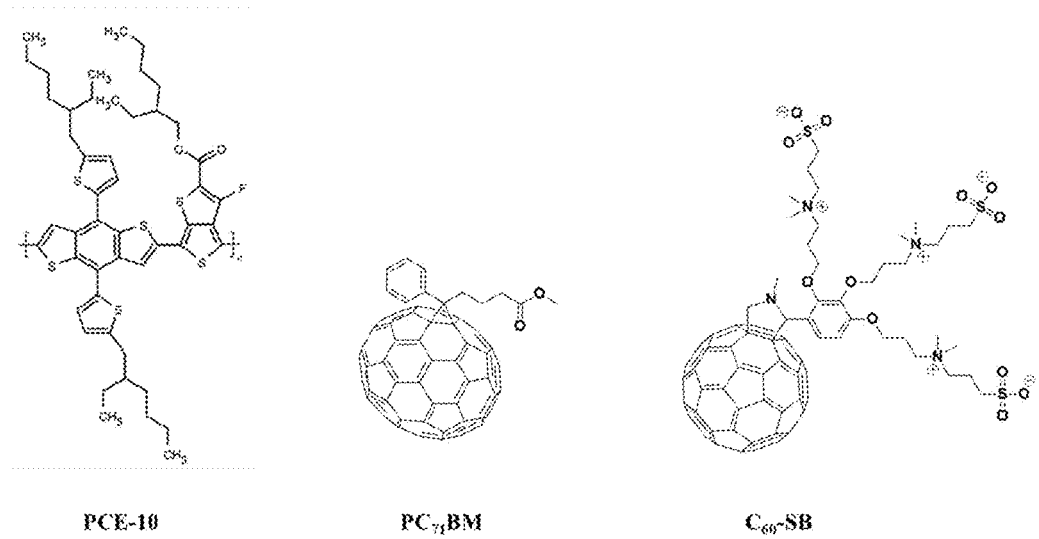
FIG. 35. Molecular structures of PCE-10, $PC_{71}BM$, and $C_{60}$-SB.

The present invention allows dual utility of $C_{60}$-SB in acting as a thickness insensitive cathode modification layer and electron acceptor in efficient iPSCs and enables applicability to large area, room temperature, all-solution processed fabrication techniques with slot-die coating.

iPSCs were fabricated by coating $C_{60}$-SB directly onto ITO substrates (FIG. 29). The BHJ active layer, containing a blend of [6,6]-phenyl $C_{71}$-butyric acid methyl ester ($PC_{71}BM$) as the acceptor and the low band gap conjugated polymer PCE-10 as the donor, was then coated onto a $C_{60}$-SB ETL (FIG. 29, chemical structures found in supporting information, FIG. 35). Molybdenum oxide was applied by evaporative deposition, followed by silver as the anode. The optimized iPSCs fabricated with bare ITO cathodes gave PCE values of 1.96±0.07% (maximum PCE 2.05%) (FIG. 30A, Table 5). In stark contrast, devices containing a $C_{60}$-SB ETL yielded PCE values of 9.08±0.05% (maximum PCE 9.23%) (FIG. 30A and Table 5). This dramatic improvement in PCE stems from higher open circuit voltage ($V_{oc}$) and fill factor (FF) values, while devices without the $C_{60}$-SB interlayers (i.e., with bare ITO cathodes) suffer from the high intrinsic work function of ITO and the resultant weak built-in electrostatic potential difference. In addition, ambient stability of the iPSCs was studied and compared to PSCs with a conventional geometry containing a $C_{60}$-SB/Ag cathode. Unencapsulated devices were removed from the glove box for 24-48 hour periods, and brought back into the glove box for testing, which revealed dramatically improved stability for iPSCs relative to those with a conventional geometry (FIG. 30B).

nm, the $J_{sc}$ gradually decreased to ~17 mA/cm², which explains the modest decrease in PCE from 9.08% (~40 nm ETL) to 8.15% (~140 m ETL) for these devices. Overall, an excellent device tolerance to ETL thickness is observed, and high PCE is maintained.

Figure 31:
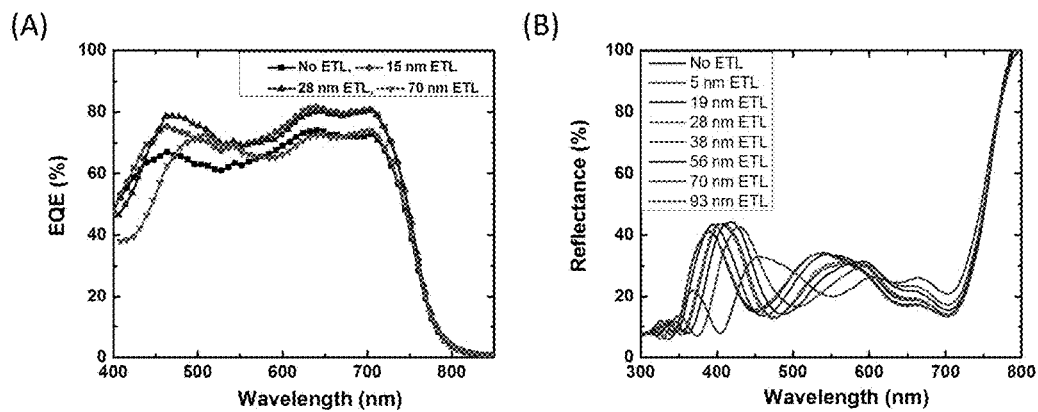
FIG. 31. (A) EQE of the devices with different ETL thickness; (B) UV-Vis reflectance spectroscopy of the devices with different ETL thickness.

An increase in the series resistance ($R_s$), from 5.57±0.37 Ω·cm² (~40 nm ETL) to 7.73±0.84 Ω·cm² (~140 nm ETL), is partly responsible for the observed reduction in $J_{sc}$ for devices with thicker ETLs (FIG. 30C, Table 5). The increased absorption by the thicker $C_{60}$-SB layer also leads to current loss, reflected in the external quantum efficiency (EQE) measurements (FIG. 31A), where a decrease of EQE is observed below 500 nm. UV-Vis reflectance spectroscopy (FIG. 31B) probed the redistribution of the optical field within devices containing different ETL thicknesses. Increasing ETL thickness (from 2 to 70 nm) led to decreased reflectance (enhanced absorption) from 475 to 575 nm, where $C_{60}$-SB has negligible absorption. Correspondingly, EQE was greater over this wavelength range for the same device structure. Although the enhanced absorption contributes to the overall $J_{sc}$, a competing increase in reflectance (reduced absorption) from 600 to 740 nm, where PCE-10 absorbs most strongly, was found for devices containing ETLs thicker than 30 nm. Hence, the suppressed absorption in the 600 to 740 nm range for devices having thicker ETLs is responsible for the reduced $J_{sc}$.

To further understand the working mechanism of $C_{60}$-SB as an ETL in iPSCs, $C_{60}$-SB/PCE-10 bilayer devices (FIG. 32) were prepared by coating pure PCE-10 directly onto $C_{60}$-SB. These bilayer devices gave $V_{oc}$ values of

TABLE 5

Device performance under difference ETL thickness (Error represents ±1 standard deviation over eight devices)

| ETL thickness (nm) | $V_{oc}$ (V) | $J_{sc}$ (mA/cm²) | FF (%) | PCE (%) | $R_s$ (Ω · cm²) |
|---|---|---|---|---|---|
| none | 0.27 ± 0.005 | 16.059 ± 0.16 | 44.38 ± 1.55 | 1.96 ± 0.07 | 13.29 ± 0.52 |
| 1.8 | 0.71 ± 0.006 | 18.017 ± 0.23 | 49.31 ± 1.72 | 6.33 ± 0.25 | 12.89 ± 1.42 |
| 3.0 | 0.74 ± 0.003 | 18.170 ± 0.11 | 56.44 ± 0.81 | 7.59 ± 0.14 | 7.14 ± 0.66 |
| 5.3 | 0.75 ± 0.004 | 18.019 ± 0.18 | 59.04 ± 0.78 | 7.93 ± 0.08 | 6.68 ± 0.50 |
| 9.9 | 0.75 ± 0.003 | 18.171 ± 0.15 | 60.71 ± 1.26 | 8.28 ± 0.16 | 7.03 ± 1.04 |
| 14.5 | 0.75 ± 0.003 | 18.277 ± 0.11 | 62.43 ± 0.66 | 8.56 ± 0.15 | 6.13 ± 0.38 |
| 19.1 | 0.76 ± 0.003 | 18.132 ± 0.05 | 64.56 ± 0.63 | 8.85 ± 0.08 | 5.94 ± 0.72 |
| 28.4 | 0.76 ± 0.006 | 18.126 ± 0.08 | 65.36 ± 1.07 | 8.95 ± 0.14 | 5.63 ± 0.63 |
| 37.6 | 0.75 ± 0.004 | 18.238 ± 0.12 | 65.97 ± 0.63 | 9.08 ± 0.05 | 5.57 ± 0.37 |
| 56.0 | 0.76 ± 0.003 | 17.687 ± 0.10 | 65.03 ± 1.12 | 8.74 ± 0.12 | 5.94 ± 0.63 |
| 69.9 | 0.76 ± 0.004 | 17.352 ± 0.16 | 64.48 ± 0.66 | 8.47 ± 0.05 | 6.54 ± 0.27 |
| 93.0 | 0.76 ± 0.004 | 17.090 ± 0.11 | 64.95 ± 1.10 | 8.38 ± 0.11 | 6.70 ± 0.62 |
| 139.2 | 0.75 ± 0.003 | 17.055 ± 0.16 | 63.67 ± 1.51 | 8.15 ± 0.12 | 7.73 ± 0.84 |

The dependence of device performance on $C_{60}$-SB ETL thickness was investigated by spin-coating $C_{60}$-SB solutions of varying concentrations onto ITO substrates to afford ETLs over a thickness range from 1.8 to 140 nm. As shown in FIG. 30C, $V_{oc}$ FF and PCE improved steadily with increasing ETL thickness. For an ETL thickness of 1.8 nm, the $V_{oc}$ values are 0.71±0.006 V, FF values are 49.3±1.72%, and PCE values are 6.33±0.25%, while an ETL thickness of 40 nm results in $V_{oc}$ values of 0.76±0.004 V, FF values of 66±0.63%, and PCE values of 9.08±0.05%, respectively. Interestingly, both $V_{oc}$ and FF were largely maintained even when the ETL thickness was 140 nm, surpassing the thickness of the BHJ photoactive layer (~100 nm). However, the short circuit current density ($J_{sc}$) exhibited a very different trend from $V_{oc}$ and FF (FIG. 30C). Below an ETL thickness of 40 nm, $J_{sc}$ maintained a constant value of ~18 mA/cm². Surprisingly, with increased ETL thickness from 40 to 140

Figure 32:
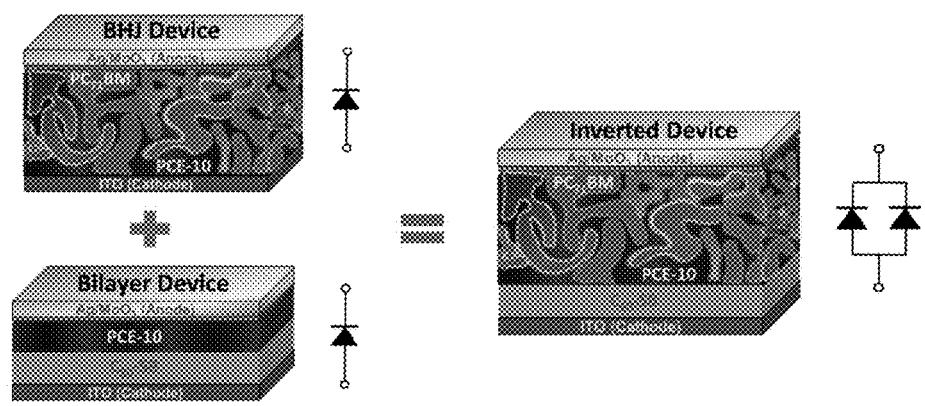
FIG. 32. Diagram for the formation of parallel like solar cell.
Figure 36:
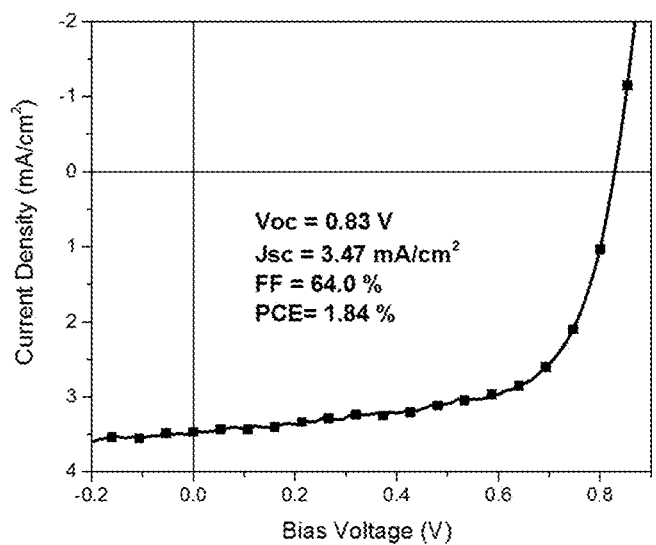
FIG. 36. I-V cure and device performance of PCE-10/ C60-SB bilayer device.
Figure 37:
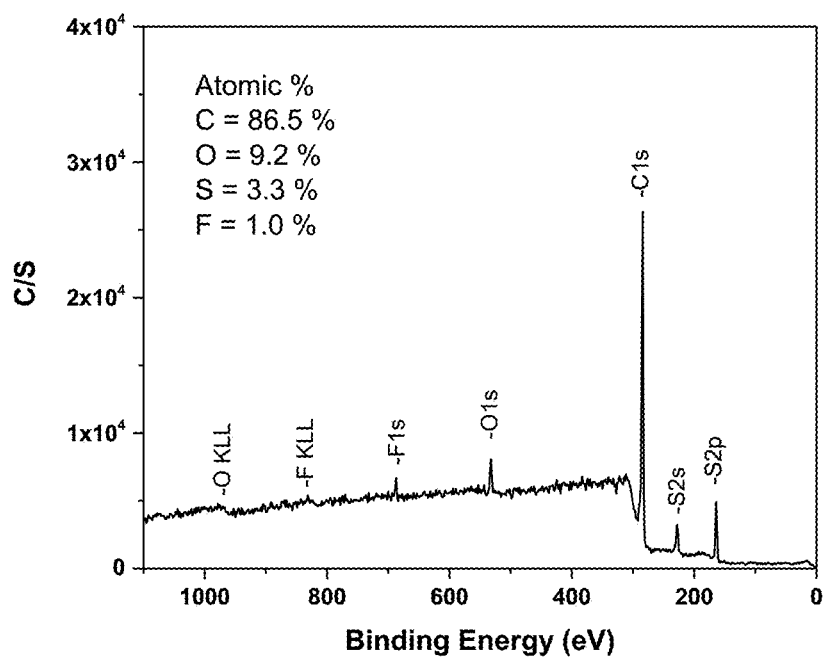
FIG. 37. XPS characterization for the bottom surface of the BHJ film.

0.82±0.008 V, $J_{sc}$ values of 3.46±0.05 mA/cm², FF values of 63.7±0.47%, and PCE values of 1.80±0.03% (FIG. 36). The working OPV bilayer devices, in which PCE-10 functions as the donor layer and $C_{60}$-SB as the acceptor layer, demonstrates the capability of the $C_{60}$-SB/PCE-10 interface to effectively separate excitons into free charges, while $C_{60}$-SB acting as a cathode modification layer (FIG. 32). To elucidate whether these mechanisms pertain to the BHJ iPSCs, X-ray photoelectron spectroscopy (XPS) was utilized to probe the composition of the bottom BHJ interface that contacts $C_{60}$-SB (FIG. 37). This was accomplished by selectively dissolving $C_{60}$-SB with TFE, followed by flipping the BHJ film and placing it onto a substrate for XPS analysis. Significant "F1s", "S1s", and "S2p" signals were observed, indicating that the bottom of the BHJ layer (in contact with $C_{60}$-SB) contains PCE-10 (~30 wt % by integration) (FIG. 37). Therefore, this contact functions as a bilayer solar cell, where the $C_{60}$-SB interlayer also serves as the acceptor, contributing to the overall device performance (FIG. 32). Hence, these iPSCs function is expected to function like two single junction devices (BHJ and bilayer) in parallel, where excitons generated in the PCE-10 phase migrate to the polymer/$PC_{71}BM$ and polymer/$C_{60}$-SB interfaces, then dissociate into free electrons and holes (FIG. 32). (Yang, et al. 2012 *J. Am. Chem. Soc.* 134, 5432.) Holes transport through polymer channels to the anode and electrons generated in the BHJ transport through the $PC_{71}BM$ enriched domains to the $C_{60}$-SB interlayer, then through the $C_{60}$-SB layer in conjunction with electrons generated at the polymer/$C_{60}$-SB interface, which are collected by the ITO cathode. The thickness insensitivity is attributed to this dual functionality of the $C_{60}$-SB layer. In addition, the higher relative dielectric constant of $C_{60}$-SB ($\varepsilon$=5.0) is expected to suppress bimolecular (non-geminate) recombination, mitigating space charge effects, while simultaneously decreasing the exciton binding energy at the polymer/$C_{60}$-SB interface. (Koster, et al. 2012 *Adv. Energy Mater.* 2, 1246; Cho, et al. 2014 *Adv. Energy Mater.* 4, 1301857.)

TABLE 6

The surface element composition (in atomic fractions) of $C_{60}$-SB ETLs spun-coated onto ITO substrates.

| Film thickness on ITO (nm) | Tilted angle (Degree) | Atomic % | | | |
|---|---|---|---|---|---|
| | | C1s | O1s | N1s | S2p |
| 2 | 15 | 78.7 | 17.4 | 2.1 | 1.8 |
| | 45 | 67.9 | 28.3 | 2.2 | 1.6 |
| 5 | 15 | 82.1 | 13.5 | 2.7 | 1.7 |
| | 45 | 78.2 | 16.2 | 3.4 | 2.2 |
| 15 | 15 | 80.7 | 14.4 | 2.9 | 2.0 |
| | 45 | 78.8 | 15.6 | 3.0 | 2.6 |

Figure 33:
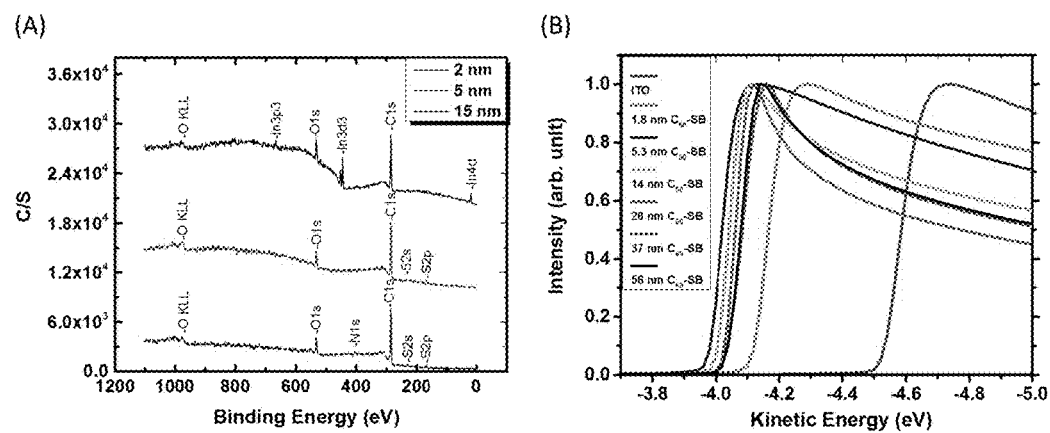
FIG. 33. (A) XPS results and (B) UPS results of $C_{60}$-SB ETLs coated onto ITO substrates with different thickness.

The molecular orientation of the $C_{60}$-SB ETL on ITO was probed by angle-dependent XPS measurements, determining the elemental composition at the film surface (FIG. 33A). Data is shown in Table 6 (in atomic fractions) for $C_{60}$-SB on ITO (take-off angle 15°-45°; detection depth 1-2.5 nm). For an ETL thickness of 2 nm, the signal arising from ITO (In3p3, In3d3, and In4d) can be detected even at a take-off angle of 15° (detection depth 1-1.5 nm), indicating incomplete $C_{60}$-SB coverage. Increasing the $C_{60}$-SB layer thickness to ~5 nm causes the signal from the ITO to vanish, suggesting full coverage by $C_{60}$-SB. For the fully covered samples, a gradient in element composition was found, as shown in Table 6. Increasing the take-off angle from 15° to 45° resulted in a decrease in the atomic fraction of carbon, while the relative amount of oxygen, nitrogen and sulfur increased. Since fullerene has a diameter of ~1 nm, comparable to the detection depth increment from a take-off angle of 15°-45°, the observed changes in element composition must arise from the preferential orientation of the zwitterionic sulfobetaine chains towards the ITO surface. To complement XPS, ultraviolet photoelectron spectroscopy (UPS) was performed to characterize the electronic effect of $C_{60}$-SB on ITO (FIG. 33B). The high energy region of the UPS provides interfacial dipole ($\Delta$) values that reflect the difference in the high binding energy onsets, or $E_{SEC}$, of bare vs. coated ITO. UPS characterization of $C_{60}$-SB on ITO showed that a ~5 nm thick layer of $C_{60}$-SB had the largest $\Delta$=0.6 eV (FIG. 33B), and this remained relatively constant with increasing $C_{60}$-SB film thickness (even >50 nm). A lower $\Delta$ value was observed for the 1.8 nm thick films, which likely arises from incomplete coverage, in accord with XPS results. The large negative $\Delta$ value for films>1.8 nm in thickness increases the built-in electrostatic potential difference in the device, improving charge extraction and reducing recombination losses, consistent with the high $J_{sc}$ and FF values of the devices. Similar to CPZs, work function modification of ITO by $C_{60}$-SB may arise from orientation of the permanent dipole at the interface, due to the preferential interactions of the sulfobetaine zwitterion with the ITO surface. (Liu, et al. 2013 *Adv. Mater.* 25, 6868; Page, et al. 2014 *Science* 346, 441.)

Figure 34:
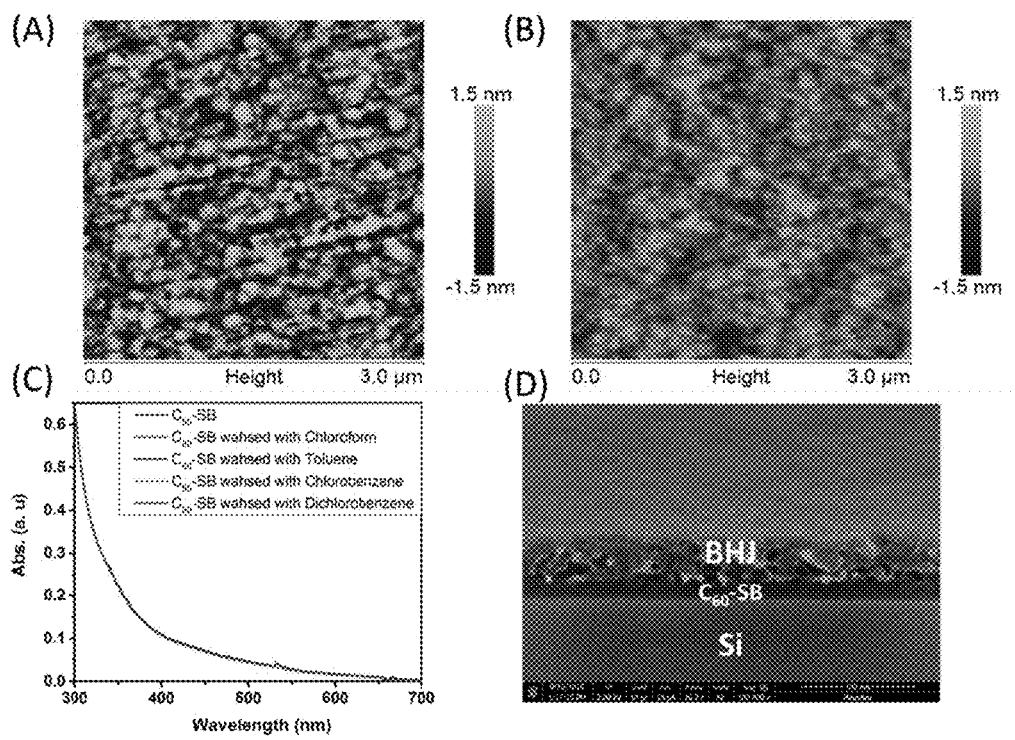
FIG. 34. AFM topography image of (A) bare ITO substrate and (B) after coating with $C_{60}$-SB ETL; (C) UV-Vis absorption of $C_{60}$-SB films treated with different organic solvents; (D) Cross-section SEM image of the interface between the BHJ active layer and $C_{60}$-SB ETL.

Atomic force microscopy (AFM) showed the surface of the bare ITO with a root-mean-squared (RMS) roughness of 0.65 nm (FIG. 34A). After coating with $C_{60}$-SB (~40 nm thick), the surface roughness decreased to 0.21 nm (FIG. 34B), indicating the presence of a continuous film of $C_{60}$-SB; this may also contribute to improved device performance due to the good film-forming property of $C_{60}$-SB on ITO. To investigate solvent resistance of $C_{60}$-SB films, common solvents (chloroform, toluene, chlorobenzene and dichlorobenzene) were used in washing steps of $C_{60}$-SB on glass. UV-visible absorption (FIG. 34C) shows that these solvents neither remove the films nor modify their electronic signature. Furthermore, the interfacial properties between the BHJ active layer and $C_{60}$-SB layer was investigated by cross-section scanning electron microscopy (SEM) (FIG. 34D). The $C_{60}$-SB layer was prepared by spin-coating an 8 mg/ml $C_{60}$-SB solution in TFE onto UV-ozone treated silicon wafers, affording a film thickness of ~40 nm. A sharp interface between the active layer and $C_{60}$-SB layer was found indicating that $C_{60}$-SB and the active layer do not interdiffuse (FIG. 38).

Figure 40:
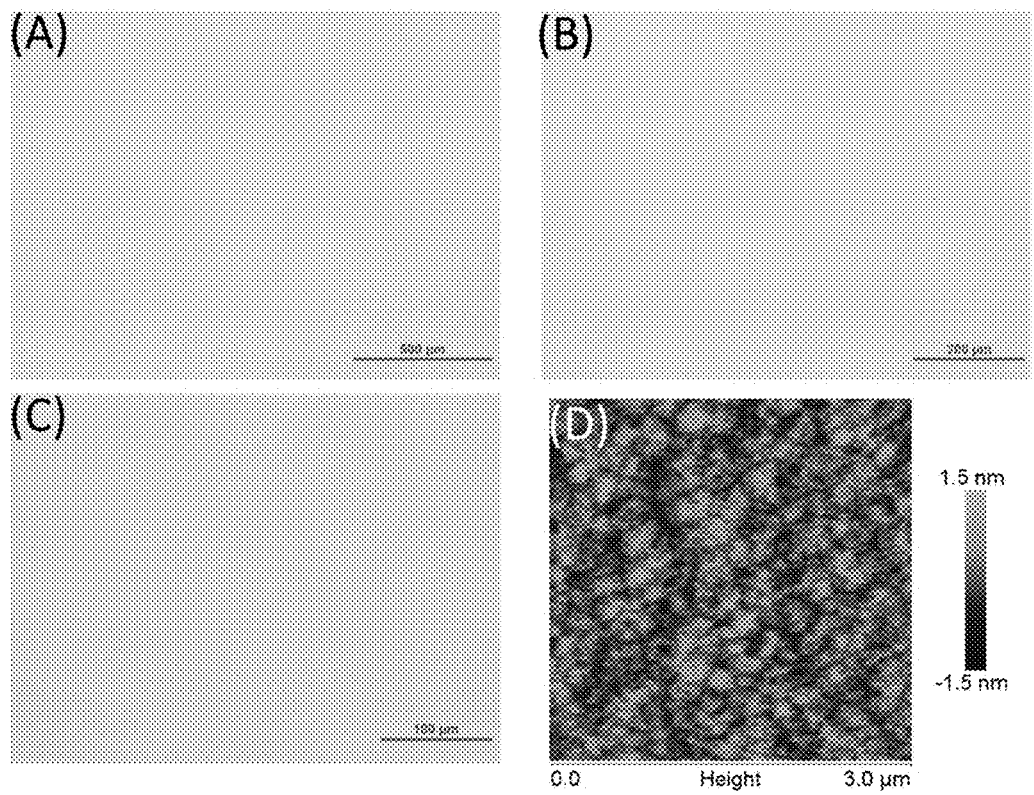
FIG. 40. Slot-die coated $C_{60}$-SB on ITO: (A), (B), and (C) optical microscopy images in different scale; (D) AFM image with a RMS of 0.32 nm, which is similar to spin-coated film.
Figure 41A:
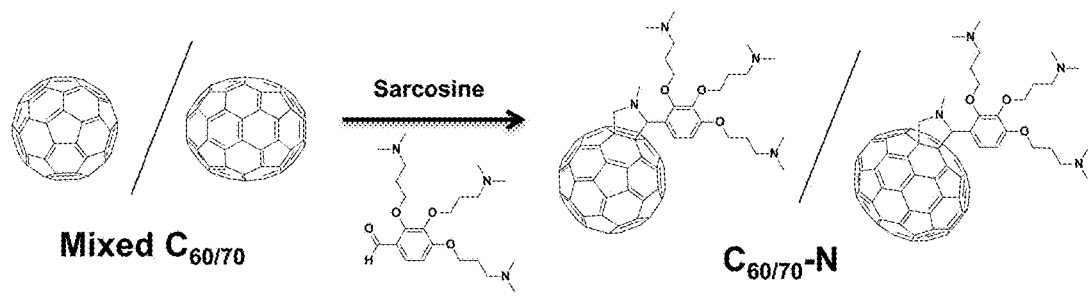
FIG. 41. Synthesis of amine-substituted mixed $C_{60}/C_{70}$ fullerenes, comparative device data, spectroscopic evidence of the similar electronic properties between the pure $C_{60}$ and mixed fullerene structures.
Figure 41B:
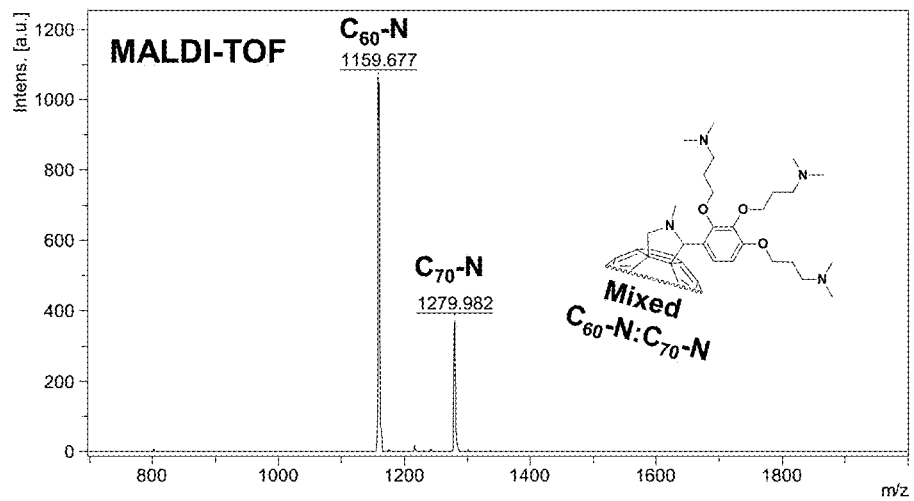
Figure 41C:
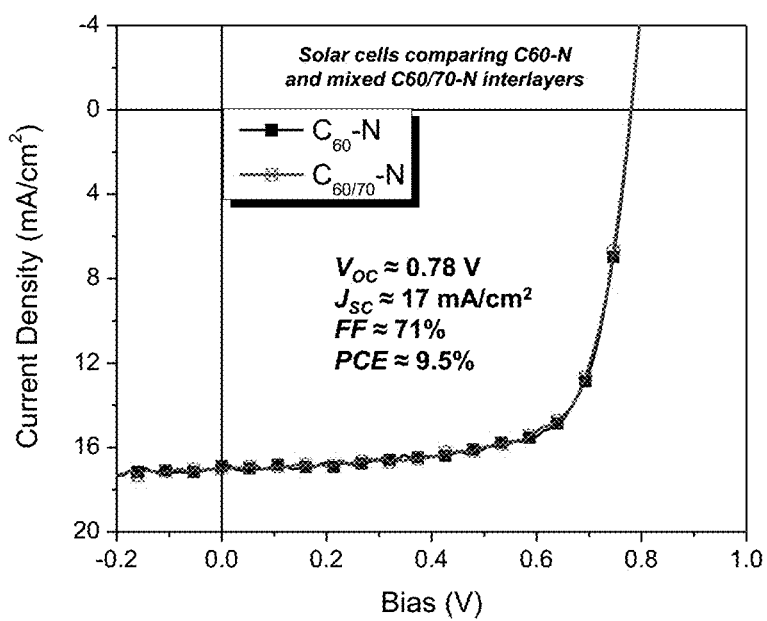
Figure 41D:
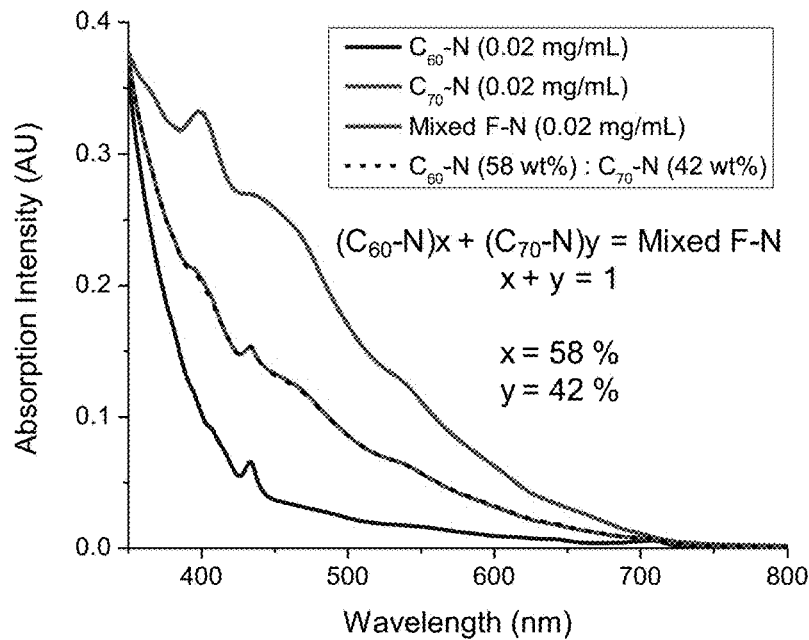
Figure 41E:
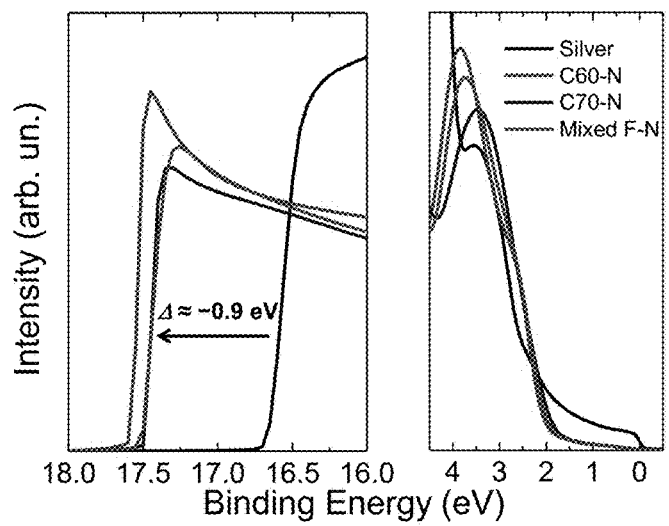

The orthogonal solubility of $C_{60}$-SB with the photoactive layer, combined with excellent thickness tolerance, opens the potential for roll-to-roll (R2R) and slot-die processing. The compatibility of slot-die coating processes with $C_{60}$-SB was investigated using the mini-slot die coater shown in FIG. 39A. A detailed description on the components and working mechanism of this coater is given elsewhere. (Liu, et al. 2014 *Adv. Mater.*, DOI: 10.1002/adma.201404040.) During the slot-die coating process, a $C_{60}$-SB solution was first injected onto a pre-cleaned ITO substrate through the slot-die head using a conventional syringe pump. Uniform films of $C_{60}$-SB (~35 nm) on ITO were obtained over large areas with a RMS roughness of 0.32 nm as measured by AFM (FIG. 39B, FIG. 40), followed by directly slot-die coating an active layer film (PCE-10:$PC_{71}BM$, 120 nm) onto the $C_{60}$-SB ETL. The present method demonstrates how both a $C_{60}$-SB ETL and photoactive layer can be concurrently coated by slot-die to obtain uniform thin films over a large area. Preliminary photovoltaic performance testing of these devices has thus far been performed with an illumination area of 0.11 cm$^2$, resulting in PCEs of 7.38%, with further device optimization and large-area testing currently under way (FIG. 39C, FIG. 39D). This is believed to be the first report of an organic ETL used in a large area slot-die coating process. In addition, this solution processable ETL can be used without post-processing treatment, indicating its potential compatibility with fast and mass-production processes.

In summary, high performance iPSCs were successfully fabricated with an organic ETL composed of zwitterionic fullerenes. PCEs as high as 9.23% were achieved with an ETL thickness of ~40 nm. Exceptional insensitivity to the ETL thickness, from 5 nm to 140 nm, was found, with PCEs exceeding 8% across the entire thickness range. $C_{60}$-SB layers function both as electron acceptor and cathode modification layers in iPSC devices. This dual role of the zwitterionic fullerene contributes to the ETL thickness insensitivity of device performance, which is an important and unique property of $C_{60}$-SB. XPS and UPS showed that a $C_{60}$-SB thickness of ~5 nm is necessary for full coverage of an ITO substrate, where upon the work function of ITO was decreased by ~0.6 eV. The orthogonal solubility of $C_{60}$-SB and the active layer, coupled with its thickness insensitivity, enabled slot-die preparation of iPSCs with PCEs of 7.38% effectively, opening a new route to efficient large area devices that can be fabricated at room temperature.

It was found that a mixture of functional fullerenes, specifically amine-substituted $C_{60}$ and $C_{70}$, gives excellent results when used as interlayers in solar cell fabrication. The $C_{60}/C_{70}$ mixture represents an inexpensive alternative (about 25% of the cost) relative to the preparation of substituted pure $C_{60}$, using identical chemical transformations. Moreover, this approach varies, albeit slightly, the composition of matter of the interlayer. Spectroscopic characterization of the commercial $C_{60}/C_{70}$ materials indicate an approximately 3:2 ratio of $C_{60}$ to $C_{70}$ in the mixture, and MALDI-TOF mass spectrometry confirms the presence of each amine-substituted structure in the mixture. The fullerene mixture is electronically similar to the pure $C_{60}$ and $C_{70}$ compounds, as seen by ultraviolet photoelectron spectroscopy to have similar ionization potential and work function reduction of Ag. Solar cells containing the mixed fullerenes as the cathode modification layer are equally efficient to those containing the pure $C_{60}$ interlayer. FIG. 41 describes the synthesis of amine-substituted mixed $C_{60}/C_{70}$ fullerenes, comparative device data, spectroscopic evidence of the similar electronic properties between the pure $C_{60}$ and mixed fullerene structures.

Experimental

Materials

3-Dimethylamino-1-propanol (99%), triphenylphosphine (99%), diisopropyl azodicarboxylate (98%), anhydrous 1,2-dichlorobenzene (99%), aluminum oxide (activated, basic, Brockmann I), triethylamine (>99%), sarcosine (99%), 1,3-propanesultone (99%) and 1,8-diiodooctane (98%) were purchased from Sigma Aldrich and used without further purification. 2,3,4-Trihydroxybenzaldehyde (98%) was purchased from Combi-Blocks and used without further purification. Fullerene-$C_{60}$ (99.95%) was purchased from Materials Technologies Research (MTR) and used without further purification. Chloroform-D (99.8%) and 2,2,2-trifluoroethanol-D3 (99%) were purchased from Cambridge Isotope Laboratories. 2,2,2-Trifluoroethanol (99+%) was purchased from Alfa Aesar, silica gel (200×400 mesh) was purchased from Sorbent Technologies, Sephadex LH-20 was purchased from GE Healthcare Life Sciences and Spectra/Por dialysis tubing was purchased from Spectrum Labs. Tetrahydrofuran (99%, EMD) (THF) was dried over sodium/benzophenone ketyl, and distilled before use. Anhydrous magnesium sulfate, sodium carbonate, hexanes, chloroform, methanol, acetone, diethyl ether and dichloromethane were purchased from Fisher Scientific. PTB7 and PCE-10 were purchased from 1-Material and $PC_{71}BM$ was purchased from Nano-C.

Instrumentation $^1$H-NMR spectra were recorded at 300 MHz on a Brüker-spectrospin or 700 MHz on an Agilent Technologies Varian and $^{13}$C-NMR at 176 MHz on an Agilent Technologies Varian. Centrifugation was done using an eppendorf centrifuge 5804 and lyophilization using a Labconco FreeZone® 4.5 Liter Freeze Dry System, model 77500. UV/vis absorbance measurements were taken on a Perkin-Elmer Lambda 25 UV/vis spectrometer. UPS measurements were performed on the Omicron Nanotechnology, Model ESCA+S, consisting of a helium discharge lamp (He I line, 21.2 eV) as the UV excitation source and a hemispherical SPHERA energy analyzer. All samples were negatively biased by −3V during the measurements. This bias compensated for the instrument work function difference repelling the low-kinetic energy electrons. The energy scale of experimental graphs was shifted by 3 eV. Fullerene film thickness was determined by a combination of the surface profiler KLA Tencor, model Alpha-Step IQ, and UV-Vis absorption measurements given attenuation coefficients ($\alpha$). X-ray photoelectron spectroscopy (XPS) was done on a Physical Electronics Quantum 2000 Scanning ESCA Microprobe using Al k-alpha x-rays, and a Pass Energy of 46.95 eV for multiplexes, and 187.85 eV for surveys. Matrix assisted laser desorption ionization time of flight (MALDI-TOF) data were obtained on a Brüker microflex using a microScout Ion Source and linear mode detection. The matrix used was [2-(4-hydroxyphenylazo)-benzoic acid] (HABA) which was drop cast from a 40 mg/mL solution in THF containing approximately 0.1-1 mg/mL of the analyte added to the mixture as a solution in either THF ($C_{60}$-N and $C_{60}$-alkyl) or TFE ($C_{60}$-N and $C_{60}$-SB). Certain XPS were recorded with a Perkin-Elmer-Physical Electronics 5100 with Mg KR excitation (400 W). Spectra were obtained at three different takeoff angles, 15° and 45° (angle between the surface plane and the entrance lens of the detector optics). Atomic force microscopy was performed on a Digital Instruments Dimension 3100, operating in tapping mode. Cross-section scanning electron microscopy (SEM) was performed on a FEI Magellan 400 FESEM. UV/vis absorbance and reflectance measurements were recorded on a Perkin-Elmer Lambda 25 UV/vis spectrometer. Polymer film thickness was determined using the surface profiler KLA Tencor (model Alpha-Step IQ).

Synthesis of
2,3,4-tris(3-(dimethylamino)propoxy)benzaldehyde
(2)

A 2-neck, 250 mL round-bottom flask equipped with a magnetic stir bar, inlet adapter, addition funnel and septa was flushed with nitrogen, followed by addition of 2,3,4-trihydroxybenzaldehyde (2.00 g, 13.0 mmol), 3-dimethylaminopropan-1-ol (4.55 g, 44.1 mmol), triphenylphosphine (11.57 g, 44.1 mmol) and THF (anh, 45 mL). The mixture was cooled to 0° C. with an ice bath while stirring under nitrogen. Diisopropyl azodicarboxylate was added to the addition funnel, dissolved in THF (anh, 15 mL) and added dropwise to the reaction mixture. After complete addition the flask was removed from the ice bath and stirred at room temperature for five hours. The reaction was concentrated and the resulting crude mixture was washed with Hex:$Et_2O$ (1:1), filtering off the white phosphine-oxide byproduct through celite. The filtrate was concentrated, dissolved in DCM and washed with 1M HCl (aq) (50 mL, 3×). The aqueous fractions were combined and washed with DCM until the organic phase no longer contained a UV-active compound (tested on UV-active TLC plates under shortwave 254 nm light). The acidic aqueous layer was neutralized with sodium carbonate (sat., aq.) and the product was extracted into DCM. The combined organic phases were dried with $MgSO_4$ (anh), filtered and concentrated to obtain a brown oil. The crude product was further purified using basic alumina (activated Brockman I) eluting with DCM:MeOH:TEA (98:1:1) yielding (once concentrated) a light yellow oil (3.88 g, 73%). $^1$H NMR (700 MHz, Chloroform-d) δ 10.20 (s, 1H), 7.52 (d, J=8.8 Hz, 1H), 6.70 (d, J=8.8 Hz, 1H), 4.18 (t, J=6.5 Hz, 2H), 4.06 (t, J=6.5 Hz, 2H), 4.00 (t, J=6.5 Hz, 2H), 2.55-2.35 (m, 6H), 2.33-2.01 (m, 18H), 1.97 (p, J=6.8 Hz, 2H), 1.91 (ddt, J=12.9, 8.5, 6.3 Hz, 4H). $^{13}$C NMR (176 MHz, Chloroform-d) δ 189.05, 158.98, 156.47, 140.94, 123.99, 123.58, 108.37, 73.58, 72.09, 67.28, 56.66, 56.44, 56.26, 45.63, 45.61, 45.59, 28.62, 28.54, 27.51.

Synthesis of 2,3,4-tris(3-(dimethylamino)propoxy) fulleropyrrolidine ($C_{60}$-N)

A 1-neck, 250 mL round-bottom flask equipped with a magnetic stir bar, inlet adapter, and Vigreux column was flushed with nitrogen, followed by addition of 2 (300 mg, 0.73 mmol), fullerene-$C_{60}$ (792 mg, 1.10 mmol), sarcosine (200 mg, 2.2 mmol) and 1,2-dichlorobenzene (110 mL). The mixture was degassed with nitrogen and then heated to reflux for 1 hour. The reaction was concentrated, dissolved in chloroform and filtered. The resulting filtrate was concentrated and then dissolved in carbon disulfide ($CS_2$). The crude mixture was added to silica gel, wet packed with hexanes, and eluted with $CS_2$, followed by $CH_2Cl_2$:TEA:MeOH (95:5:5). The first brown band that eluted was collected and concentrated, dissolved in chloroform, filtered through a 1 □m PTFE filter and precipitated into acetone. The precipitate was washed with acetone and dried to obtain the desired product as a brown solid (374 mg, 44%). $^1$H NMR (300 MHz, Chloroform-d) δ 7.61 (d, J=8.8 Hz, 1H), 6.78 (d, J=8.8 Hz, 1H), 5.37 (s, 1H), 4.97 (d, J=9.3 Hz, 1H), 4.26 (d, J=9.4 Hz, 1H), 4.16 (t, J=6.2 Hz, 2H), 4.09-3.99 (m, 2H), 3.94 (t, J=6.5 Hz, 2H), 2.78 (s, 3H), 2.58-2.46 (m, 4H), 2.45-2.37 (m, 2H), 2.31 (s, 6H), 2.26 (s, 6H), 2.21 (s, 6H), 2.07-1.91 (m, 4H), 1.87-1.75 (m, 2H). $^{13}$C NMR (176 MHz, Chloroform-d) δ 156.85, 155.05, 154.31, 154.19, 152.98, 152.58, 147.40, 147.06, 146.83, 146.42, 146.36, 146.35, 146.29, 146.23, 146.18, 146.17, 146.05, 146.04, 145.85, 145.67, 145.64, 145.42, 145.40, 145.37, 145.35, 145.24, 145.20, 144.71, 144.70, 144.54, 144.46, 143.19, 143.10, 142.74, 142.73, 142.67, 142.64, 142.40, 142.38, 142.27, 142.26, 142.22, 142.17, 142.09, 141.97, 141.80, 141.79, 141.72, 141.33, 140.26, 140.21, 139.62, 139.60, 136.69, 136.58, 136.07, 134.97, 124.56, 122.77, 108.92, 76.36, 72.23, 71.77, 70.03, 67.08, 56.98, 56.75, 56.62, 45.87, 45.70, 45.66, 40.23, 28.93, 28.39, 27.81. MALDI-TOF (m/z): [M+H]$^+$ calculated for: $C_{84}H_{45}N_4O_3$: 1157.34, found: 1157.60.

Synthesis of 2,3,4-tris(3-(propylsulfobetaine) propoxy)fulleropyrrolidine ($C_{60}$-SB)

A 1-neck, 15 mL round-bottom flask equipped with a magnetic stir bar, inlet adapter, condenser and septum was flushed with nitrogen, followed by addition of 17 (250 mg, 0.22 mmol), 1,3-propanesultone (250 mg, 2.05 mmol), $Na_2CO_3$ (70 mg, 0.65 mmol) and TFE (5 mL). The reaction was heated to reflux while stirring for 24 hours, then cooled to room temperature. The product was precipitated into THF, filtered and washed with THF, followed by re-dissolving into TFE (5 mL), centrifuging and filtering through a 1 □m PTFE syringe filter into a dialysis membrane (1 kDa cutoff). The contents of the dialysis bag were dialyzed against pure water in a 4 L beaker for 24 hours (changing the water five times) and then the water was removed by lyophilization. The product was obtained as a pure light brown fluffy solid (286 mg, 87%). $^1$H NMR (700 MHz, 2,2,2,-Trifluoroethanol-d$_3$) δ 7.90 (br, 1H), 6.99 (br, 1H), 5.32 (br, 1H), 5.05 (br, 1H), 4.42-4.24 (m, 3H), 4.24-4.15 (m, 2H), 4.11-4.00 (m, 2H), 3.69-3.58 (m, 3H), 3.58-3.40 (m, 9H), 3.14 (br, 6H), 3.12-2.99 (m, 12H), 2.99-2.90 (m, 6H), 2.80 (br, 3H), 2.32 (br, 4H), 2.23 (br, 6H), 2.14 (br, 2H). MALDI-TOF (m/z): [M+H]$^+$ calculated for: $C_{93}H_{63}N_4O_{12}S_3$: 1524.36, found: 1524.19.

Synthesis of 2,3,4-tris(hexyloxy)benzaldehyde (3)

A 2-neck, 250 mL round-bottom flask equipped with a magnetic stir bar, inlet adapter, addition funnel and septa was flushed with nitrogen, followed by addition of 2,3,4-trihydroxybenzaldehyde (2.00 g, 13.0 mmol), 1-hexanol (4.51 g, 44.1 mmol), triphenylphosphine (11.57 g, 44.1 mmol) and THF (anh, 45 mL). The mixture was cooled to 0° C. with an ice bath while stirring under nitrogen. Diisopropyl azodicarboxylate was added to the addition funnel, dissolved in THF (anh, 15 mL) and added dropwise to the reaction mixture. After complete addition the flask was removed from the ice bath and stirred at room temperature for five hours. The reaction was concentrated and the resulting crude mixture was washed with hexanes, filtering off the white phosphine-oxide byproduct through celite. The filtrate was concentrated to obtain a light brown oil. The oil was subjected to silica gel chromatography for further purification, eluting with Hex:EtOAc (95:5) to obtain the product as the first UV-active band to elute. After concentrating the solution the product was obtained as a clear light yellow oil (1.73 g, 33%). $^1$H NMR (700 MHz, Chloroform-d) δ 10.26 (s, 1H), 7.57 (d, J=8.7 Hz, 1H), 6.71 (d, J=8.8 Hz, 1H), 4.17 (t, J=6.7 Hz, 2H), 4.04 (t, J=6.5 Hz, 2H), 3.97 (t, J=6.7 Hz, 2H), 1.84 (dt, J=15.1, 6.6 Hz, 2H), 1.77 (ddt, J=15.7, 9.2, 6.7 Hz, 4H), 1.52-1.42 (m, 6H), 1.38-1.31 (m, 12H), 0.91 (t, J=7.3 Hz, 9H). $^{13}$C NMR (176 MHz, Chloroform-d) δ 189.27, 159.29, 156.83, 141.17, 123.85, 123.61, 108.21, 75.46, 73.90, 69.07, 31.84, 31.76, 31.65, 30.38, 30.26, 29.27, 25.90, 25.85, 25.81, 22.79, 22.73, 22.72, 14.18, 14.15, 14.13.

Synthesis of 2,3,4-tris(hexyloxy)fulleropyrrolidine ($C_{60}$-alkyl)

A 1-neck, 250 mL round-bottom flask equipped with a magnetic stir bar, inlet adapter, and Vigreux column was flushed with nitrogen, followed by addition of 3 (298 mg, 0.73 mmol), fullerene-$C_{60}$ (792 mg, 1.10 mmol), sarcosine (200 mg, 2.2 mmol) and 1,2-dichlorobenzene (110 mL). The mixture was degassed with nitrogen and then heated to reflux for 1 hour. The reaction was concentrated, dissolved in chloroform and filtered. The resulting filtrate was concentrated and then dissolved in carbon disulfide ($CS_2$). The crude mixture was added to silica gel, wet packed with hexanes, and eluted with $CS_2$, followed by Hex:$CH_2Cl_2$ (1:1). The first brown band that eluted was collected and concentrated, dissolved in chloroform, filtered through a 1 □m PTFE filter and precipitated into acetone. The precipitate was washed with acetone and dried to obtain the desired product as a brown solid (446 mg, 53%). $^1$H NMR (700 MHz, Chloroform-d) δ 7.60 (d, J=8.8 Hz, 1H), 6.74 (d, J=8.9 Hz, 1H), 5.38 (s, 1H), 4.96 (d, J=9.3 Hz, 1H), 4.26 (d, J=9.3 Hz, 1H), 4.11 (qt, J=9.3, 6.5 Hz, 2H), 3.97 (ddt, J=32.7, 9.4, 6.5 Hz, 2H), 3.91-3.84 (m, 2H), 2.78 (s, 3H), 1.84-1.71 (m, 4H), 1.64-1.57 (m, 2H), 1.52-1.43 (m, 4H), 1.41-1.30 (m, 10H), 1.29-1.19 (m, 4H), 0.91 (dh, J=18.2, 4.5, 4.1 Hz, 6H), 0.85 (t, J=7.0 Hz, 3H). $^{13}$C NMR (176 MHz, Chloroform-d) δ 156.92, 155.19, 154.48, 154.20, 153.19, 152.76, 147.42, 147.40, 147.18, 146.87, 146.54, 146.37, 146.36, 146.31, 146.24, 146.19, 146.17, 146.06, 145.87, 145.71, 145.67, 145.43, 145.42, 145.37, 145.36, 145.34, 145.23, 145.20, 144.72, 144.71, 144.58, 144.46, 143.19, 143.10, 142.75, 142.73, 142.68, 142.64, 142.42, 142.39, 142.31, 142.26, 142.22, 142.19, 142.08, 141.99, 141.79, 141.78, 141.75, 141.45, 140.24, 140.20, 139.59, 139.57, 136.74, 136.55, 136.15, 134.87, 124.33, 122.57, 108.56, 76.49, 73.94, 73.40, 70.09, 69.31, 68.76, 40.27, 31.94, 31.84, 31.77, 30.61, 30.10, 29.53, 26.13, 25.97, 25.86, 22.96, 22.80, 22.75, 14.37, 14.23, 14.18. MALDI-TOF (m/z): [M+H]$^+$ calculated for: $C_{87}H_{47}N_4NO_3$: 1153.36, found: 1154.35.

OPV Device Fabrication and Characterization

Photovoltaic devices were fabricated by spin coating poly(ethylenedioxythiophene):poly(styrene sulfonate) (PEDOT:PSS) (H. C. Starck, I 4083) onto pre-cleaned, patterned indium tin oxide (ITO) substrates (10Ω/□, from Thin Film Devices, Inc.). PEDOT:PSS was baked at 150° C. for 30 minutes, and transferred to the glove box ($N_2$ atmosphere, <1 ppm $O_2$, <1 ppm $H_2O$) for photoactive layer deposition. A mixture of PCE-10 and $PC_{71}BM$ (1:2 weight ratio) or PTB7 and $PC_{71}BM$ (1:1.5 weight ratio) in chlorobenzene:1,8-diiodoocatane (2.5 v % DIO) was stirred at 80° C. for ~1 day. The photoactive layers were deposized by spin-coating the mixture solution onto the prepared substrates. The thickness of the active layer film after spin-coating was ~100 (determined by profilometry, Table 3). DIO was removed under vacuum, and the devices were placed in a glove box for spin-coating of $C_{60}$-N or $C_{60}$-SB and thermal evaporation of metal electrode through a shadow mask. Film thickness was measured by KLA-TENCOR Alpha-Step IQ Surface Profiler. Current-voltage (I-V) characteristics were measured using a Keithley 2400 source-meter under simulated AM1.5G irradiation using a 300 W Xe lamp solar simulator (Newport 91160). The light intensity was adjusted with an NREL-calibrated Si reference solar cell and KG-5 filter. The illuminated area (0.03025 cm$^2$) was defined by using a photomask with an aperture the area of which was tested by NREL.

In another experiment, the indium tin oxide (ITO)-coated glass substrates (20±5 ohms/square) were bought from Thin Film Devices Inc., and were cleaned through ultrasonic treatment in detergent, DI water, acetone, and isopropyl alcohol and then dried in an oven overnight. The substrates were transferred into a glove box ($N_2$ atmosphere, <1 ppm $O_2$, <1 ppm $H_2O$). $C_{60}$-SB solution (2,2,2-Trifluoroethanol) with different concentration (from 0.25 mg/ml to 30 mg/ml) was spin-coated (4000 rpm, 60 s) onto ultraviolet ozone-treated ITO substrates to obtain film thickness from 1.8 nm to 139.2 nm. The thicknesses were determined by taking an average of thickness values over the absorption wavelength region, given pre-determined attenuation coefficients (cm$^{-1}$).[40] A mixture of PCE-10 and $PC_{71}BM$ (1:1.8 weight ratio) in chlorobenzene:1,8-diiodoocatane (3.2 v % DIO) was stirred at 80° C. for ~1 day. The photoactive layers were deposited by spin-coating BHJ solution onto $C_{60}$-SB layer or bare ITO substrate. The thickness of the active layer film was ~100 nm (determined by profilometry). DIO was removed under vacuum, followed by thermal evaporation of $MoO_3$ and metal electrode through a shadow mask created four devices on each substrate. Performance characteristics of those devices were averaged. The overlap between the bottom ITO electrode and the top metal electrode defined the maximum available device area of 0.06 cm$^2$. Current-voltage (I-V) characteristics were measured in a $N_2$ atmosphere using a Keithley 2400 source-meter under simulated AM1.5G irradiation using a 300 W Xe lamp solar simulator (Newport 91160). The light intensity was adjusted with an NREL-calibrated Si reference solar cell and KG-5 filter. The illuminated area (0.05255 cm$^2$) was defined by a photomask with an aperture, the area of which was measured at NREL, and used in all reported PCE measurements.

In this specification and the appended claims, the singular forms "a," "an," and "the" include plural reference, unless the context clearly dictates otherwise.

Unless defined otherwise, all technical and scientific terms used herein have the same meaning as commonly understood by one of ordinary skill in the art. Although any methods and materials similar or equivalent to those described herein can also be used in the practice or testing of the present disclosure, the preferred methods and materials are now described. Methods recited herein may be carried out in any order that is logically possible, in addition to a particular order disclosed.

INCORPORATION BY REFERENCE

References and citations to other documents, such as patents, patent applications, patent publications, journals, books, papers, web contents, have been made in this disclosure. All such documents are hereby incorporated herein by reference in their entirety for all purposes. Any material, or portion thereof, that is said to be incorporated by reference herein, but which conflicts with existing definitions, statements, or other disclosure material explicitly set forth herein is only incorporated to the extent that no conflict arises between that incorporated material and the present disclosure material. In the event of a conflict, the conflict is to be resolved in favor of the present disclosure as the preferred disclosure.

EQUIVALENTS

The representative examples are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples and the references to the scientific and patent literature included herein. The examples contain important additional information, exemplification and guidance that can be adapted to the practice of this invention in its various embodiments and equivalents thereof.

The invention claimed is:

1. A fullerene derivative having the structural formula:

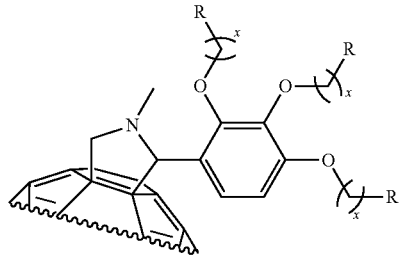

wherein
R each is independently
a neutral group selected from primary, secondary, tertiary amino groups, phosphonate ester group, phosphoric acid group, or a zwitterionic group selected from sulfobetaine, carboxybetaine, phosphobetaine and phosphorylcholine groups; and x is an integer from 1 to 12.

2. The fullerene derivative of claim 1, wherein the fullerene is $C_{60}$.

3. The fullerene derivative of claim 1, wherein the fullerene is $C_{70}$.

4. The fullerene derivative of claim 1, wherein all R's are identical.

5. The fullerene derivative of claim 1, wherein all R's are not identical.

6. The fullerene derivative of claim 1, wherein each R is a neutral group.

7. The fullerene derivative of claim 1, wherein each R is a tertiary amino group.

8. The fullerene derivative of claim 1, wherein each R is a zwitterionic group, wherein the zwitterionic group is selected from the group consisting of sulfobetaine, carboxybetaine, phosphobetaine and phosphorylcholine.

9. The fullerene derivative of claim 1, wherein x is an integer from 1 to 6.

* * * * *